(12) United States Patent
Davidson et al.

(10) Patent No.: US 8,875,709 B2
(45) Date of Patent: Nov. 4, 2014

(54) MASK ASSEMBLY

(75) Inventors: Aaron S. Davidson, Newport (AU);
Lemmy Nga, Glenwood (AU); Michael J. Reid, Stanmore (AU); Angelene M. Ozolins, Wahroonga (AU); Scott A. Howard, Harbord (AU); Amal S. Amarasinghe, West Pennant Hills (AU); Dimitri M. Maurer, Umina (AU); Bart J. Caffin, Clontarf (AU)

(73) Assignee: ResMed Limited, Bella Vista (AU)

( * ) Notice: Subject to any disclaimer, the term of this patent is extended or adjusted under 35 U.S.C. 154(b) by 954 days.

(21) Appl. No.: 12/117,084

(22) Filed: May 8, 2008

(65) Prior Publication Data

US 2008/0276937 A1 Nov. 13, 2008

Related U.S. Application Data

(60) Provisional application No. 60/924,359, filed on May 10, 2007.

(51) Int. Cl.

| | |
|---|---|
| *A61M 16/06* | (2006.01) |
| *A62B 18/02* | (2006.01) |
| *A62B 18/08* | (2006.01) |
| *A61M 16/08* | (2006.01) |
| *A61M 16/20* | (2006.01) |

(52) U.S. Cl.
CPC ............ *A61M 16/06* (2013.01); *A61M 16/0622* (2013.01); *A61M 2205/42* (2013.01); *A61M 16/0816* (2013.01); *A61M 16/085* (2013.01); *A61M 16/20* (2013.01); *A61M 16/0633* (2013.01); *A61M 16/0858* (2013.01); *A61M 2205/3375* (2013.01); *A61M 16/0683* (2013.01); *A61M 16/0616* (2013.01)
USPC .................................. 128/206.28; 128/206.21

(58) Field of Classification Search
USPC ............. 128/204.18, 205.25, 206.21–206.24, 128/206.26, 206.28, 207.11, 207.13, 128/207.17; D24/110.1, 110.4, 110.5, 164
See application file for complete search history.

(56) References Cited

U.S. PATENT DOCUMENTS 5,243,971 A * 9/1993 Sullivan et al. .......... 128/205.25
6,374,826 B1 4/2002 Gunaratnam et al.
(Continued)

FOREIGN PATENT DOCUMENTS

WO WO 2005123166 A1 * 12/2005
WO WO 2006/074517 7/2006
(Continued)

OTHER PUBLICATIONS

ResMed's Ultra Mirage II Nasal Mask brochure 2005 copyright.*

(Continued)

*Primary Examiner* — (Jackie) Tan-Uyen Ho
*Assistant Examiner* — Kathryn E Ditmer
(74) *Attorney, Agent, or Firm* — Nixon & Vanderhye P.C.

(57) ABSTRACT

A mask assembly adapted for use with a positive airway pressure device, includes a mask frame, an elbow assembly provided to the frame, a cushion provided to the frame, a forehead support assembly, and a neck to connect the frame to the forehead support assembly, wherein the neck includes a pair of side walls having a streamlined design that is made to look sleek and reduce or minimize obtrusiveness. The pair of side walls may take the form of a single wall or more than two walls. The mask frame may include a recessed port structure including at least one port having access to an interior of the frame which at least in part with the cushion defines a breathing chamber in communication with a nasal passage of the patient in use. The mask frame may also include a channel to receive the cushion. The channel is formed by an outer wall and an inner wall and the channel includes an inner surface having a bead to engage with an outer surface of an edge of the cushion. The forehead support assembly includes a forehead support and a forehead pad coupled to the forehead support. The elbow assembly includes an elbow connectable to the mask frame. A cover is releasably connectable to the elbow. The cover includes a venting area including a plurality of vent holes.

54 Claims, 65 Drawing Sheets

(56) References Cited

U.S. PATENT DOCUMENTS

| | | | |
|---|---|---|---|
| 6,412,487 B1 | 7/2002 | Gunaratnam et al. | |
| 6,467,483 B1 * | 10/2002 | Kopacko et al. | 128/207.12 |
| 6,532,961 B1 | 3/2003 | Kwok et al. | |
| D489,817 S * | 5/2004 | Ankey et al. | D24/110.4 |
| D502,261 S * | 2/2005 | Kopacko et al. | D24/110.4 |
| 6,907,882 B2 | 6/2005 | Ging et al. | |
| D507,831 S * | 7/2005 | Rosenkranz et al. | D24/110.1 |
| 7,011,090 B2 * | 3/2006 | Drew et al. | 128/202.27 |
| 7,188,620 B2 | 3/2007 | Amarasinghe | |
| 2003/0019496 A1 * | 1/2003 | Kopacko et al. | 128/206.24 |
| 2003/0172936 A1 * | 9/2003 | Wilkie et al. | 128/207.18 |
| 2004/0112384 A1 * | 6/2004 | Lithgow et al. | 128/206.21 |
| 2004/0112387 A1 * | 6/2004 | Lang et al. | 128/206.24 |
| 2004/0216747 A1 * | 11/2004 | Jones et al. | 128/206.21 |
| 2005/0150497 A1 * | 7/2005 | Eifler et al. | 128/206.21 |
| 2005/0155603 A1 * | 7/2005 | Frerichs et al. | 128/206.21 |
| 2006/0237018 A1 * | 10/2006 | McAuley et al. | 128/206.24 |
| 2007/0044804 A1 * | 3/2007 | Matula et al. | 128/206.21 |
| 2007/0062537 A1 * | 3/2007 | Chiesa et al. | 128/207.11 |
| 2008/0066759 A1 * | 3/2008 | Howard et al. | 128/206.21 |
| 2009/0126739 A1 | 5/2009 | Ng et al. | |
| 2009/0139527 A1 | 6/2009 | Ng et al. | |
| 2013/0233316 A1 | 9/2013 | Ng et al. | |

FOREIGN PATENT DOCUMENTS

| | | |
|---|---|---|
| WO | WO 2006074517 A1 * | 7/2006 |
| WO | WO 2007/143793 A1 | 12/2007 |
| WO | WO 2007143793 A1 * | 12/2007 |

OTHER PUBLICATIONS

ResMed's Ultra Mirage II Nasal Mask User Guide 2004 copyright.*
U.S. Appl. No. 60/858,694, filed Nov. 2006, Chu et al.

* cited by examiner

FIG. 9-12
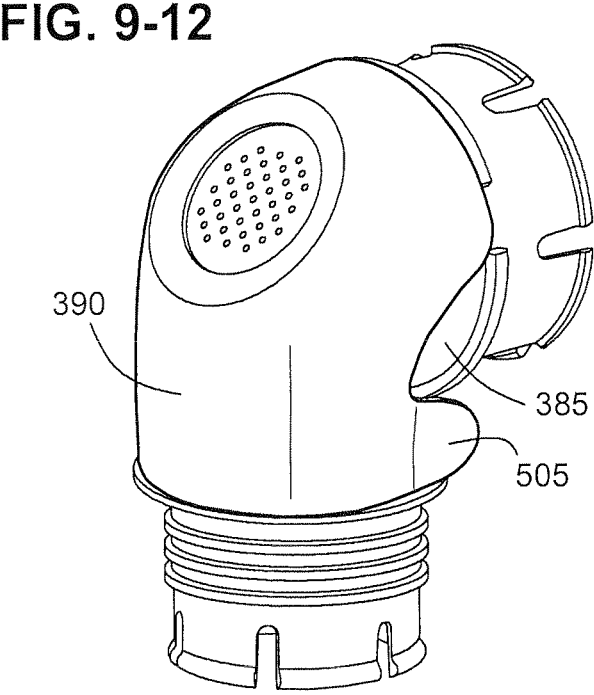
FIG. 9-13
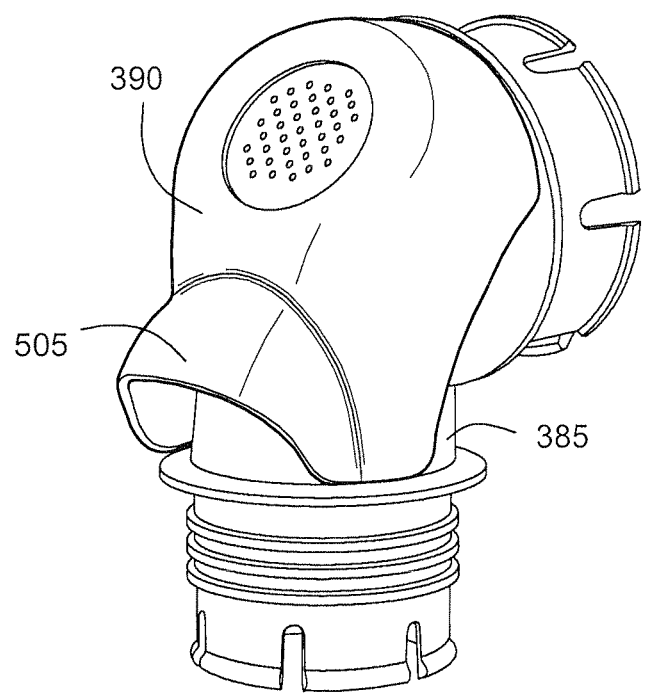
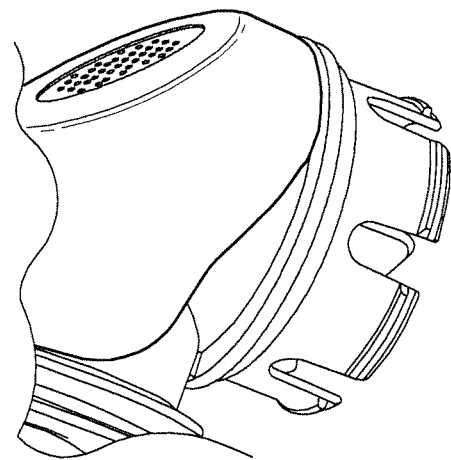
FIG. 9-14

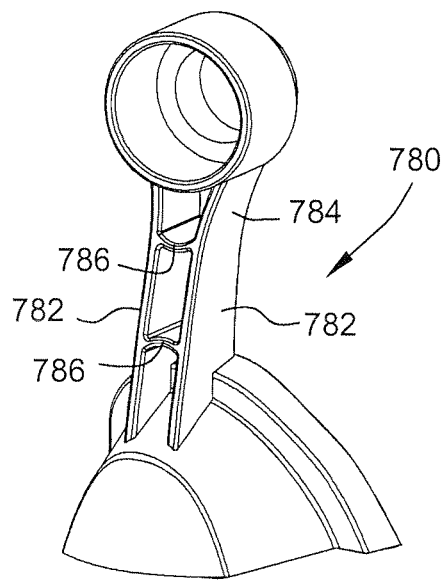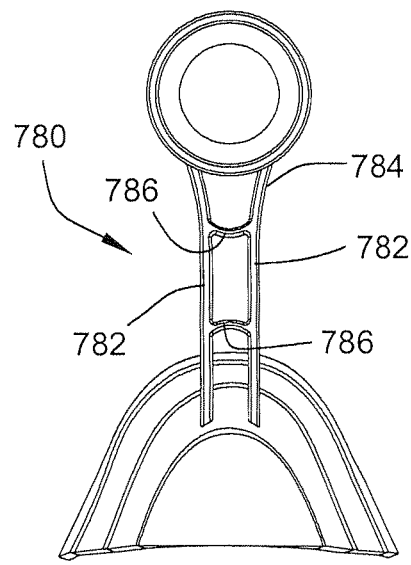
FIG. 21-1                    FIG. 21-2
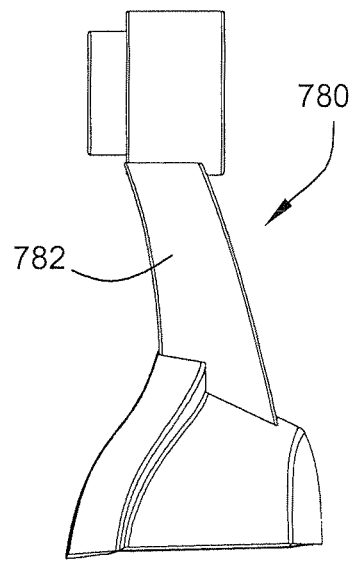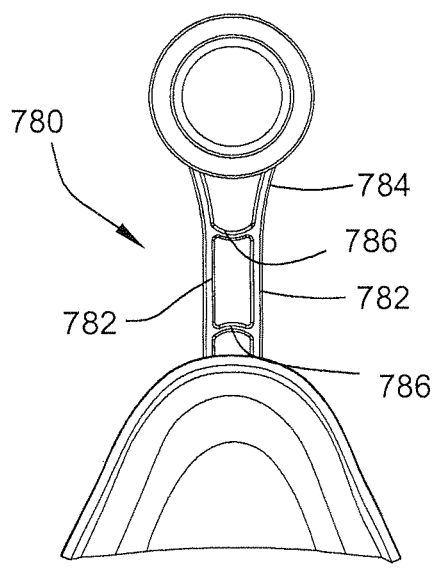
FIG. 21-3                    FIG. 21-4

MASK ASSEMBLY

CROSS REFERENCE TO RELATED APPLICATION

This application claims priority to U.S. Application 60/924,359, filed May 10, 2007, the entire contents of which are incorporated herein by reference.

FIELD OF THE INVENTION

The present invention relates to respiratory masks, and in particular to a mask assembly for use with the treatment of respiratory diseases such as obstructive sleep apnea.

BACKGROUND OF THE INVENTION

ResMed's Ultra Mirage II mask is described in U.S. Pat. No. 6,532,961, incorporated herein by reference. That mask has a frame, a cushion and a forehead support which is adjustably connected to the frame. While the Ultra Mirage II has been tremendously successful in the marketplace, and functions quite well for its intended treatment purposes, there is a continuing need to create a mask that is more efficient and/or requires less flow, less noisy, more aesthetically pleasing, easier and/or less expensive to manufacture, and/or easier and/or more intuitive to assemble from the patient's perspective, etc.

SUMMARY OF THE INVENTION

One aspect of the invention relates to a frame for a mask assembly having a neck which is unobtrusive and/or blends well with the other components of the mask.

Another aspect of the invention relates to a channel formed in a mask frame for receiving the edge of a cushion, wherein the frame includes a bead extending only along a portion of the channel. The channel may also have one or more ribs therein for improved manufacturability.

Another aspect of the invention relates to a mask frame with a lead-in surface or rib to aid in locating headgear clips into receptacles on the frame.

Another aspect relates to a mask frame with a recessed port structure that is positioned and/or designed to reduce "rainout."

Another aspect of the invention relates to a cushion for a mask assembly having a side wall design which facilitates assembly of the cushion to the mask frame.

Another aspect of the invention relates to a forehead support assembly for a mask assembly having slotted connectors which are shaped and positioned to improve aesthetics and/or minimize obtrusiveness.

Another aspect of the invention is directed to an elbow including a baffle to increase gas washout efficiency and/or reduce flow requirements.

Another aspect is directed to a vented cover that is provided to the frame or elbow of a mask assembly which includes a plurality of holes being patterned, positioned and dimensioned to decrease noise and/or reduce the possibility of fouling of the holes.

Another aspect is directed to a vented cover for a mask assembly which is structured to form a hard seal between the cover and the frame or elbow of the mask assembly. The cover may include one or more wings to facilitate disassembly of the vented cover.

Another aspect is directed to a mask assembly having one or more of the above attributes.

According to one sample embodiment of the invention, there is provided a mask assembly adapted for use with a positive airway pressure device, comprising a mask frame, a cushion provided to the frame, a forehead support assembly, and a neck to connect the frame to the forehead support assembly, wherein the neck includes a pair of side walls having a streamlined design that is made to look sleek and reduce or minimize obtrusiveness.

According to another sample embodiment of the invention, there is provided a mask assembly adapted for use with a positive airway pressure device, comprising a mask frame, a cushion provided to the frame, a pair of clip receptacles, and a recessed port structure including at least one port having access to an interior of the frame which at least in part with cushion defines a breathing chamber in communication with a nasal passage of the patient in use, wherein a lower portion of the recessed port structure is slightly offset from and lower than a lower edge of a receptacle on the frame that receives a headgear clip.

According to another sample embodiment of the invention, there is provided a mask assembly adapted for use with a positive airway pressure device, comprising a mask frame, a cushion provided to the frame, a pair of clip receptacles, and a guide structure provided adjacent each clip receptacle for the purpose of guiding each clip into position upon assembly of the clip with the clip receptacle.

According to another sample embodiment of the invention, there is provided a mask assembly adapted for use with a positive airway pressure device, comprising a mask frame, a cushion provided to the frame, wherein the frame includes a channel to receive the cushion, and wherein the channel is formed by an outer wall and an inner wall and the channel includes an inner surface having a bead to engage with an outer surface of the edge of the cushion, wherein the bead only extends around a portion of the perimeter of the surface of the inner or outer wall facing the channel.

According to another sample embodiment of the invention, there is provided a mask assembly adapted for use with a positive airway pressure device, comprising a mask frame, a cushion provided to the frame, and a forehead support assembly, wherein the forehead support assembly includes a forehead support and a forehead pad coupled to the forehead support, wherein the forehead pad is provided to or otherwise connected to the forehead support using a pair of elastic support shafts each including a head portion resiliently squeezed into support holes positioned on the main body of the forehead support and wherein the forehead support has a length that is less than the length of the pad.

According to another sample embodiment of the invention, there is provided a mask assembly adapted for use with a positive airway pressure device, comprising a mask frame, an elbow assembly provided to the frame, wherein the elbow has a main body includes a pair of lugs on opposed sides of a vent opening defined by a generally circular upstanding wall terminating with a rim, a cushion provided to the frame; and a cover including one or more retaining members provided on an inside surface of cover to releasably engage with at least one of the lugs.

According to another sample embodiment of the invention, there is provided a mask assembly adapted for use with a positive airway pressure device, comprising a mask frame, an elbow provided to the frame, and a cushion provided to the frame, wherein the elbow includes a baffle that is positioned adjacent where the elbow connects to frame and divides an upper arm of the elbow into an air delivery passage and an exhaust passage, wherein the baffle is cantilevered towards the first end of the elbow such that the sides of the baffle are not supported by the interior side walls of the elbow at least along a portion of the length of the baffle.

According to another sample embodiment of the invention, there is provided a mask assembly adapted for use with a positive airway pressure device, comprising a mask frame, a cushion provided to the frame, and wherein the cushion includes a face engaging portion and an oppositely oriented frame engaging portion, wherein the frame engaging portion includes a relatively thickened, tongue like member of a tongue and groove arrangement, and wherein the frame engaging portion has a curved profile that form a strengthening arch so the user may apply an assembly force to a laterally central region of the face engaging portion of the cushion to cause the frame engaging portion to be inserted into frame.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 2-1 to 2-6 show a mask frame according to an example of the present invention;

FIGS. 3-1 to 3-8 show a forehead support and forehead support pad assembly according to an example of the present invention;

FIGS. 4-1 to 4-6 show a forehead support according to an example of the present invention;

FIGS. 5-1 to 5-12 show an elbow assembly according to an example of the present invention;

FIGS. 6-1 to 6-6 show an elbow according to an example of the present invention;

FIG. 6-7 shows an elbow according to another example of the present invention;

FIGS. 7-1 to 7-9 show a vented cover according to an example of the present invention;

FIGS. 7-10 to 7-12 show a vented cover according to another example of the present invention;

FIGS. 8-1 to 8-2 show additional examples of vented covers according to the present invention;

FIGS. 9-1 to 9-24 show additional examples of elbows or elbow assemblies according to the present invention;

FIGS. 10-1 to 10-14 show a cushion according to an example of the present invention;

FIGS. 11-1 to 11-6 show a cushion according to another example of the present invention;

FIGS. 12-1 to 12-6 show a cushion according to another example of the present invention; and FIGS. 13-1 to 24-4 are partial views of the frame showing alternative necks according to the present invention.

DETAILED DESCRIPTION OF ILLUSTRATED EMBODIMENTS

Figure 1:
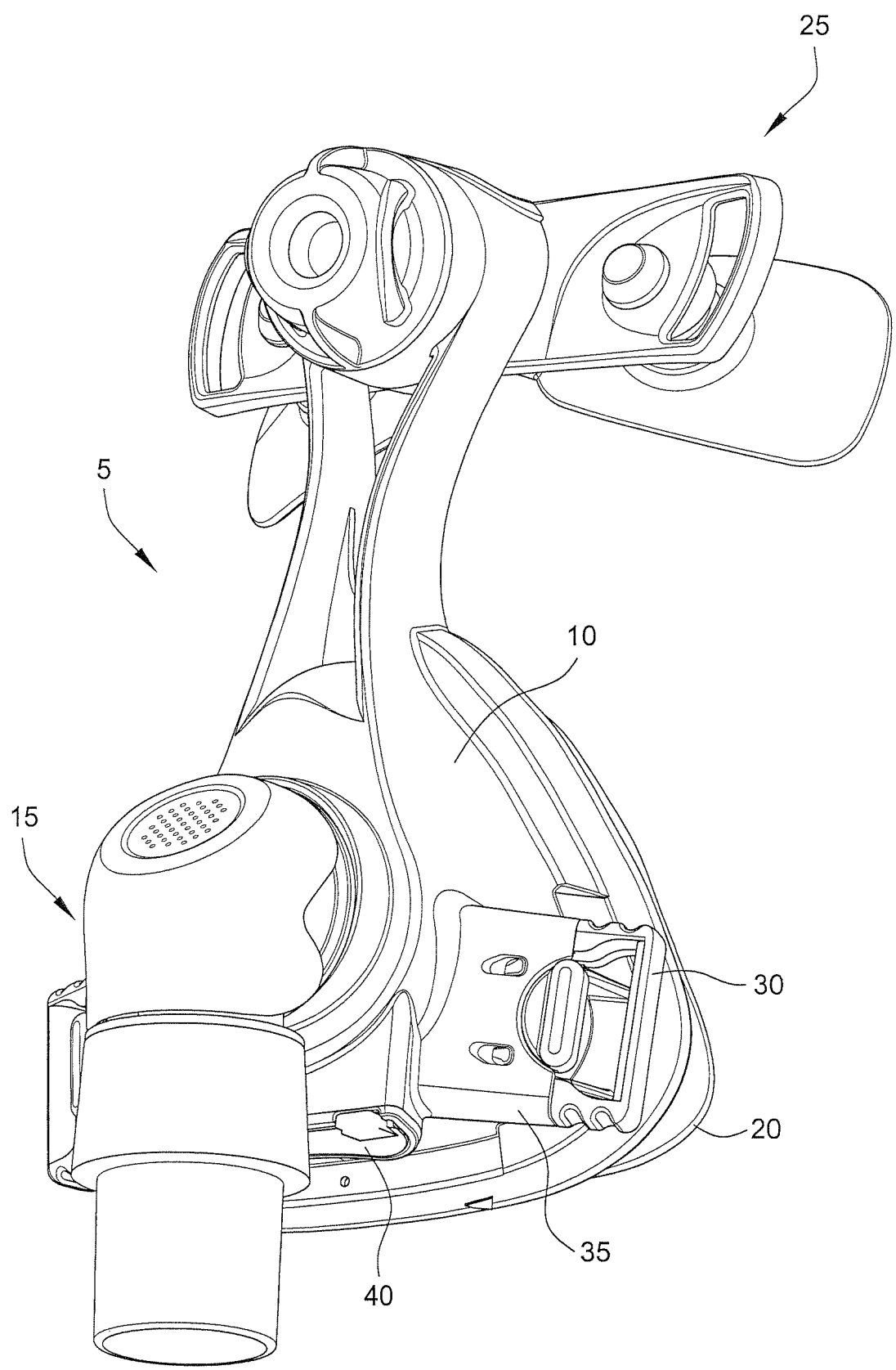
FIGS. 1-1 to 1-7 show a mask assembly according to an example of the present invention.

The following description is provided in relation to several embodiments which may share common characteristics and features. It is to be understood that one or more features of any one embodiment may be combinable with one or more features of the other embodiments. In addition, any single feature or combination of features in any of the embodiments may constitute an additional embodiment.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids other than air.

1.0 Overall Assembly

FIGS. 1-1 to 1-7 show a mask assembly 5 according to an example of the present invention. Mask assembly 5 is adapted for use with a positive airway pressure (PAP) device, a non-invasive positive pressure ventilation (NIPPV) apparatus or a continuous positive airway pressure (CPAP) device, for the delivery of pressurized gas to a patient who suffers from sleep disordered breathing and/or other disorders, such as obstructive sleep apnea (OSA). Such PAP, CPAP or NIPPV devices typically include a source of pressurized gas which is pressurized in the range of about 2-30 cm $H_2O$ at a flow rate of about 150-200 l/min, which gas is delivered to the mask via an air delivery conduit.

Mask assembly 5 includes a mask frame 10, an elbow assembly 15 provided to frame 10, a cushion 20, a forehead support assembly 25, a pair of headgear clips 30 that are received in respective receptacles 35 of frame 10 and a ports plug 40, each of which is separately described below and/or shown in the figures described herein.

Mask assembly 5 is in the form of a nasal mask which is adapted to be worn by a patient such that only the nose is covered by cushion, and the mouth is not covered or is otherwise left open to atmosphere. However, it should be appreciated that the teachings herein can also be applied to full face (oro-nasal) masks, as well as to mouth-only masks, nasal cannulae, or nasal pillows, prongs, nozzles or puffs, etc.

2.0 Frame

Figures 1, 2:
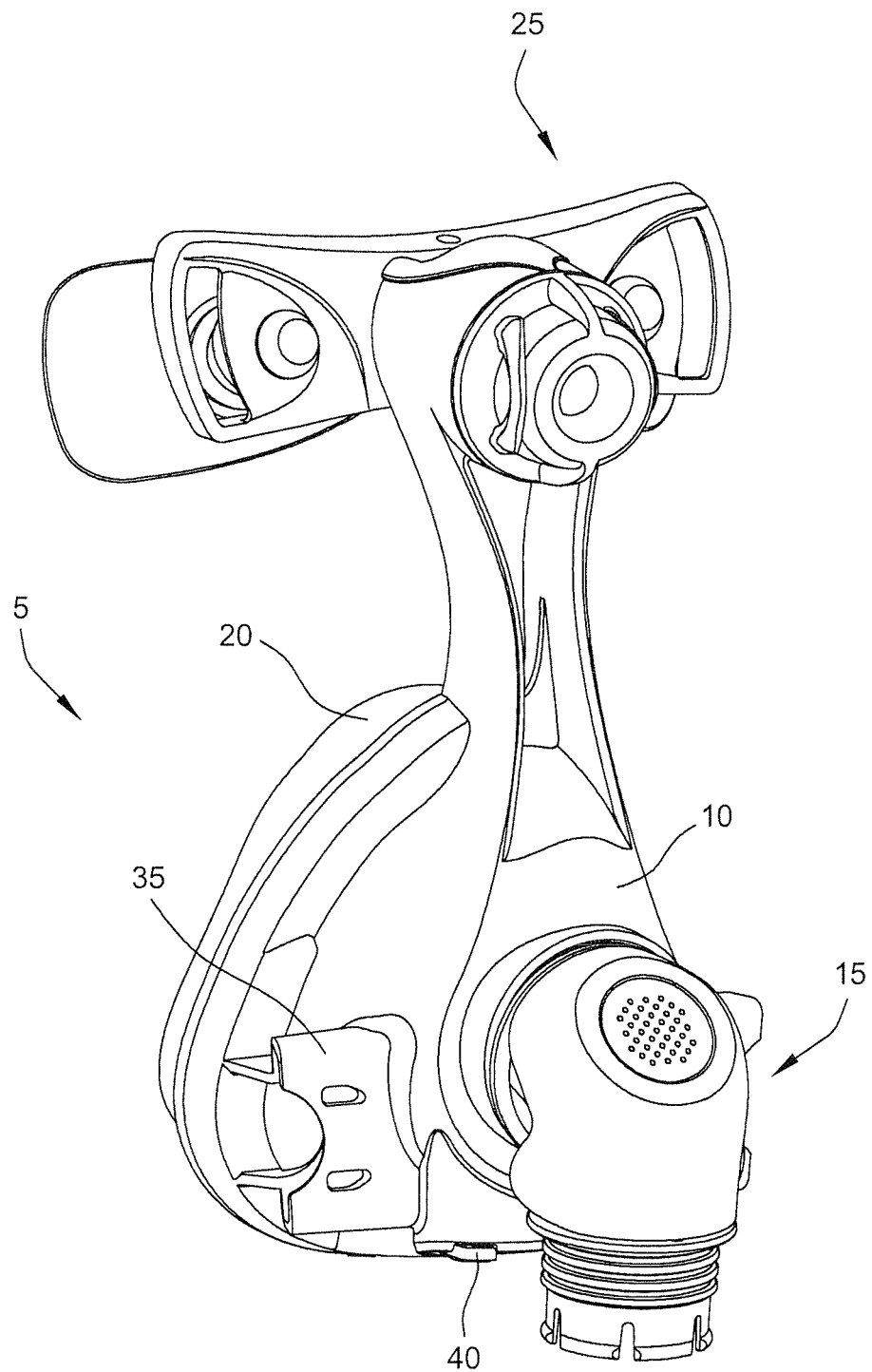

FIGS. 2-1 to 2-6 show mask frame 10 in isolation, with FIG. 2-1 showing the ports plug 40 in an exploded, detached position. Frame 10 includes a lower portion 45 referred to as a "shell" and is made of a fairly rigid material, such as polycarbonate or similar materials.

2.1 Ports Plug

Ports plug 40 includes a main body 50 and a cap portion 55 at each end of the main body. Ports plug 40 is made of a resilient elastic (e.g., silicone) member and is releasably coupled to a recessed port structure 60 in frame 10 in order to selectively cover or expose one or more ports 65 (best seen in FIG. 2-5), each of which has access to the interior of the frame which at least in part with cushion defines a breathing chamber in communication with a nasal passage of the patient. Each port 65 can be used to supply supplemental gas to and/or to measure pressure, sound, etc., in the breathing chamber.

Each cap portion 55 includes a recess or blind bore to receive port 65, e.g., in the form of a tubular or cylindrical extension. Each cap portion 55 is inserted into a respective port cap recess 75 in the frame 10. The frame 10 includes a relatively more shallow recess 80 compared to the depth of the port cap recesses 75, to receive a bridging portion 85 of ports plug 40. The bridging portion 85 and the cap portions 55 are preferably flush with the frame in the fully inserted position (FIGS. 1-1 and 1-3) so as to minimize interference or reduce snagging with the patient and/or air delivery hose. The bridging portion 85 may include a central rib 86 (FIG. 2-1) that is engagable by the user's finger to allow the ports plug 40 to be pushed into the port recess 75. The port(s) plug 40 includes one or more pull tabs 90 that are dimensioned to be received within respective tab recesses 95 provided on the front wall of frame, such that the tabs extend away from the patient in use.

2.2 Port Cap Recess

Each port cap recess 75 (FIG. 2-5) is positioned so as to reduce the possibility of tangling between any tubes coupled to the ports of the frame and the elbow assembly and/or the air delivery tube that is coupled to the elbow.

In addition, especially as compared to ResMed's Ultra Mirage I and II Masks (see, e.g., U.S. Pat. No. 6,532,961, incorporated by reference in its entirety), recessed port structure is positioned to reduce so called "rainout". In particular, as shown in FIGS. 2-1 and 2-2, the lower portion 100 of recessed port structure 60 is slightly offset from and lower than the lower edge 105 of each receptacle 35 that receives a respective headgear clip by a small distance. However, as seen in FIG. 2-2 and FIG. 2-6, the recessed port structure 60 preferably does not extend below the lower edge 110 of the bottom of frame. In addition, a small land 115 is provided between a rear wall 120 of the recessed port structure 60 and an opposite wall 125. The patient's finger can be inserted into land 115 and braced against opposite wall 125 when assembling the cushion 20 to the frame 10.

Further, as seen in FIG. 2-5, recessed port structure 60 is spaced outwardly a distance 130 from the lower edge 110 of the frame. The front wall 135 of the recessed port structure 60 protrudes slightly above the adjacent receptacles 35. Also, the front wall 135 of the recessed port structure 60 is only slightly recessed relative to a main front wall 145 of the frame 10, as seen in FIG. 2-6.

The position of recessed port structure 60 helps to reduce "rainout" because the overall volume of the breathing chamber is increased, while at the same time maintaining a low profile and without increasing obtrusiveness. The increased volume may help accumulate water which can be used to humidify the gas provided in the breathing chamber.

2.3 Neck

Lower portion 45 has a generally triangular shape with two lateral side walls 150 that converge at an apex 155 (FIG. 2-3) and a lower or bottom wall 160 which connects the opposite diverging ends of the side walls 150. The apex 155 is generally located over the nasal bridge region of the patient, while the side walls 150 extend along and follow the sides of the nose, and the bottom wall 160 is positioned over the face between the upper lip and the tip of the nose.

Apex 155 may be optionally provided or fitted with a neck 165 to support a further component, such as forehead support assembly 25 (FIG. 1-7). Neck 165 may be integrally molded with lower portion 45, or it may be formed as a separate (add-on) component that is selectively attachable to the apex 155 or frame 10. If it is detached, some provision for accommodating one or more headgear straps should be provided, e.g., a separate attachment or a second neck may include a slotted connector to accommodate an over the top type strap and/or upper side straps.

2.3.1. Neck Side Walls

Neck 165 includes a pair of side walls 170 having a streamlined design that is made to look sleek and reduce or minimize obtrusiveness, and/or at the very least provide the appearance of smallness. Neck 165 is thin (e.g., each side wall 170 has a thickness of about 1 mm to 5 mm, or about 2.5 mm) and is preferably made of a transparent material, again to minimize obtrusiveness. The side walls 170 are spaced from one another at least along a portion thereof, but preferably along their entire length, from the lower end 175 that is coupled to the apex to the upper end 180 that is coupled with the forehead support assembly 25 (FIG. 1-7 and 2-3). An open space 182 between the walls 170 also has the effect or reducing obtrusiveness and provides a more comfortable feeling for the patient.

Figures 1, 9:
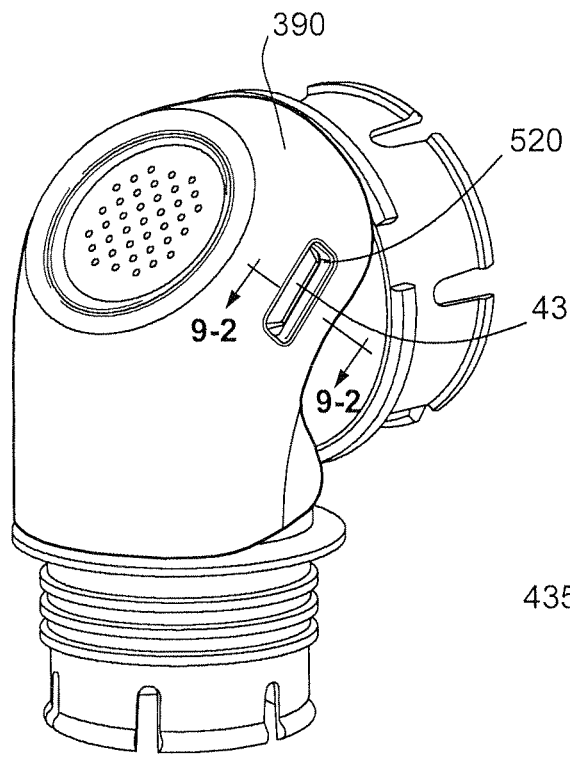
Figures 2, 9:
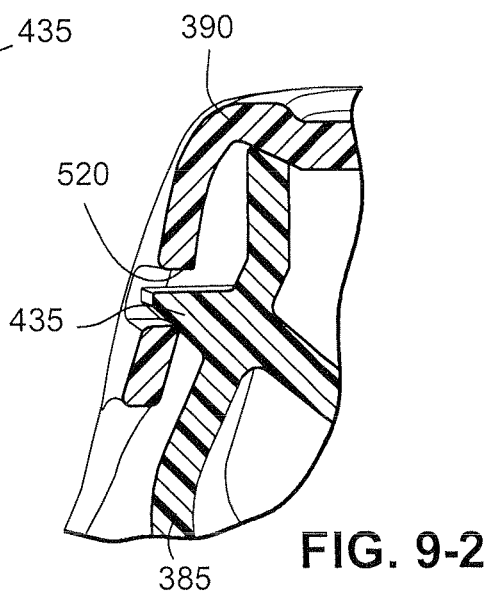
Figures 3, 9:
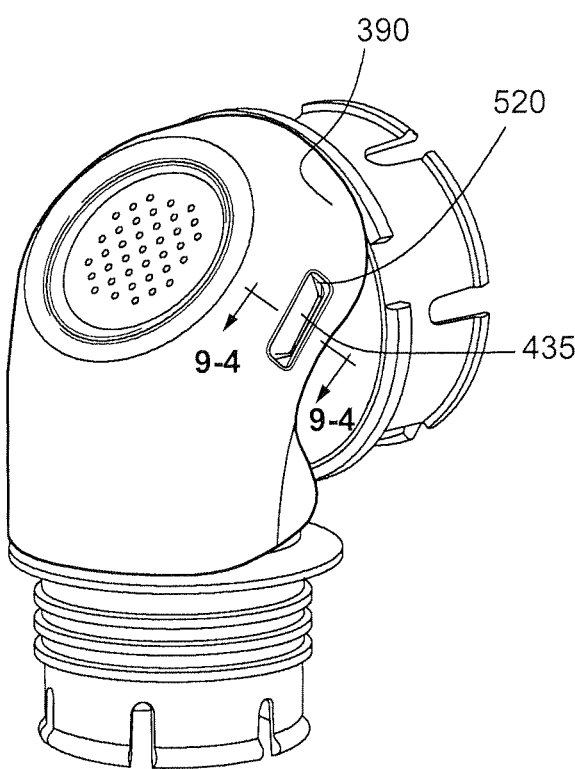
Figures 4, 9:
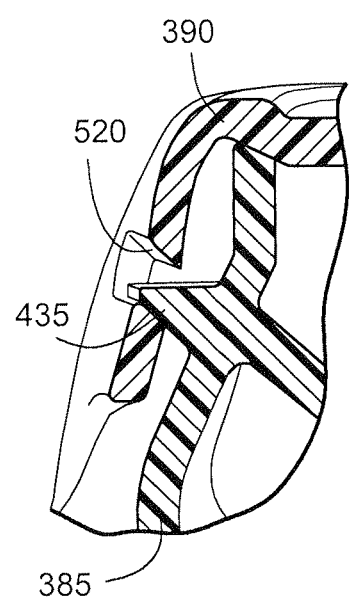
Figures 5, 9:
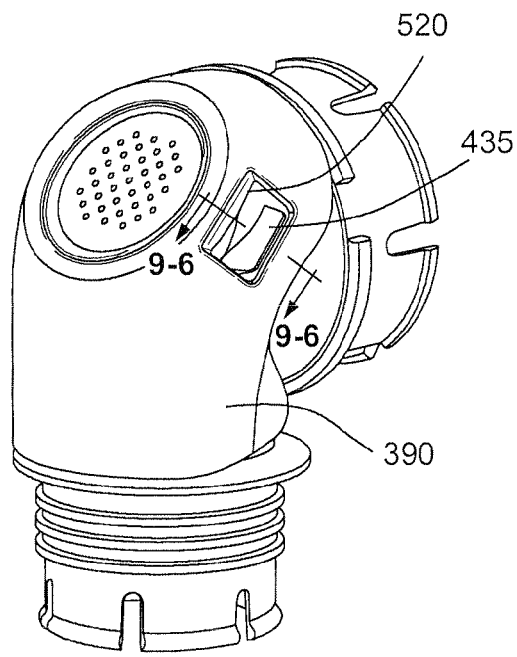
Figures 6, 9:
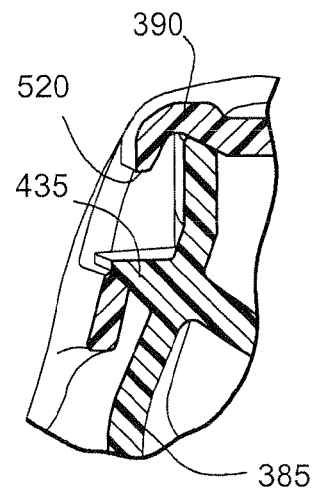
Figures 7, 9:
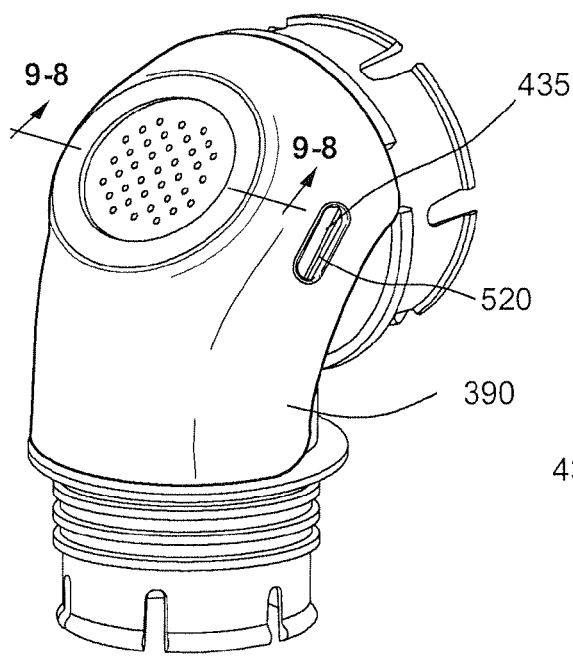
Figures 8, 9:
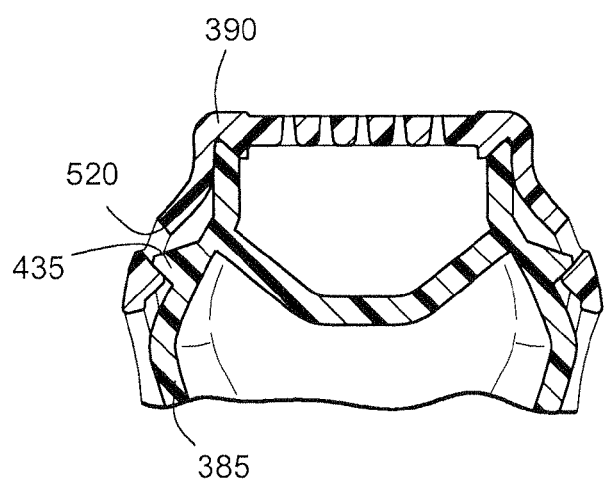
Figure 9:
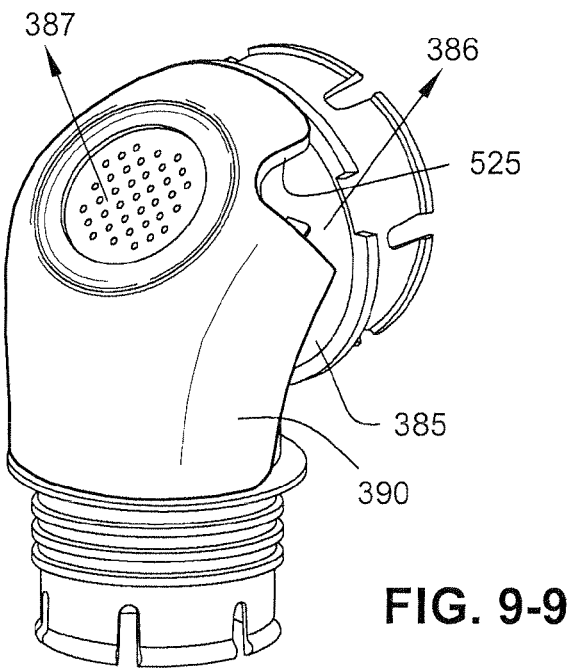
Figures 9, 10:
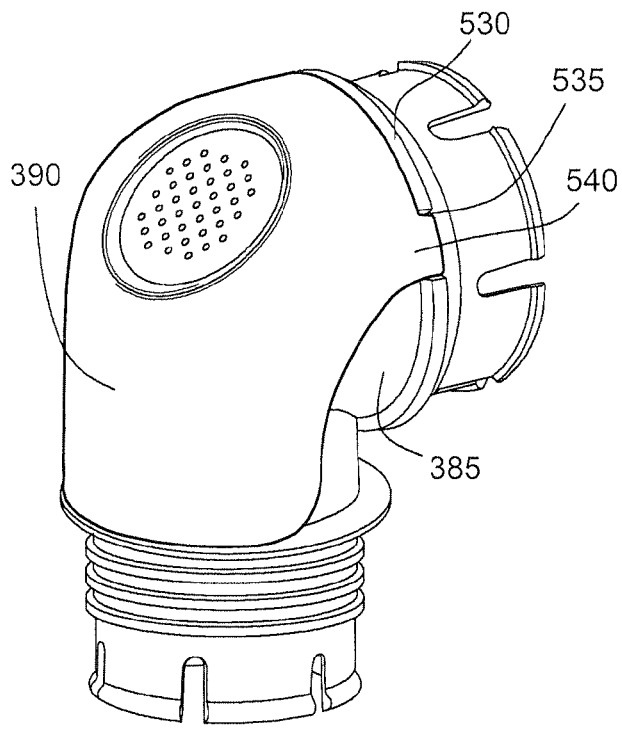
Figures 9, 10, 11:
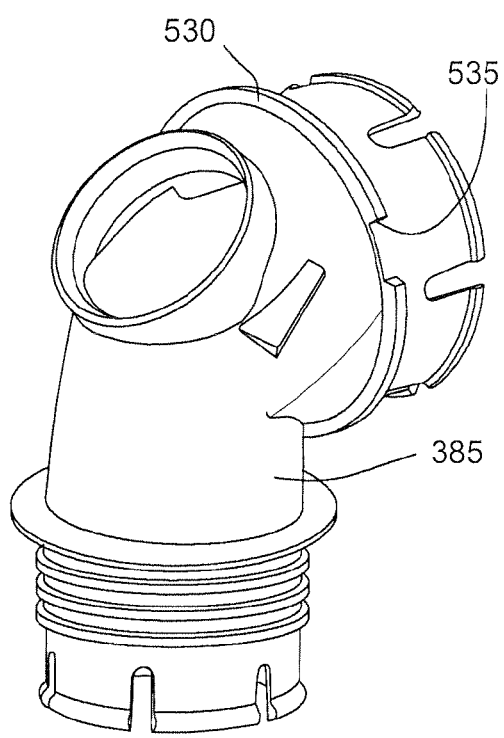
Figures 9, 10, 11, 12, 13, 14, 15:
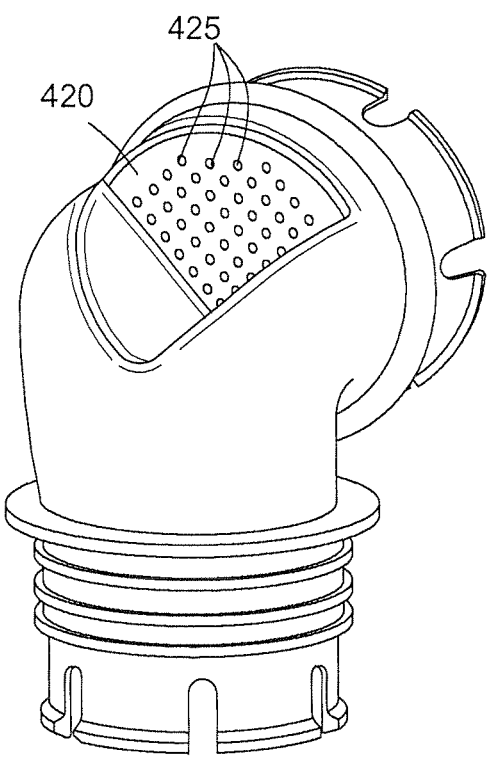
Figures 9, 10, 11, 12, 13, 14, 15, 16:
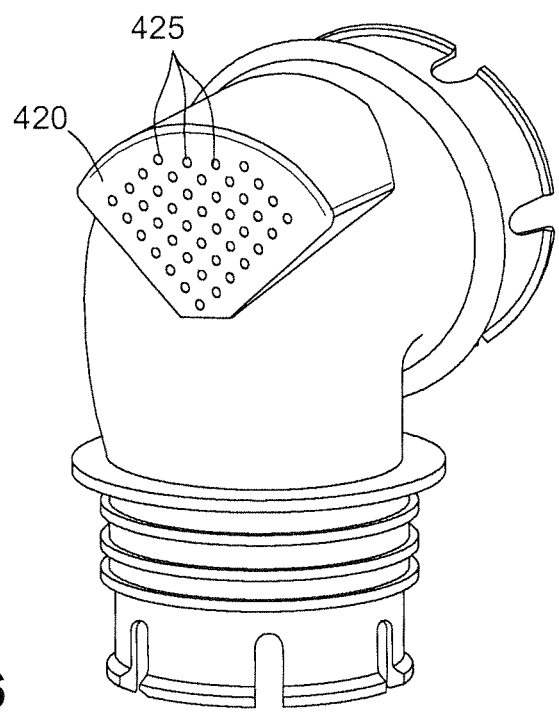
Figures 9, 10, 11, 12, 13, 14, 15, 16, 17:
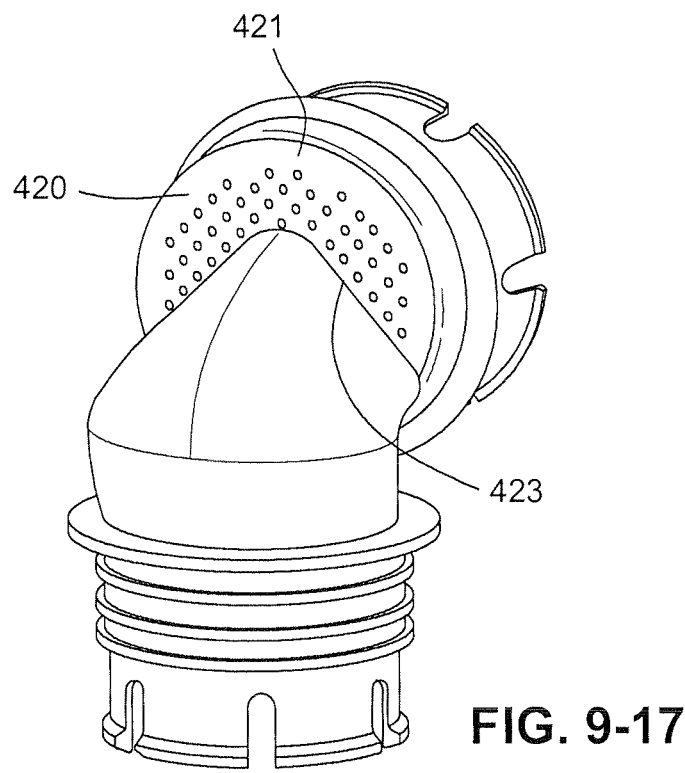
Figures 9, 10, 11, 12, 13, 14, 15, 16, 17, 18:
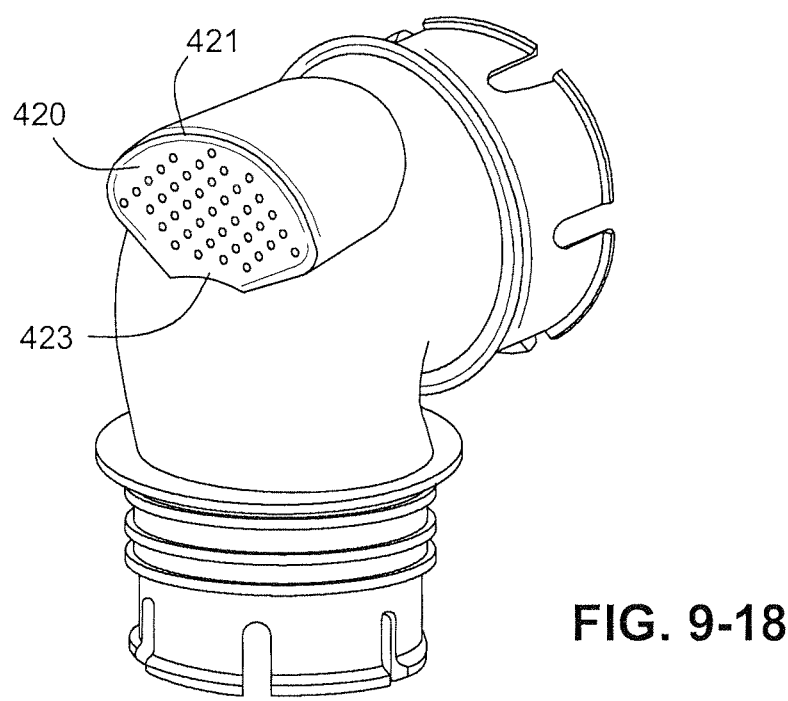
Figures 9, 10, 11, 12, 13, 14, 15, 16, 17, 18, 19:
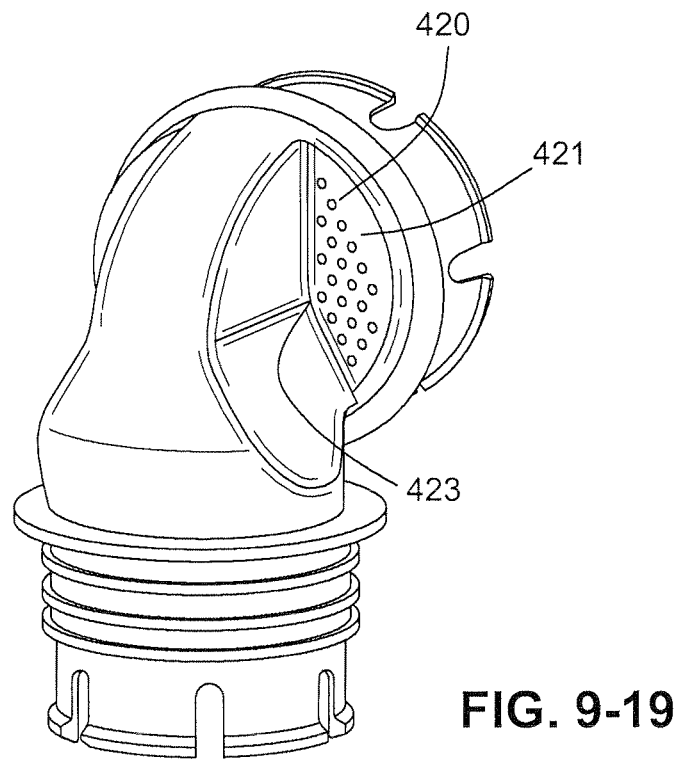
Figures 9, 10, 11, 12, 13, 14, 15, 16, 17, 18, 19, 20:
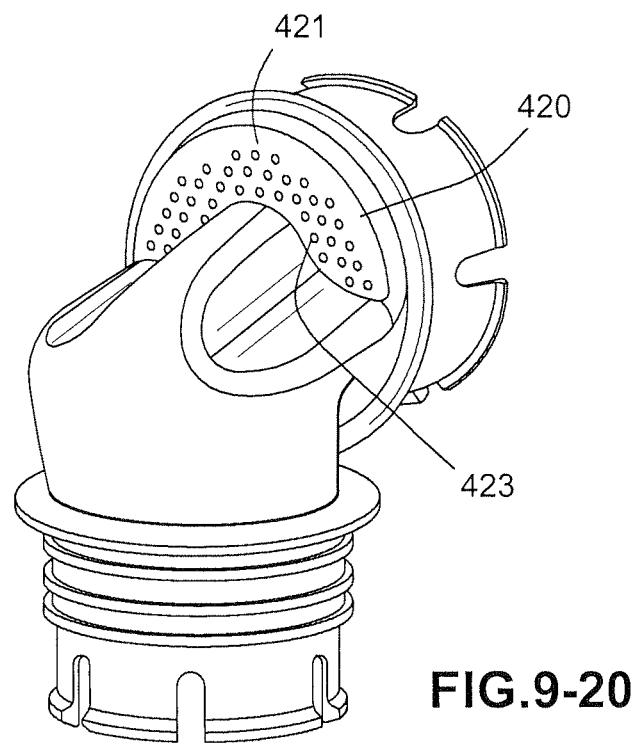
Figures 9, 10, 11, 12, 13, 14, 15, 16, 17, 18, 19, 20, 21:
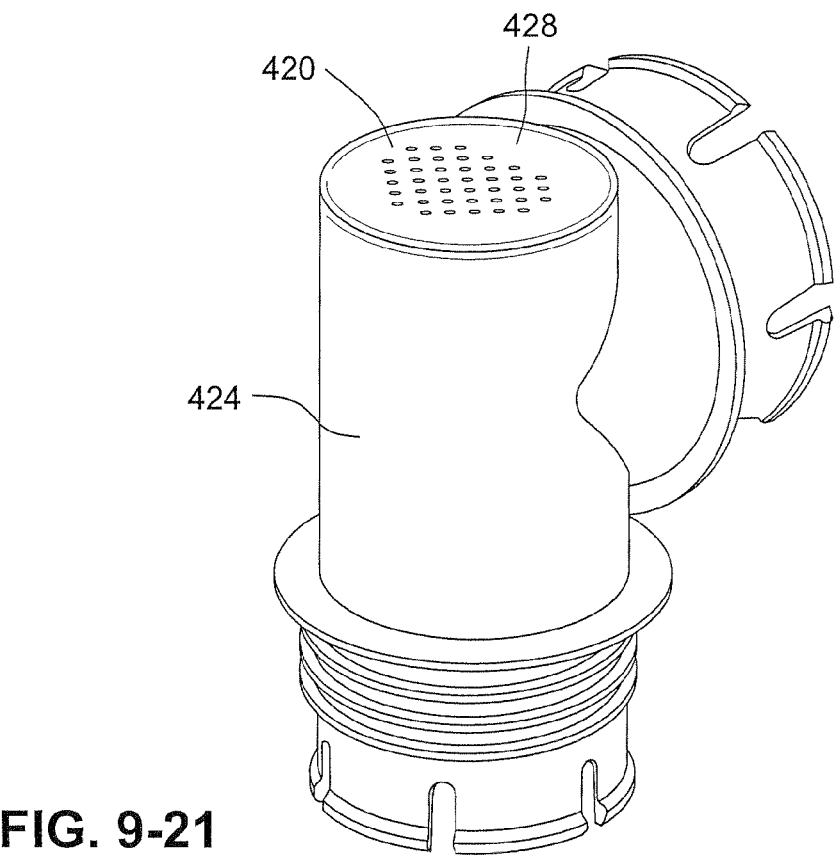
Figures 9, 10, 11, 12, 13, 14, 15, 16, 17, 18, 19, 20, 21, 22:
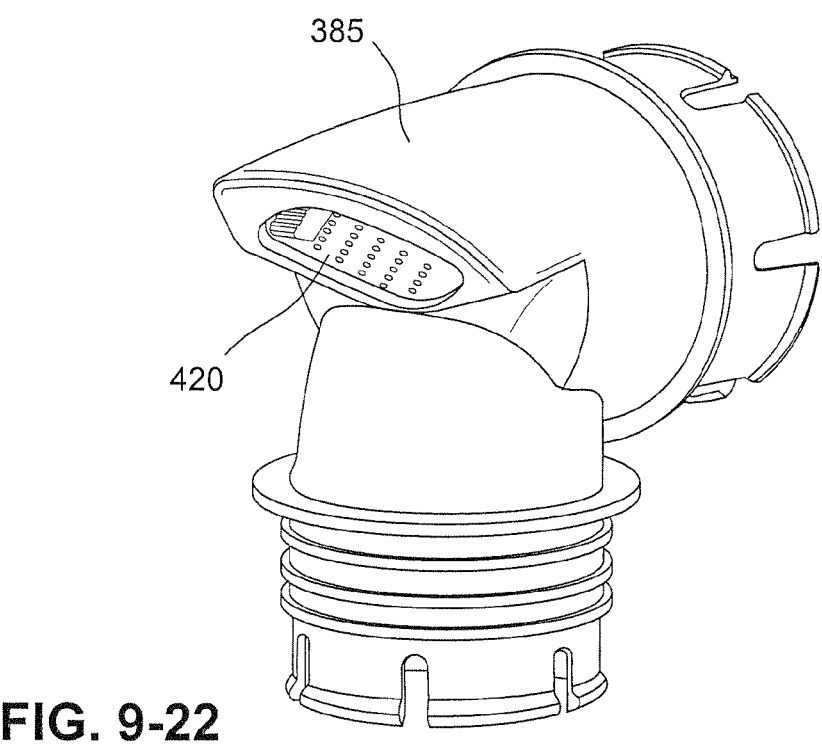
Figures 9, 10, 11, 12, 13, 14, 15, 16, 17, 18, 19, 20, 21, 22, 23:
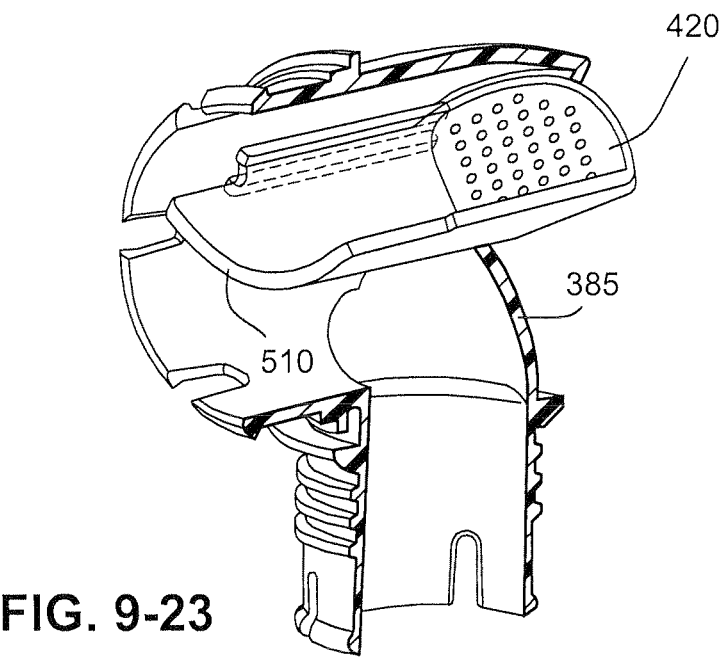
Figures 9, 10, 11, 12, 13, 14, 15, 16, 17, 18, 19, 20, 21, 22, 23, 24:
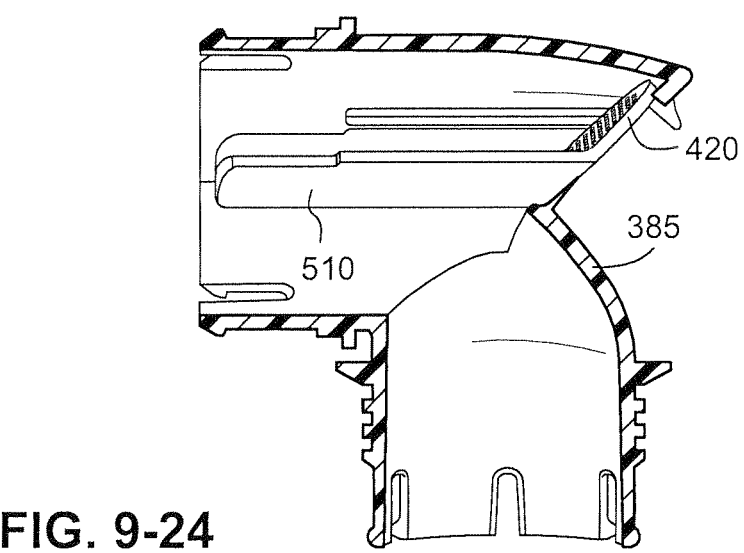
Figures 1, 10:
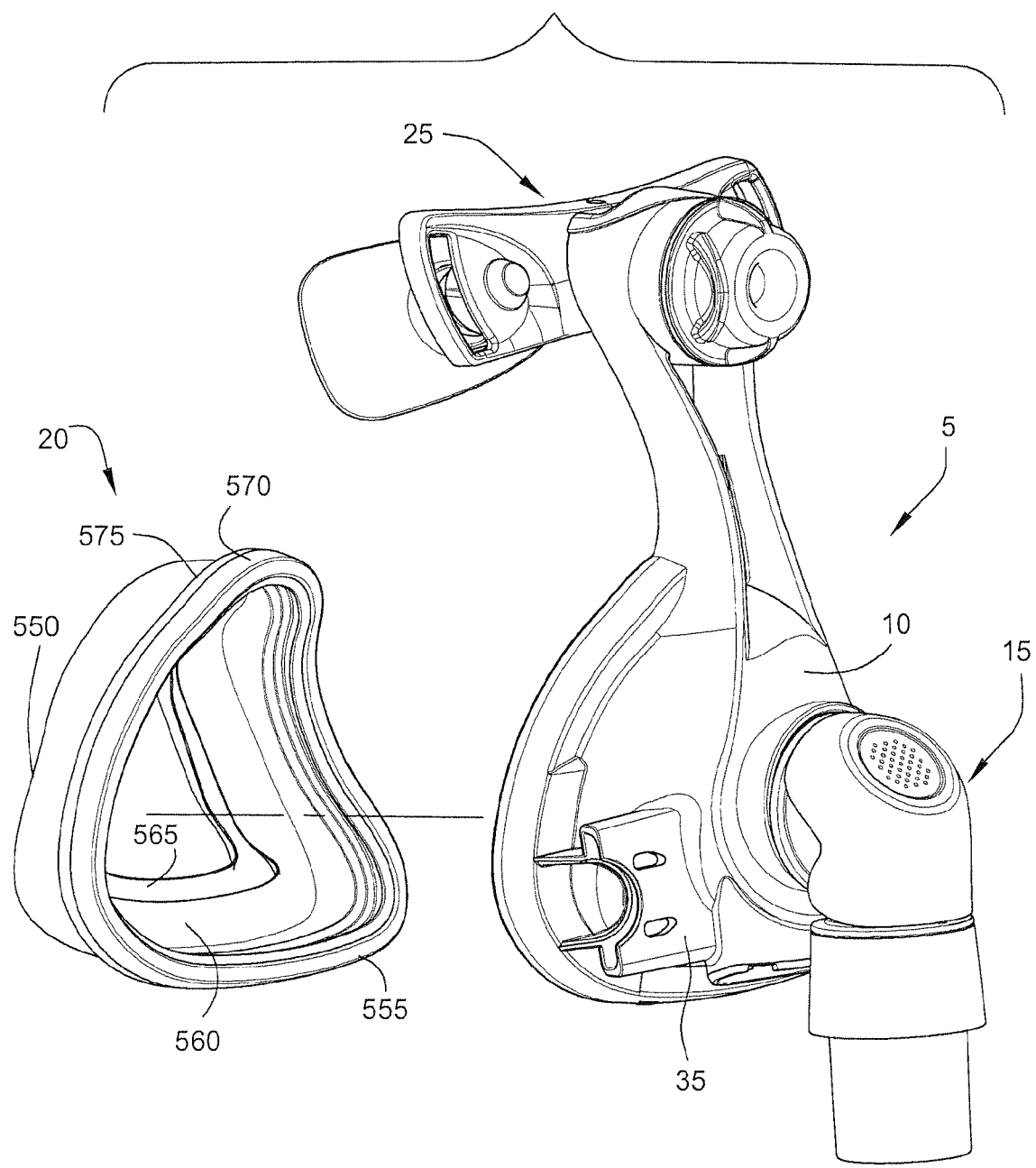
Figures 2, 10:
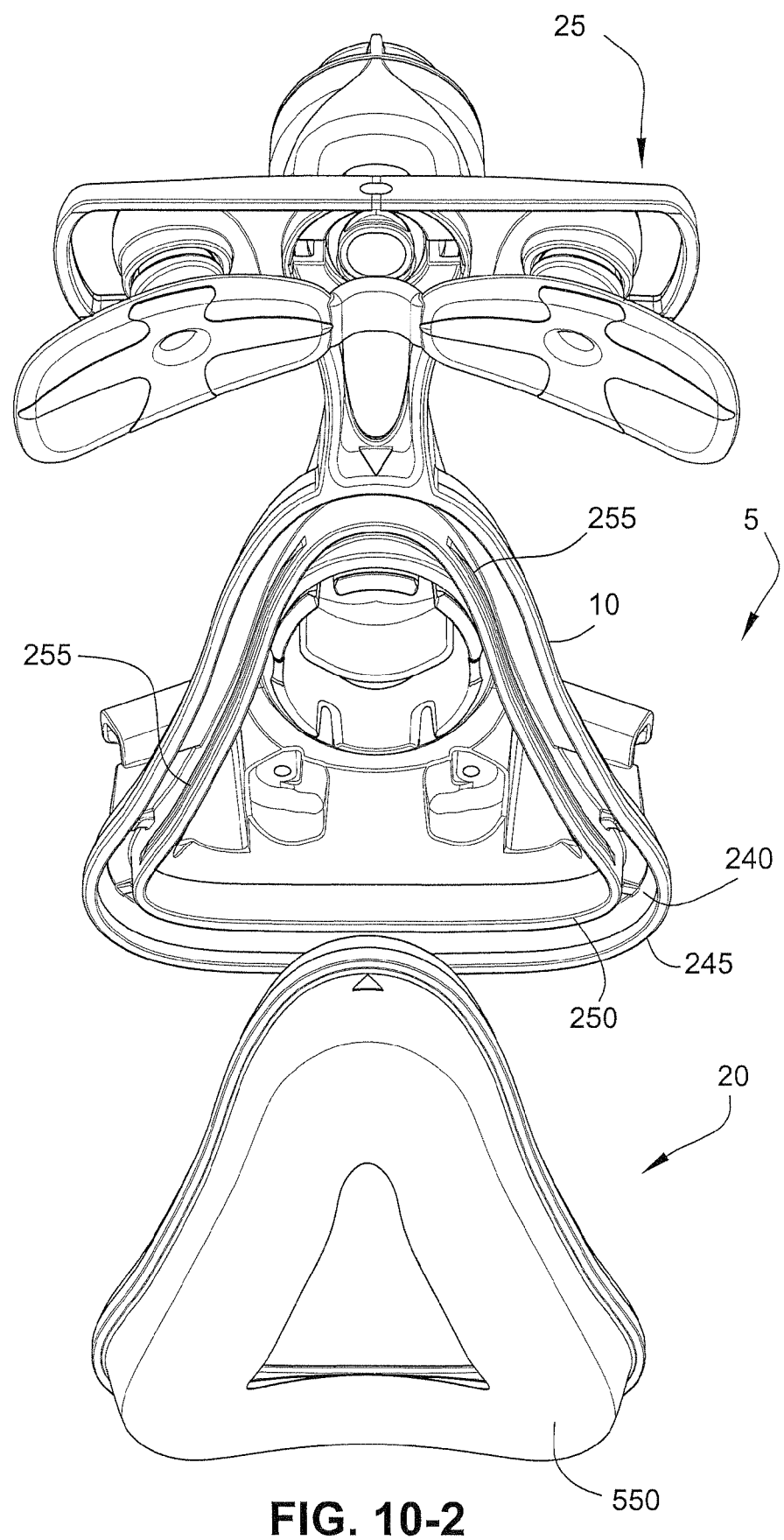
Figures 3, 10:
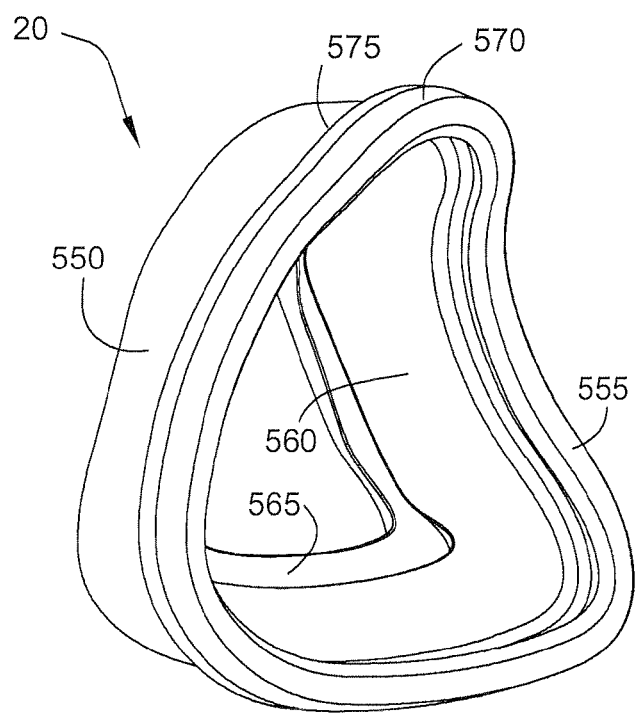
Figures 4, 10:
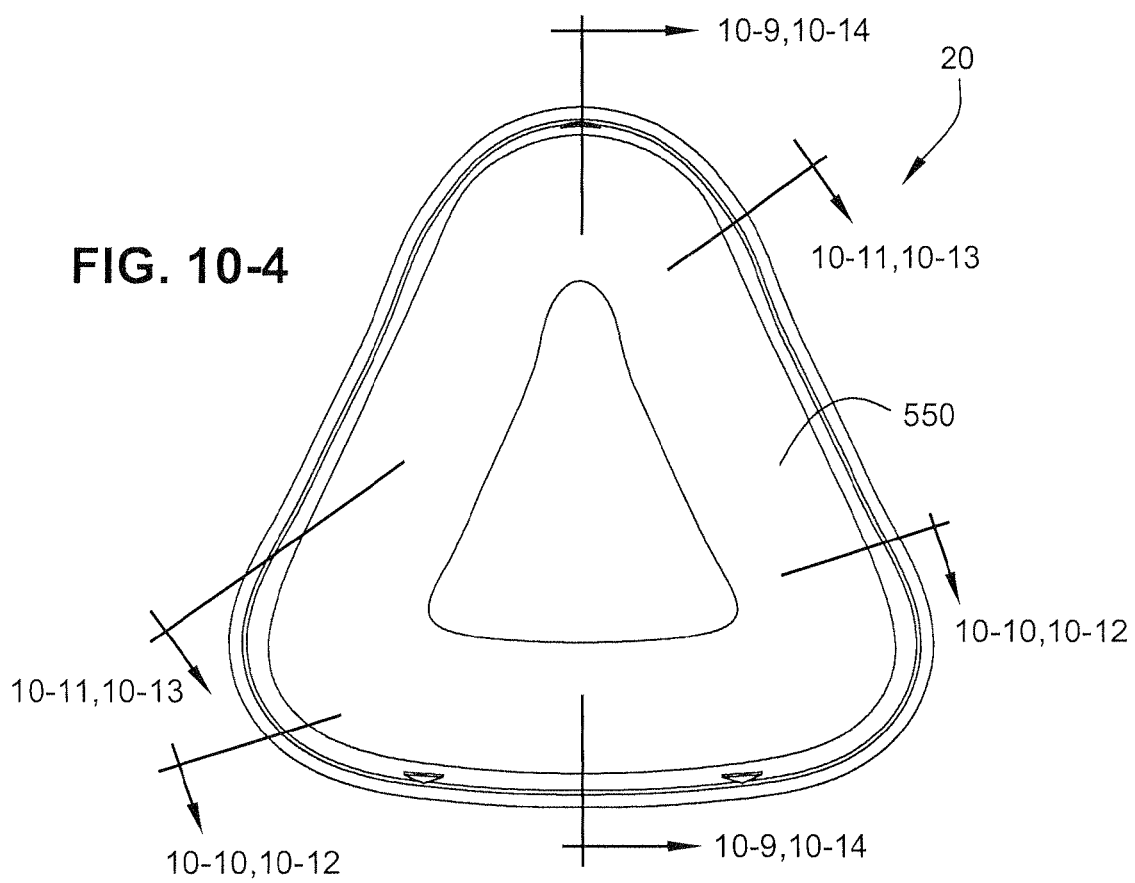
Figures 5, 10:
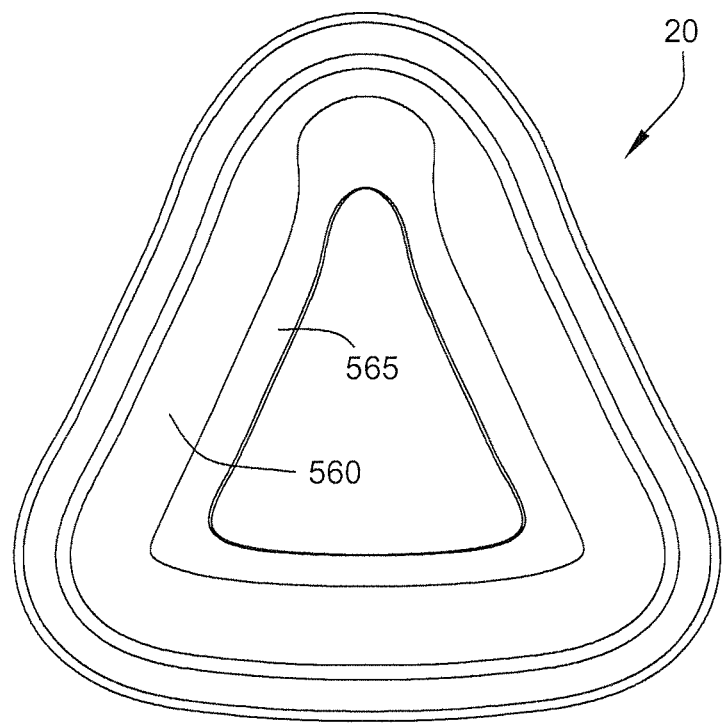
Figures 6, 10:
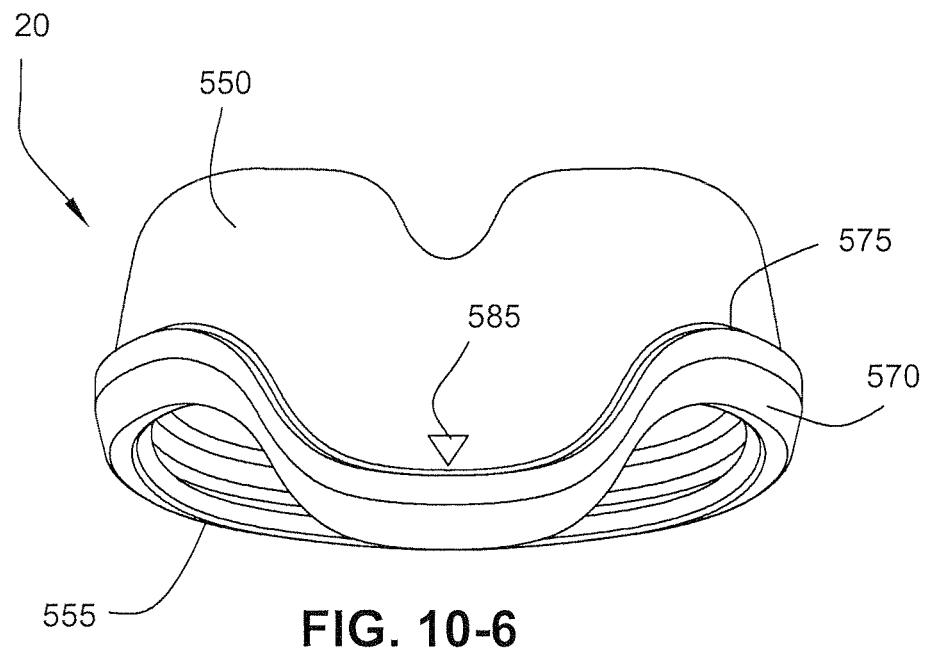
Figures 7, 10:
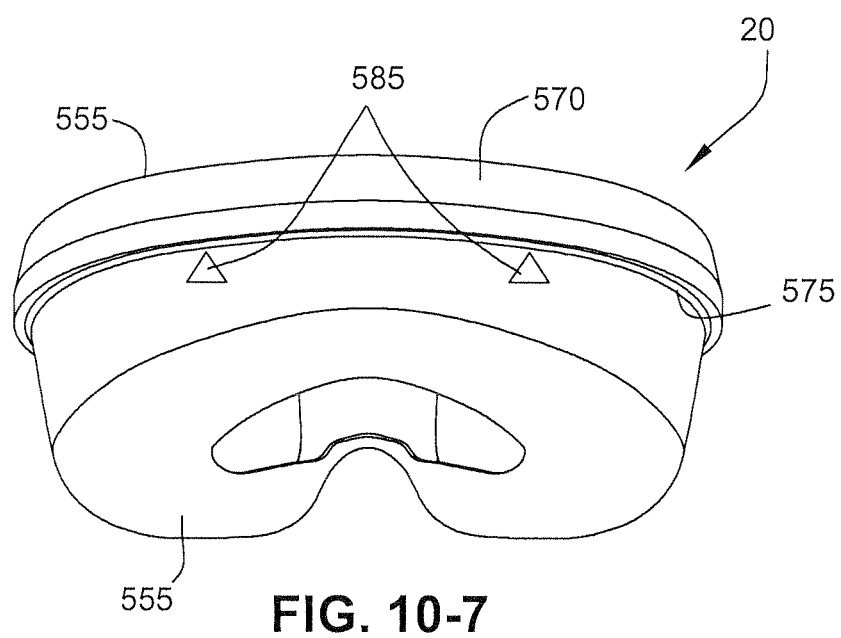
Figures 8, 10:
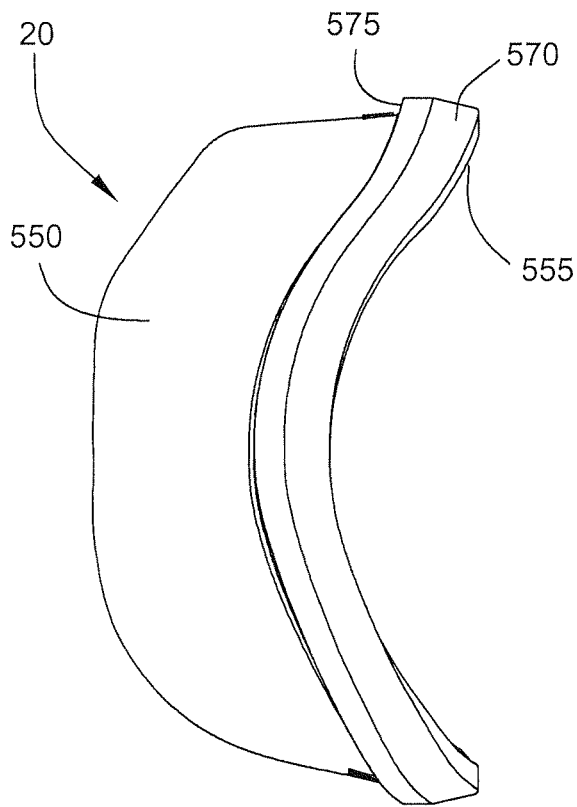
Figures 9, 10:
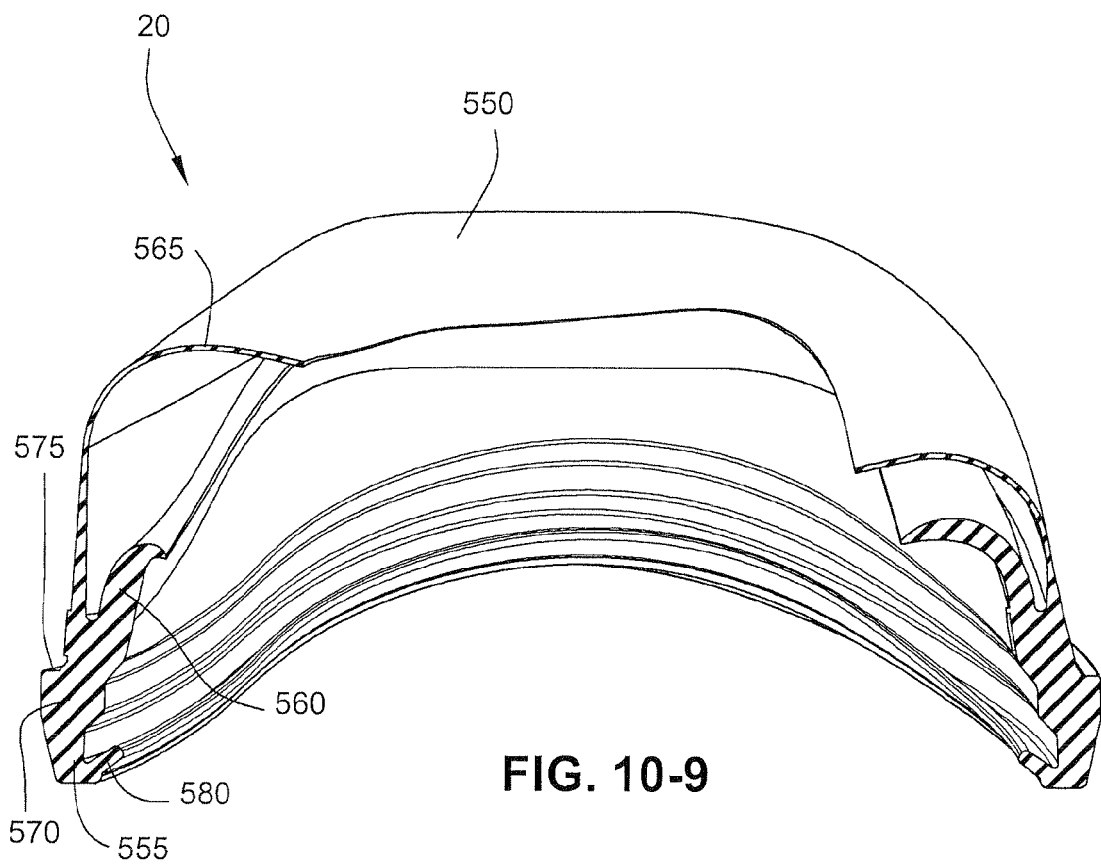
Figure 10:
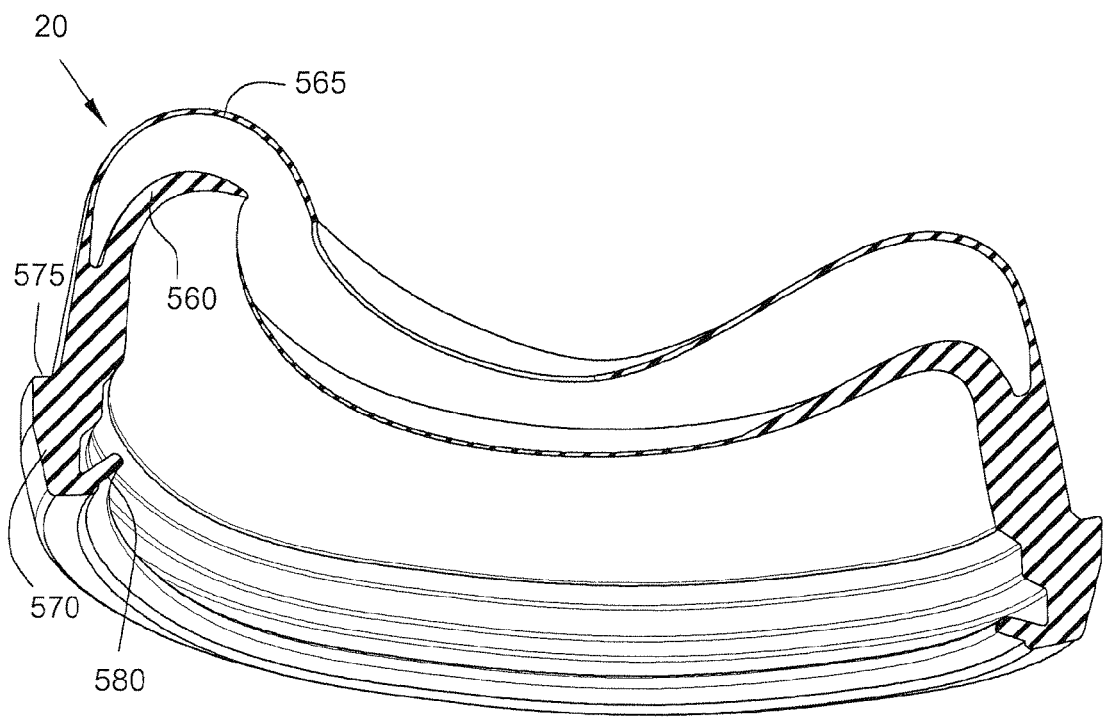
Figures 10, 11:
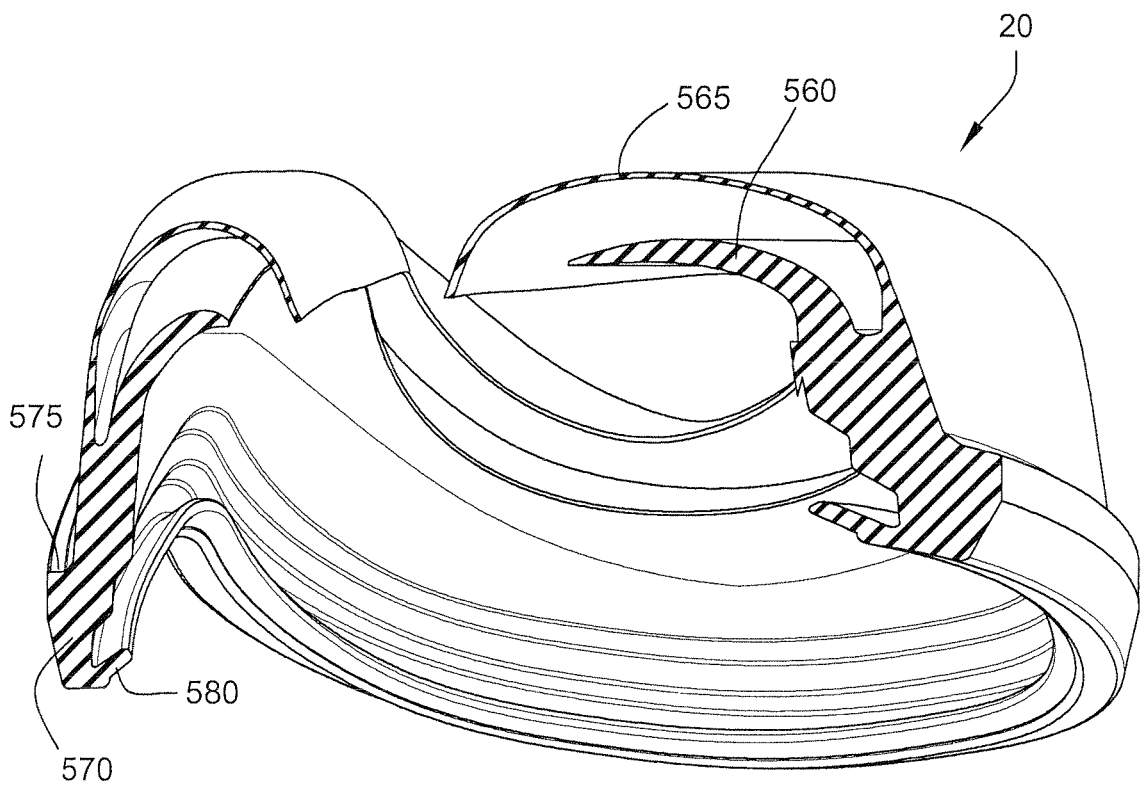
Figures 10, 11, 12:
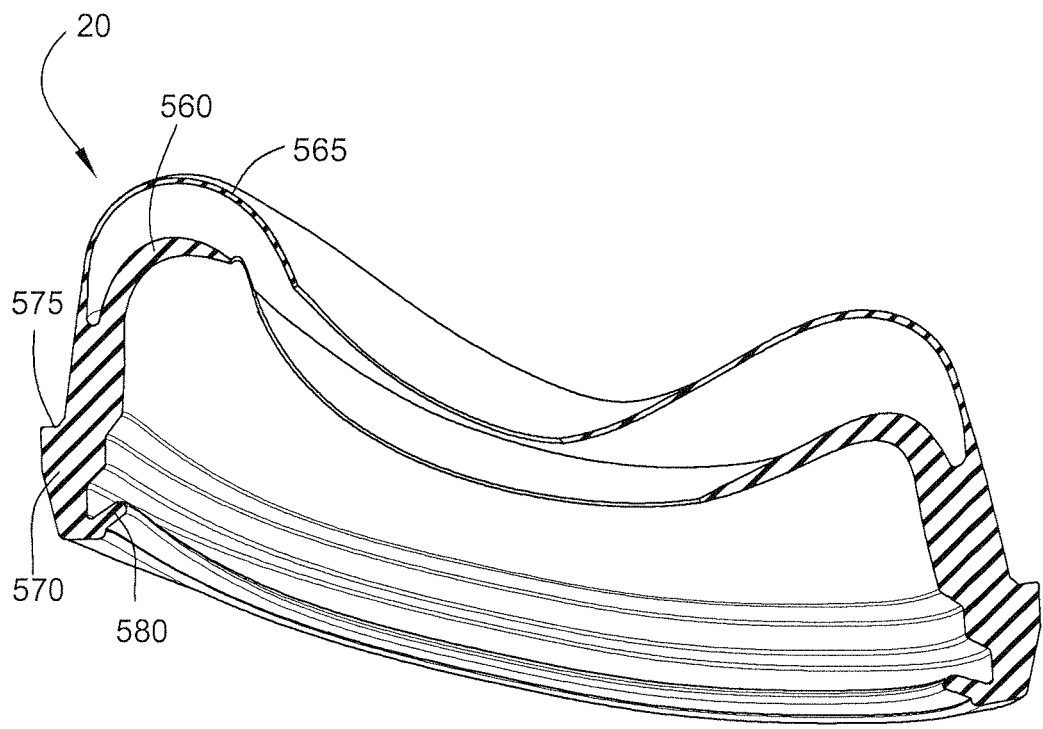
Figures 10, 11, 12, 13:
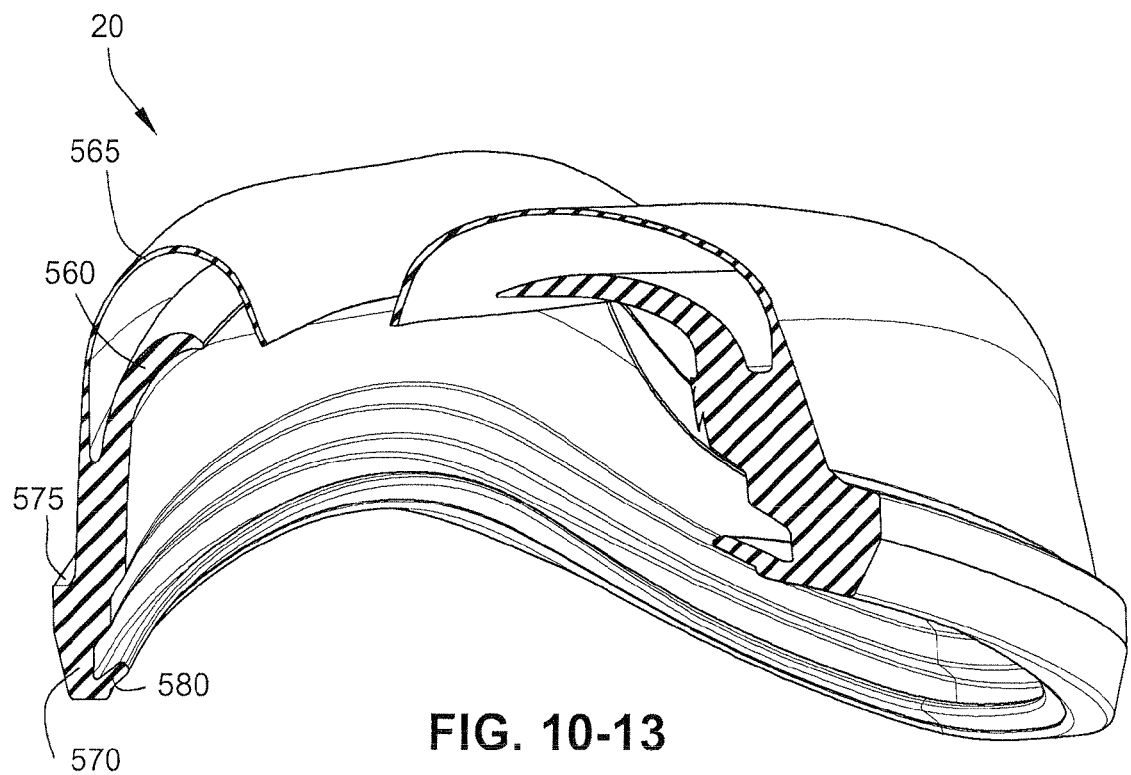
Figures 10, 11, 12, 13, 14:
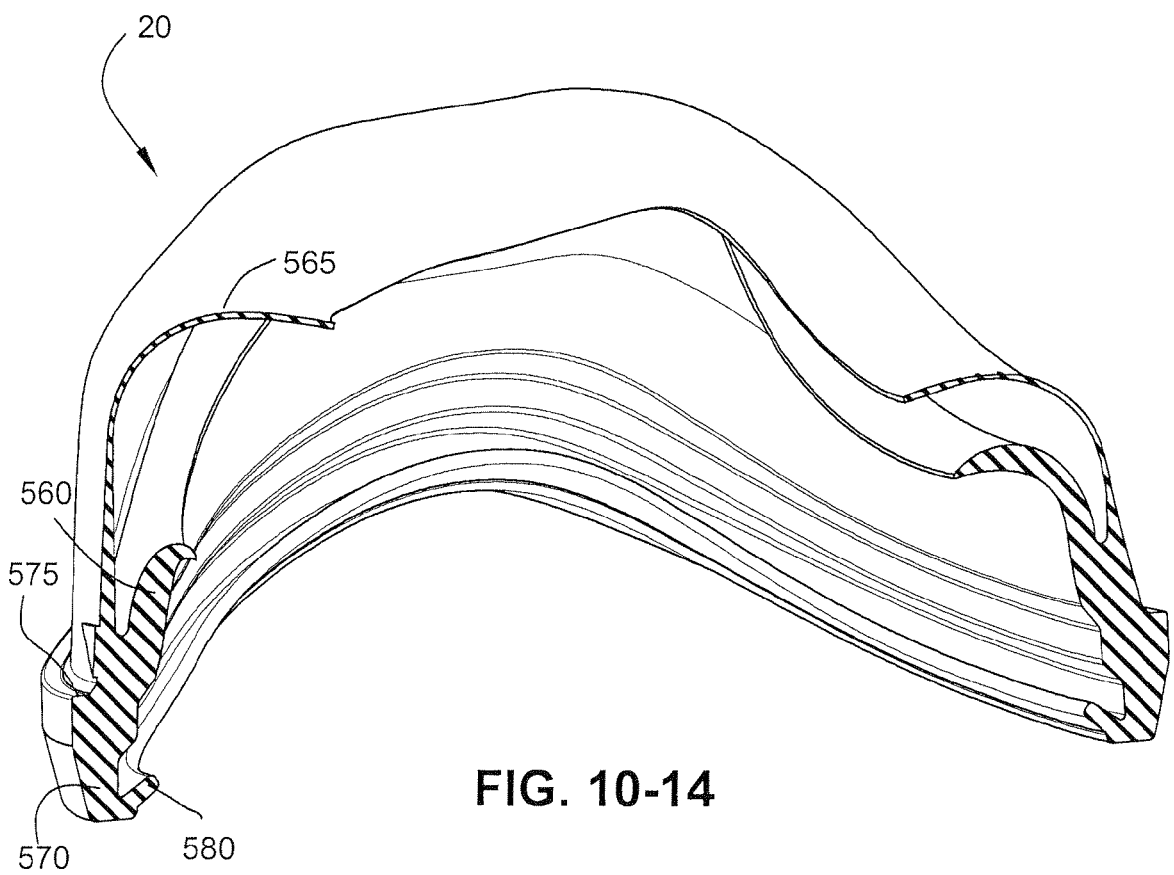
Figures 1, 11:
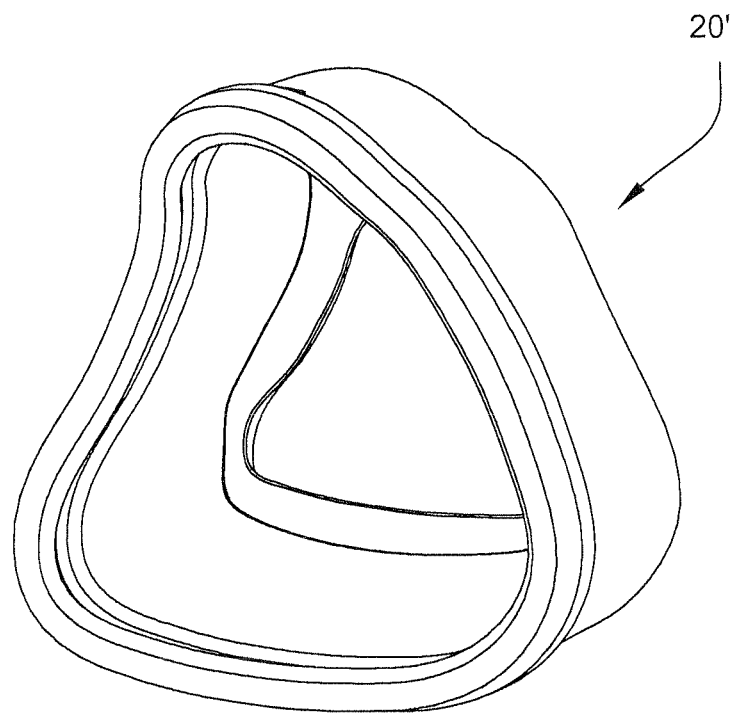
Figures 2, 11:
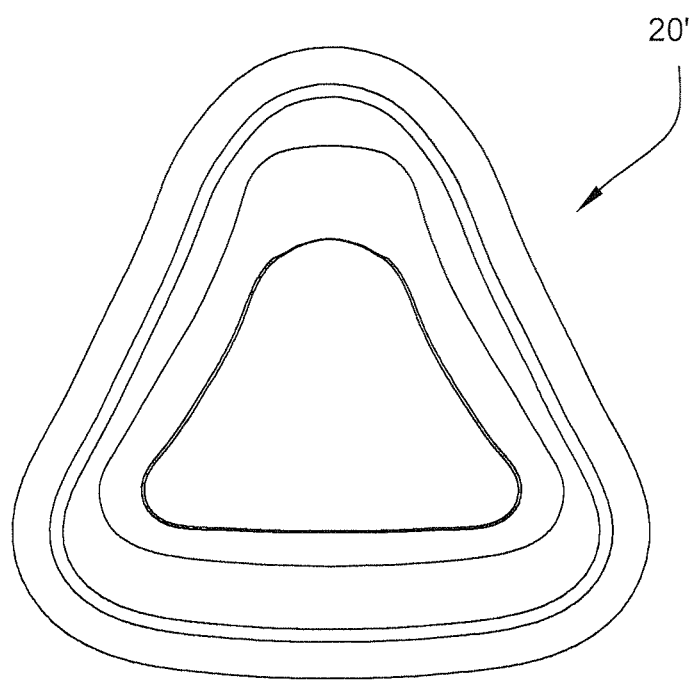
Figures 3, 11:
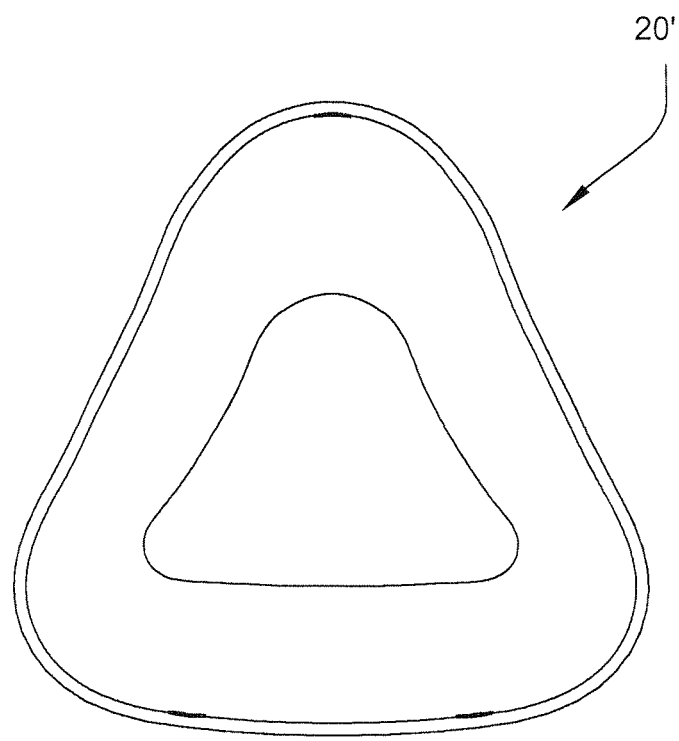
Figures 4, 11:
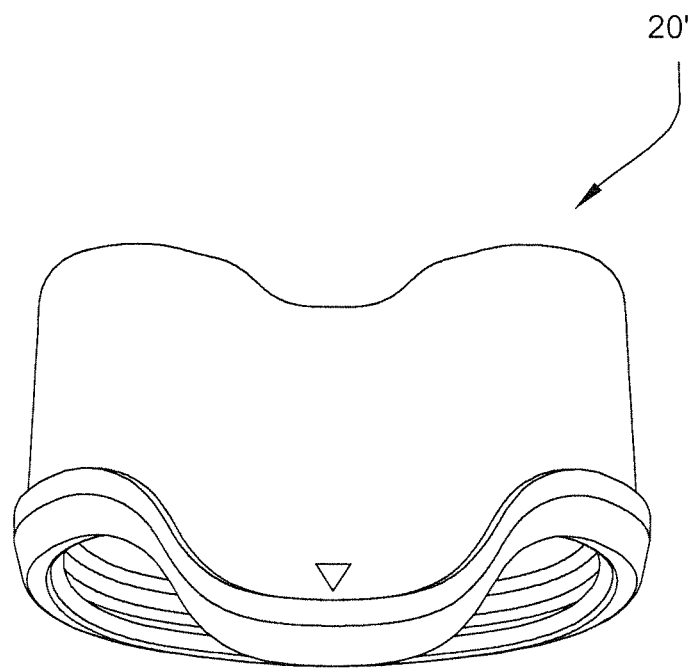
Figures 5, 11:
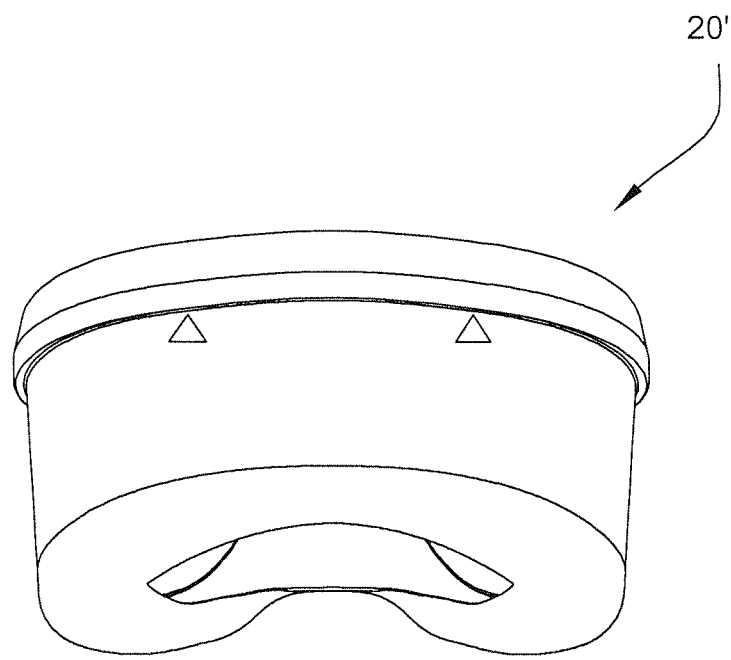
Figures 6, 11:
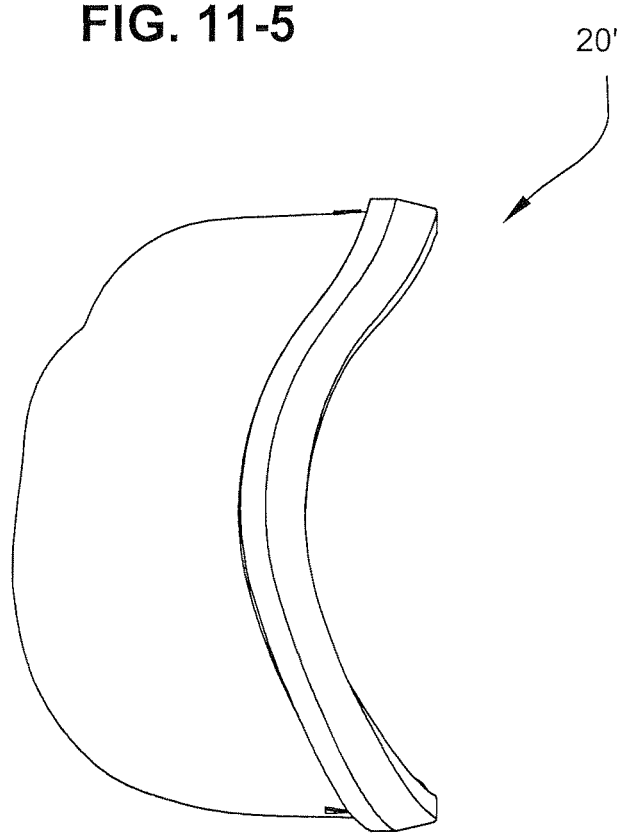
Figures 1, 12:
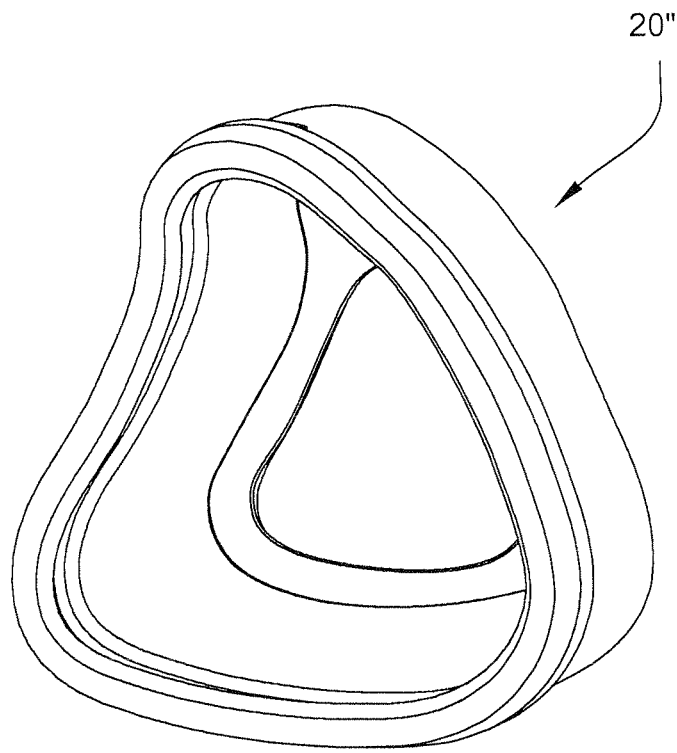
Figures 2, 12:
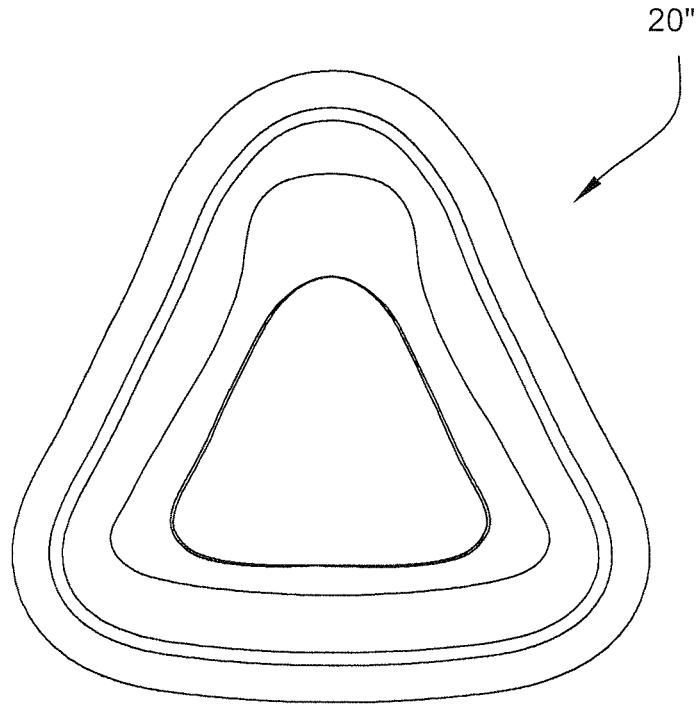
Figures 3, 12:
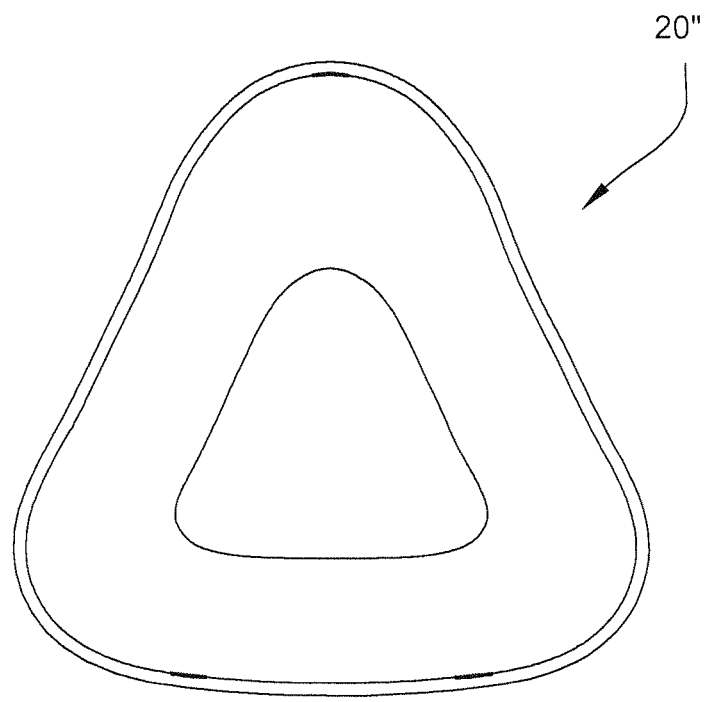
Figures 4, 12:
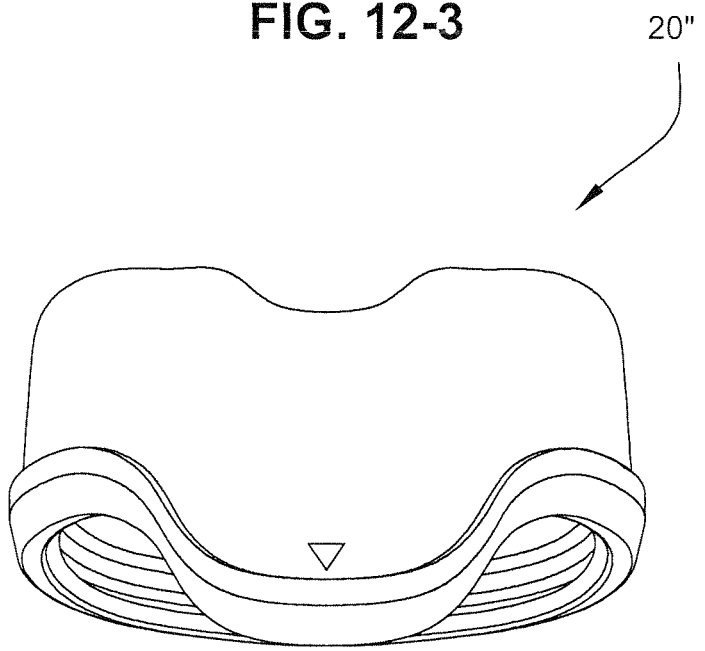
Figures 5, 12:
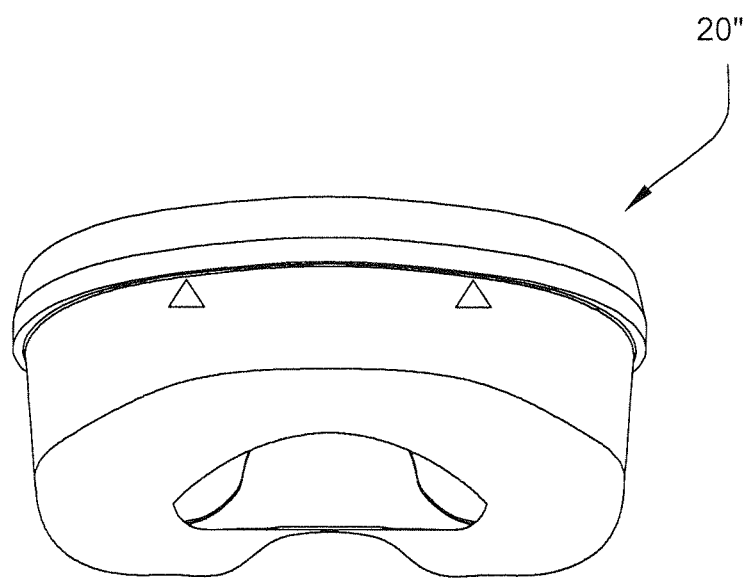
Figures 6, 12:
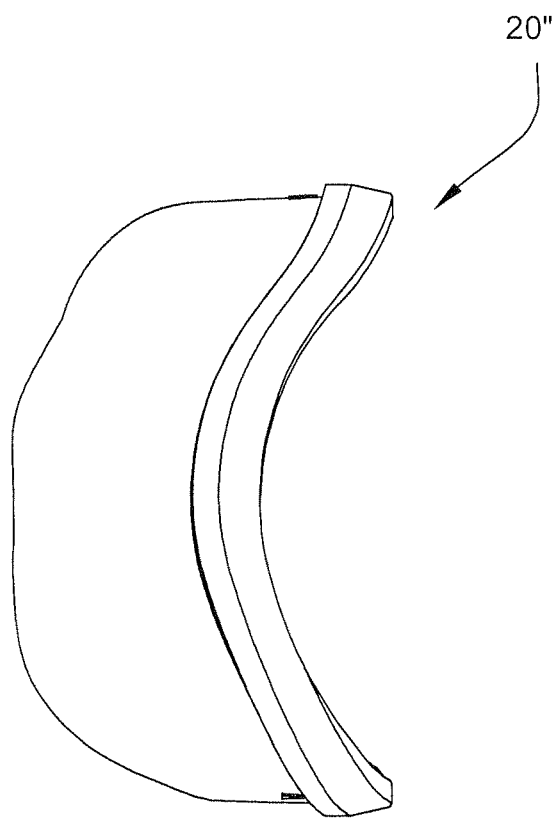
Figures 1, 13:
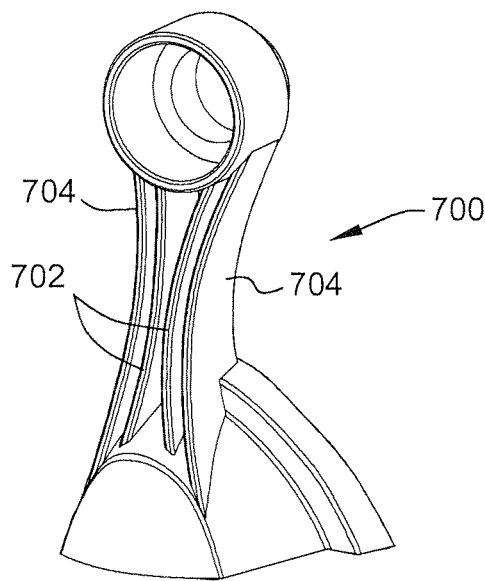
Figures 2, 13:
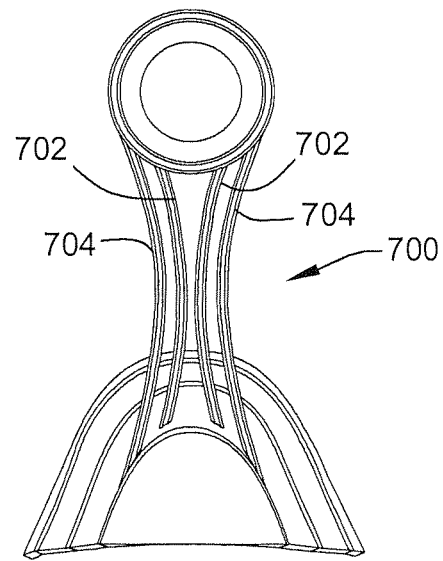
Figures 3, 13:
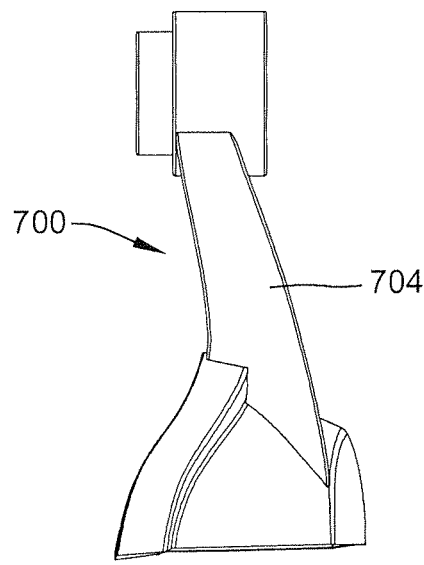
Figures 4, 13:
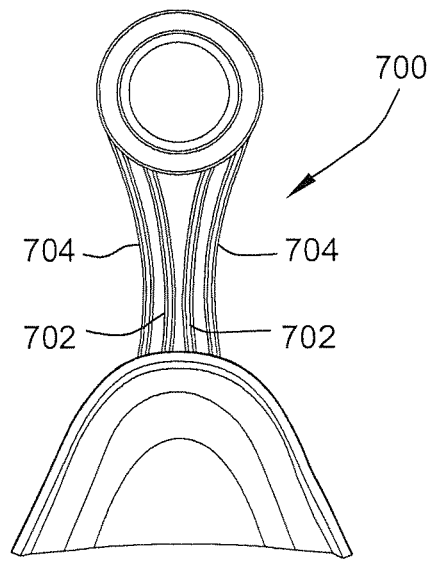
Figures 1, 14:
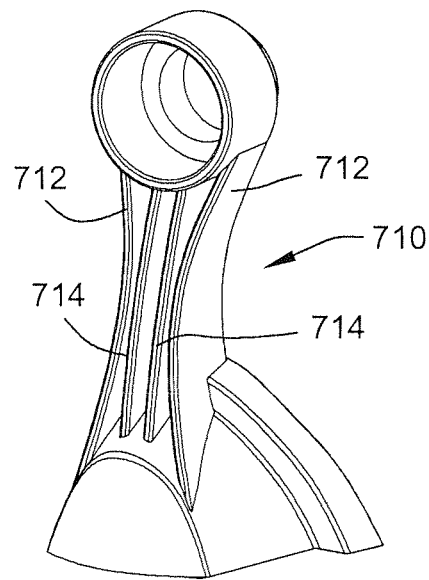
Figures 2, 14:
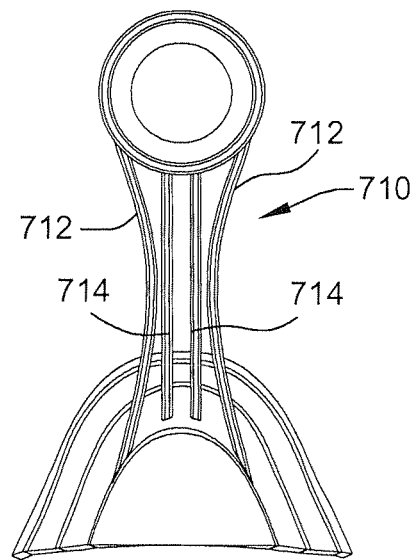
Figures 3, 14:
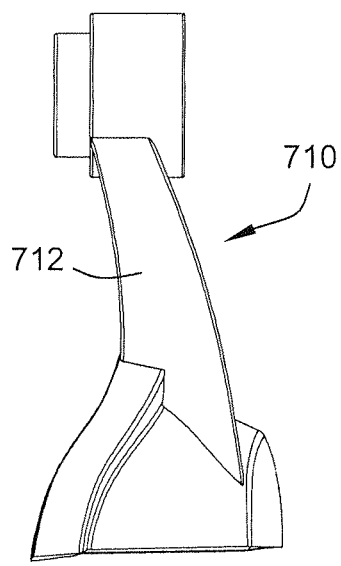
Figures 4, 14:
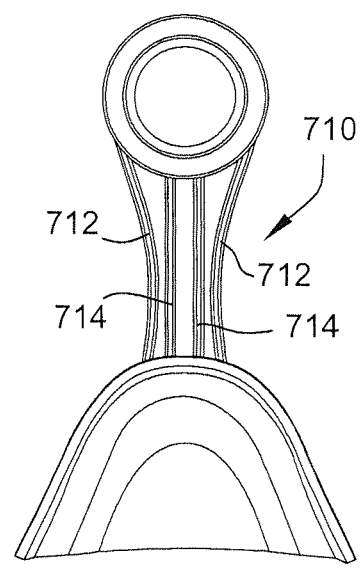
Figures 1, 15:
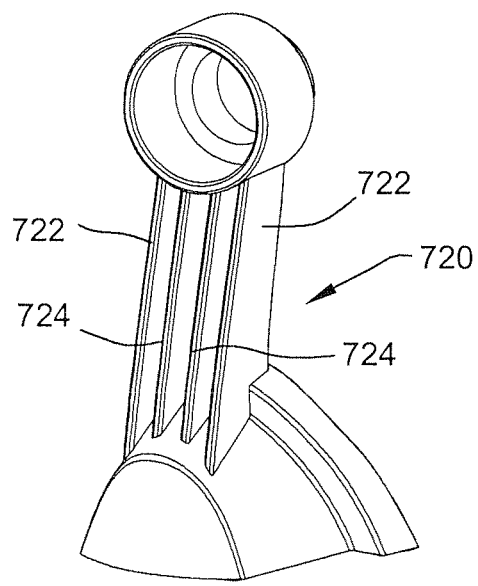
Figures 2, 15:
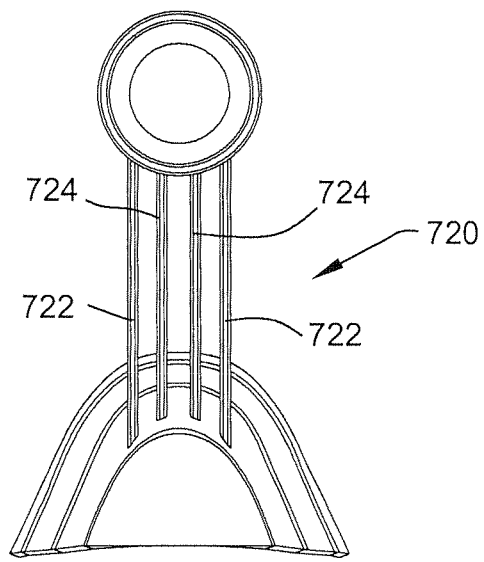
Figures 3, 15:
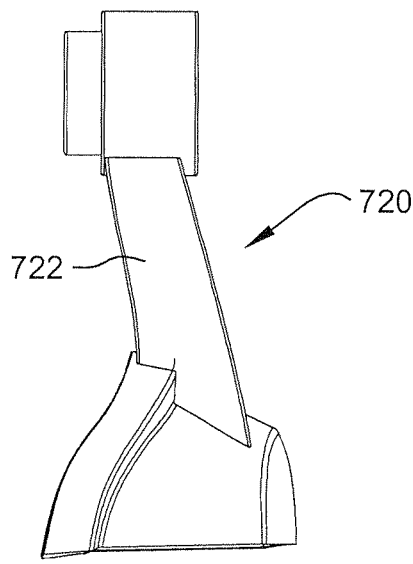
Figures 4, 15:
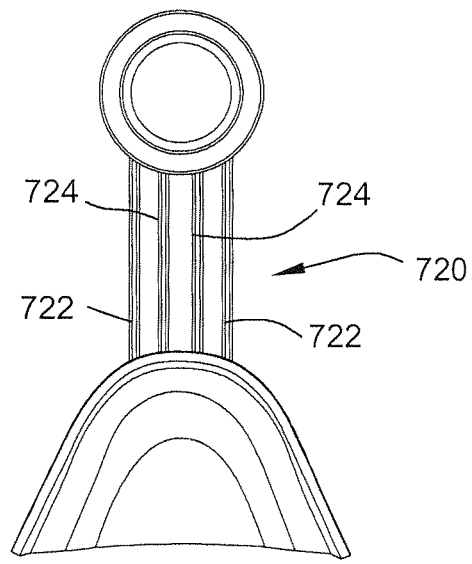
Figures 1, 16:
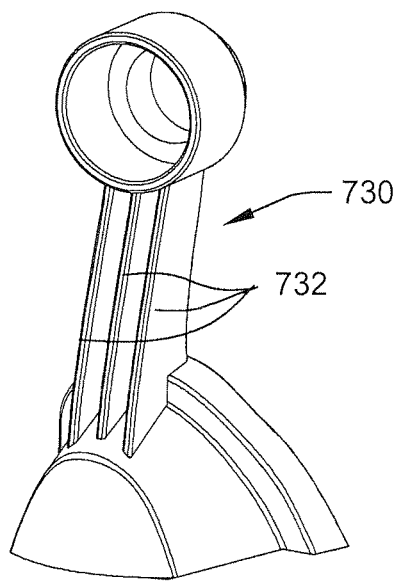
Figures 2, 16:
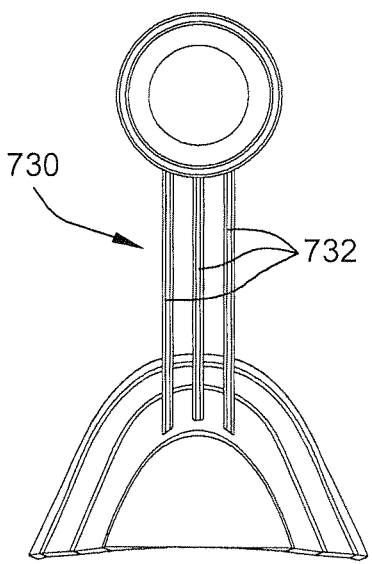
Figures 3, 16:
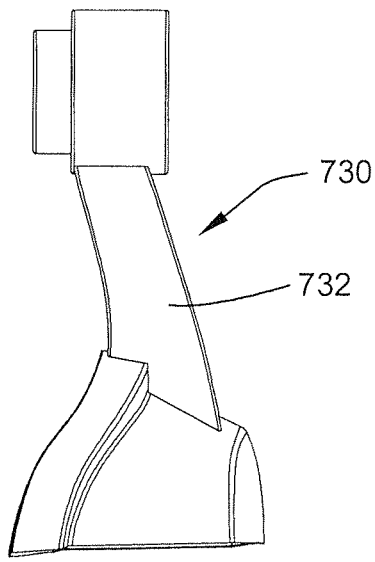
Figures 4, 16:
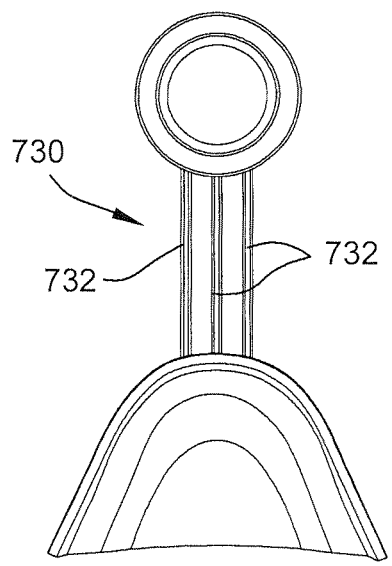
Figures 1, 17:
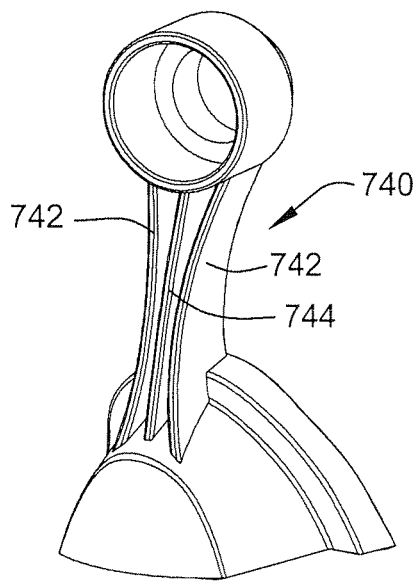
Figures 2, 17:
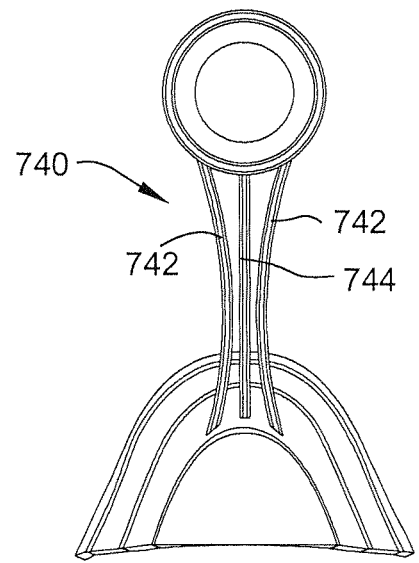
Figures 3, 17:
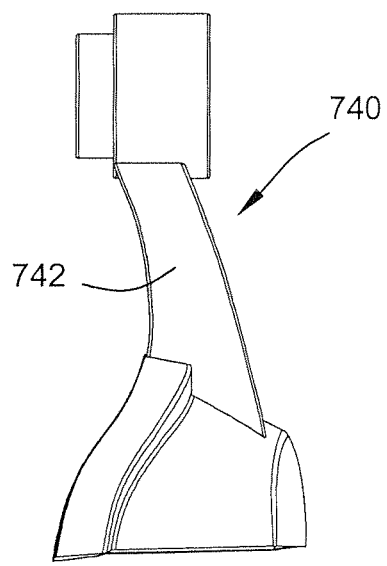
Figures 4, 17:
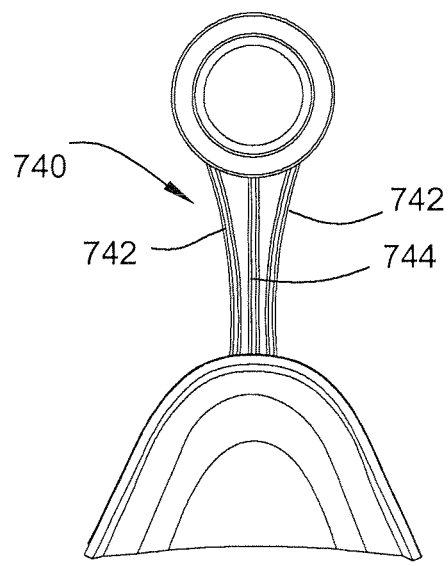
Figures 1, 18:
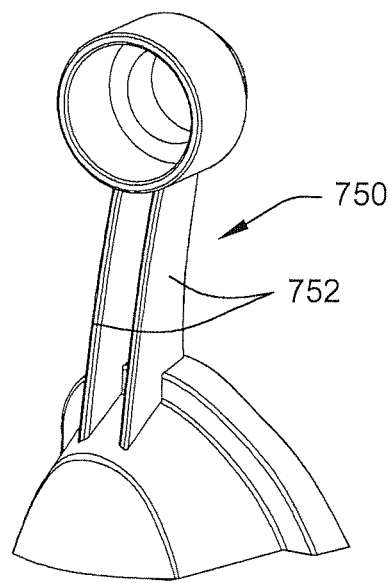
Figures 2, 18:
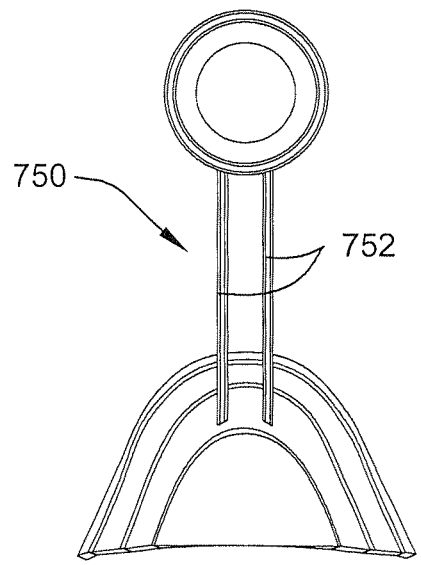
Figures 3, 18:
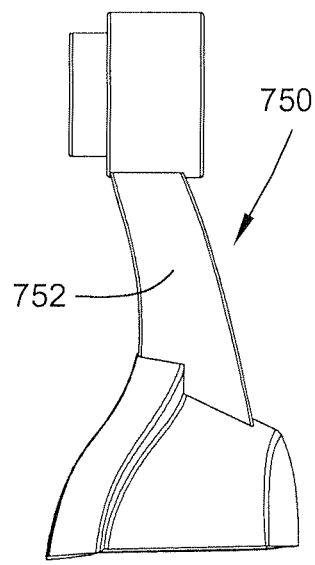
Figures 4, 18:
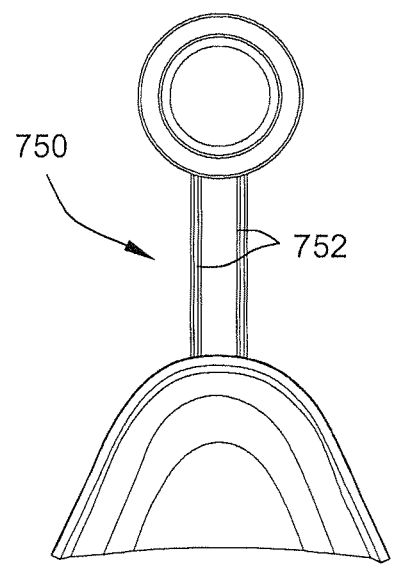
Figures 1, 19:
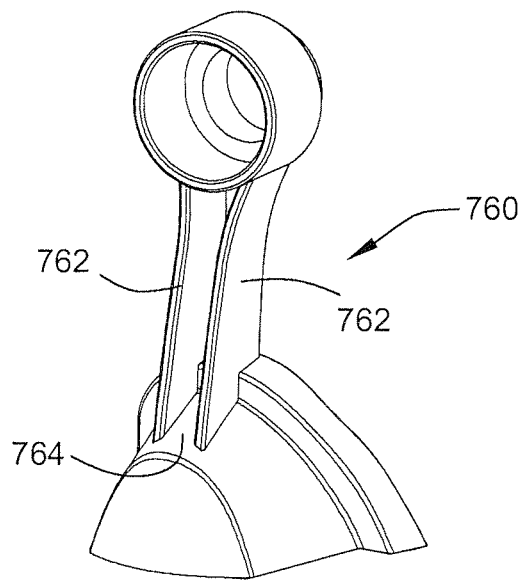
Figures 2, 19:
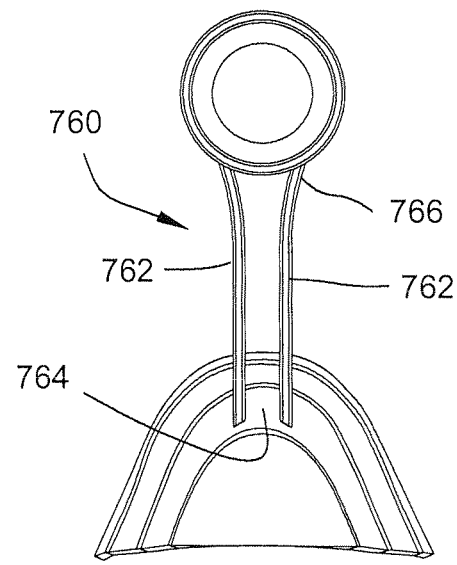
Figures 3, 19:
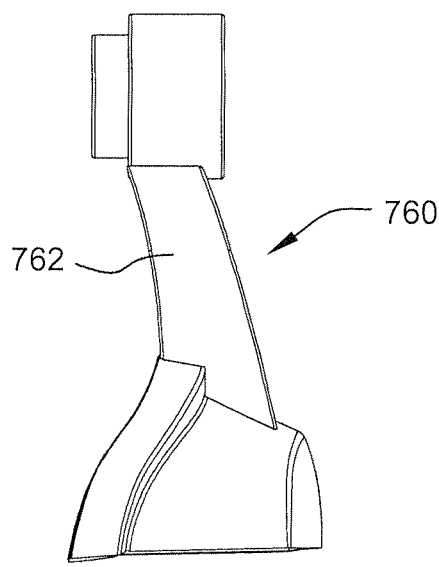
Figures 4, 19:
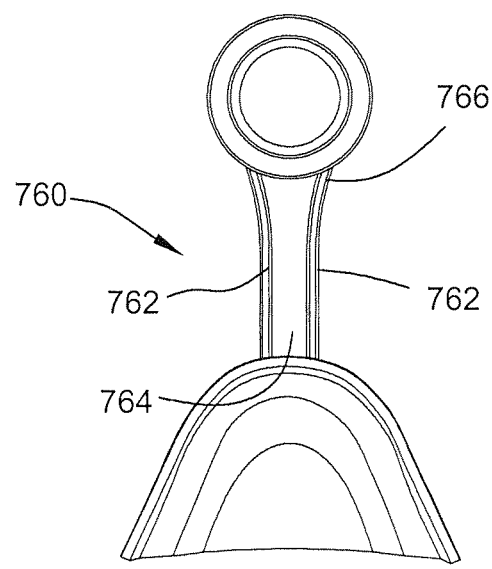
Figures 1, 20:
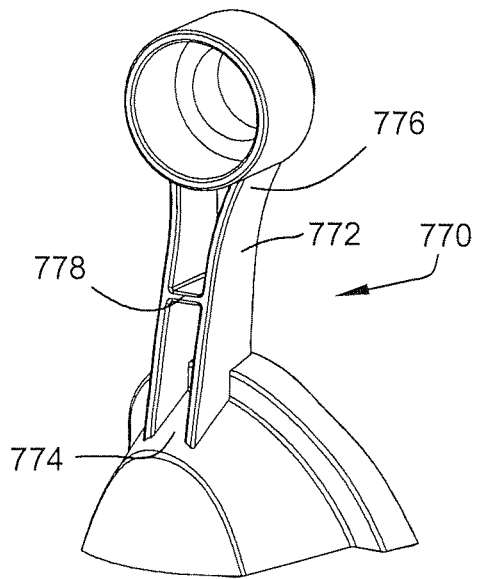
Figures 2, 20:
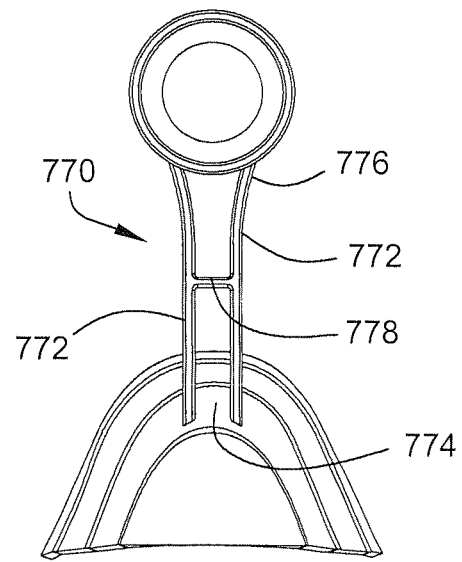
Figures 3, 20:
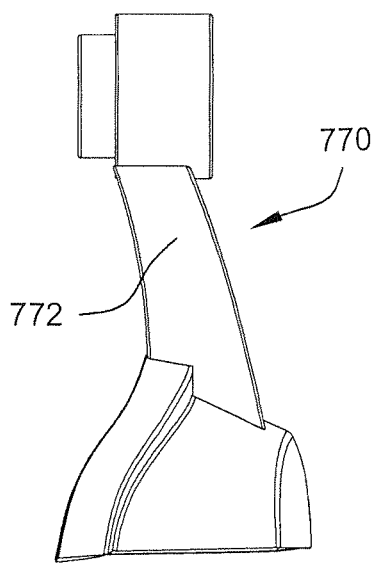
Figures 4, 20:
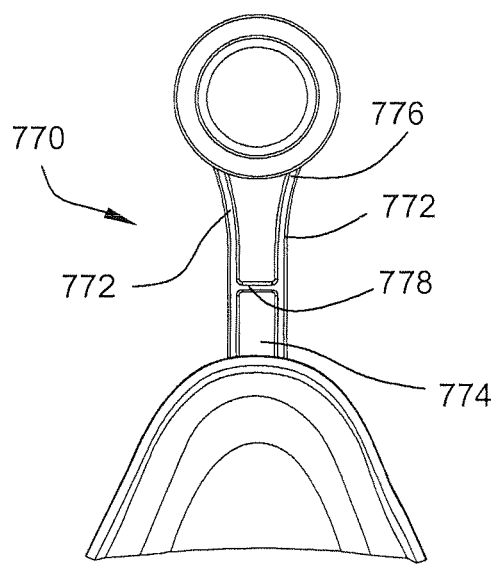
Figures 1, 22:
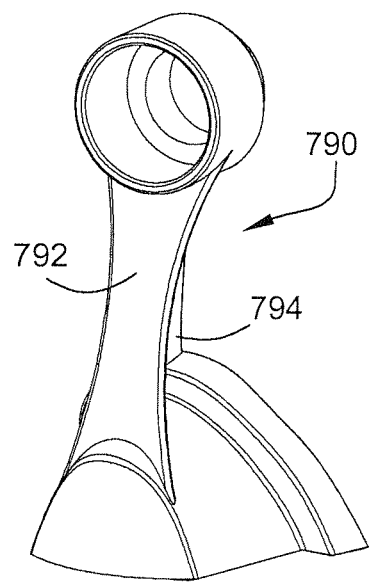
Figures 2, 22:
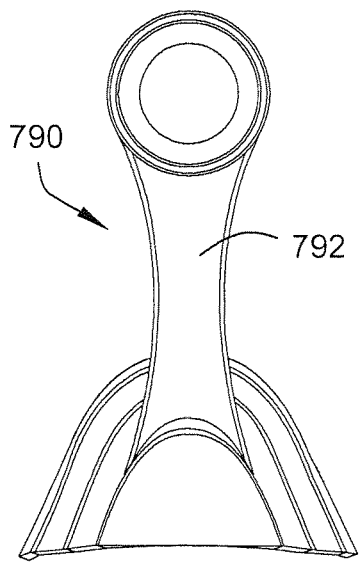
Figures 3, 22:
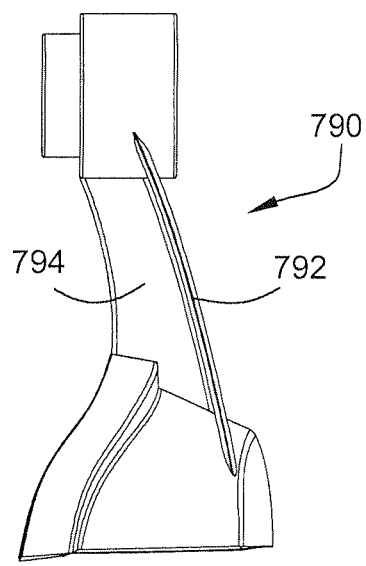
Figures 4, 22:
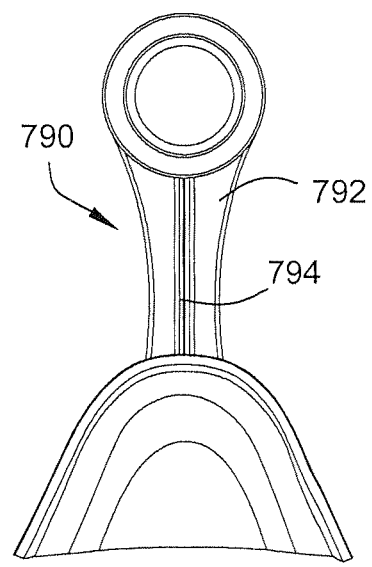
Figures 1, 2, 23:
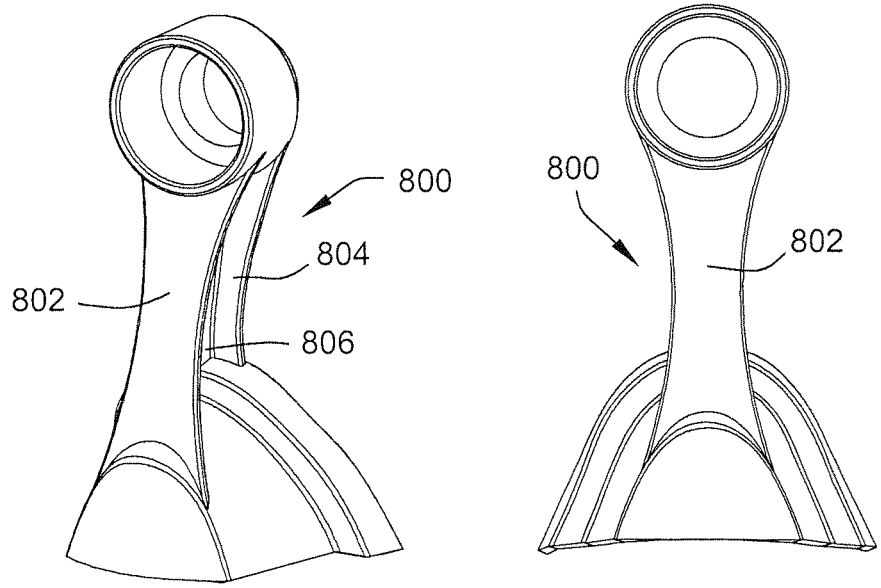
Figures 3, 4, 23:
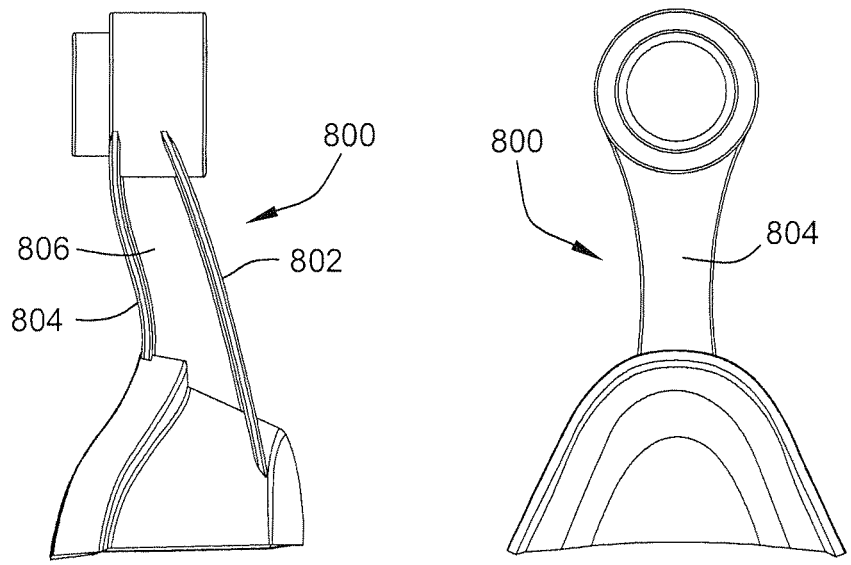
Figures 1, 24:
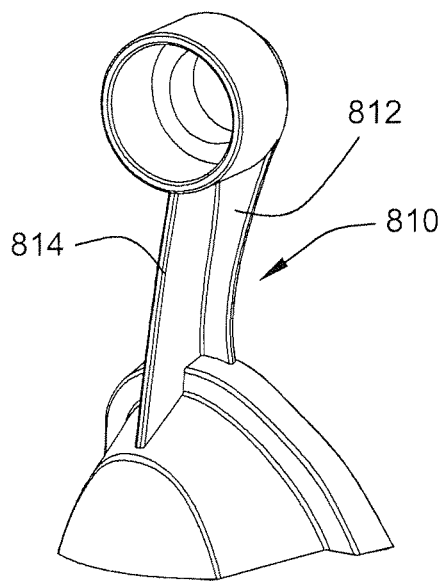
Figures 2, 24:
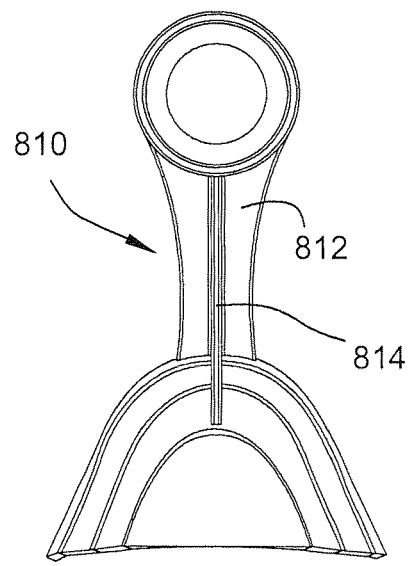
Figures 3, 24:
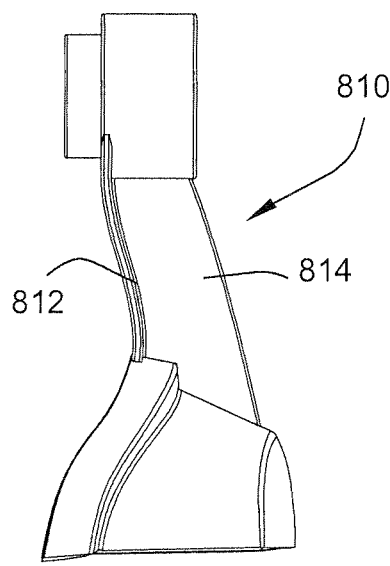
Figures 4, 24:
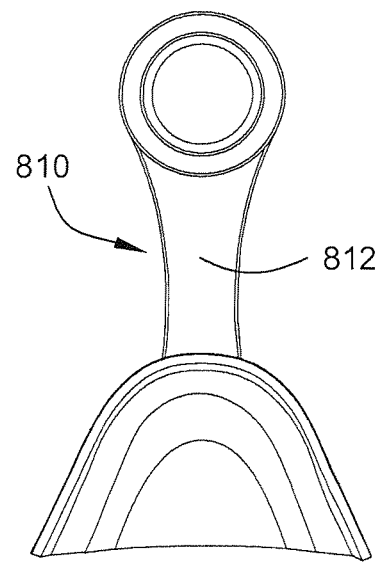

The spacing 182 between the side walls 170 is relatively narrow where the neck 165 overlies the bridge of the nose, or between the eyes. The shape and size of the neck portion 165 is such that it occupies the blind spot of the patient between the eyes, close to the face, which improves field of vision. As seen from FIGS. 2-2 and 2-3, the lower and upper ends 175, 180 of the neck 165 may diverge from one another so as to have a generally hour glass shape, with the narrowest portion 185 being between the eyes, as shown. The radius of curvature R of each side wall 170 is in the range of about 1-10 cm or about 5 cm. However, the side walls 170 may be parallel to one another, their ends may converge towards one another, or the side walls 170 may have a complex or compound shape which is part parallel, part converging and/or part diverging. It is also possible that neck 165 has more than two walls, or that it includes only one wall having a variable thickness and/or width. FIGS. 13-1 to 24-4 illustrate alternative variants of the neck, in which: FIGS. 13-1 to 13-4 show a neck 700 with two curved inner walls 702 and two curved outer walls 704; FIGS. 14-1 to 14-4 show a neck 710 with two curved outer walls 712 and two parallel inner walls 714; FIGS. 15-1 to 15-4 show a neck 720 with two parallel outer walls 722 and two parallel inner walls 724; FIGS. 16-1 to 16-4 show a neck 730 with three parallel walls 732; FIGS. 17-1 to 17-4 show a neck 740 with two curved outer walls 742 and a single linear inner wall 744; FIGS. 18-1 to 18-4 show a neck 750 with two parallel walls 752; FIGS. 19-1 to 19-4 show a neck 760 with two parallel walls 762 that are parallel at the bottom end 764 and diverge away from one another at the top end 766; FIGS. 20-1 to 20-4 show a neck 770 with two walls 772 that are parallel at the bottom end 774 and diverge from one another at the top end 776, wherein the walls 772 are interconnected by one or more linear cross bars 778; FIGS. 21-1 to 21-4 show a neck 780 with two generally parallel walls 782 that diverge from one another at the top end 784 and which includes two or more curved cross bars 786; FIGS. 22-1 to 22-4 show a T-shaped neck 790 having a front wall 792 forming the cross of the T and a rear wall 794 forming the stem of the T; FIGS. 23-1 to 23-4 show a neck 800 having a generally I-shaped cross section having a front wall section 802 forming the upper cross of the I, a rear wall 804 forming the lower cross of the I, and a middle wall section 806 forming the interconnecting leg of the I between the front and rear walls; and FIGS. 24-1 to 24-4 show a neck 810 having a generally T-shape with a rear wall 812 forming the cross of the T and a front wall 814 forming the stem of the T.

2.3.2 Flowing, Sweeping Design

Neck 165 has a streamlined, flowing, sweeping design that blends well and has a continuous form with other parts of the mask. For example, as seen in FIG. 2-6, the front edge 190 and rear edge 195 of the sides walls 170 converge in an upward direction from the apex 155 to the forehead support assembly 25. However, the front and rear edges 190, 195 may be parallel or diverge in direction, or they may have a compound shape that is part parallel, part converging, part diverging, etc.

As seen in FIG. 2-6, the rear edge 195 of the side wall 170 joins to the rear edge 200 of the lower portion 45, and the front edge 190 of the side wall joins to the front wall 205 of the frame lower portion 45 in a smooth, congruous manner that provides a sleek appearance without sharp edges that may snag. The front edges 190 of side walls 170 are substantially continuous with the upper edge 46 (FIG. 2-1) of lower portion 45 which surrounds front wall 205. The upper ends 180 of the side walls 170, best seen in FIGS. 2-1 to 2-3 and 3-1, diverge and are joined to a main support ring 310 of the forehead support assembly 25 (FIG. 1-1) in a congruous, smooth manner as well.

Front edge 190 of each side wall 170 includes a radiussed curvature 210, as best seen in FIGS. 2-1 and 2-6. This provides for extra strength and eliminates sharp edges.

2.4 Headgear Clip Receptacles

As seen in FIGS. 2-1 and 2-6, frame 10 includes a guide structure 215 provided adjacent each clip receptacle 35 for the purpose of guiding each clip 30 into position upon assembly of the clip with the clip receptacle 35. Clips 30 (FIG. 1-1) are described in U.S. Pat. No. 6,374,826, incorporated herein by reference in its entirety. Guide structure 215 includes one or more ramped surfaces 220, two are shown in the example drawings, which are shaped to guide the leading end of the clip into the receptacle 35. Ramped surfaces 220 (or ribs) extend from or between the bottom side 225 of each receptacle and the top surface 230 of the frame, near the perimeter edge, as seen in FIG. 2-4 and FIG. 2-6. In this way, insertion of the clip 30 into the receptacle 35 can be ensured even if the leading edge of the clip 30 first contacts the side wall 235 of the frame 10 along the perimeter. This avoids snagging of the leading end below the lower wall or edge of the receptacle 35.

2.5 Channel

Figures 1, 2, 3:
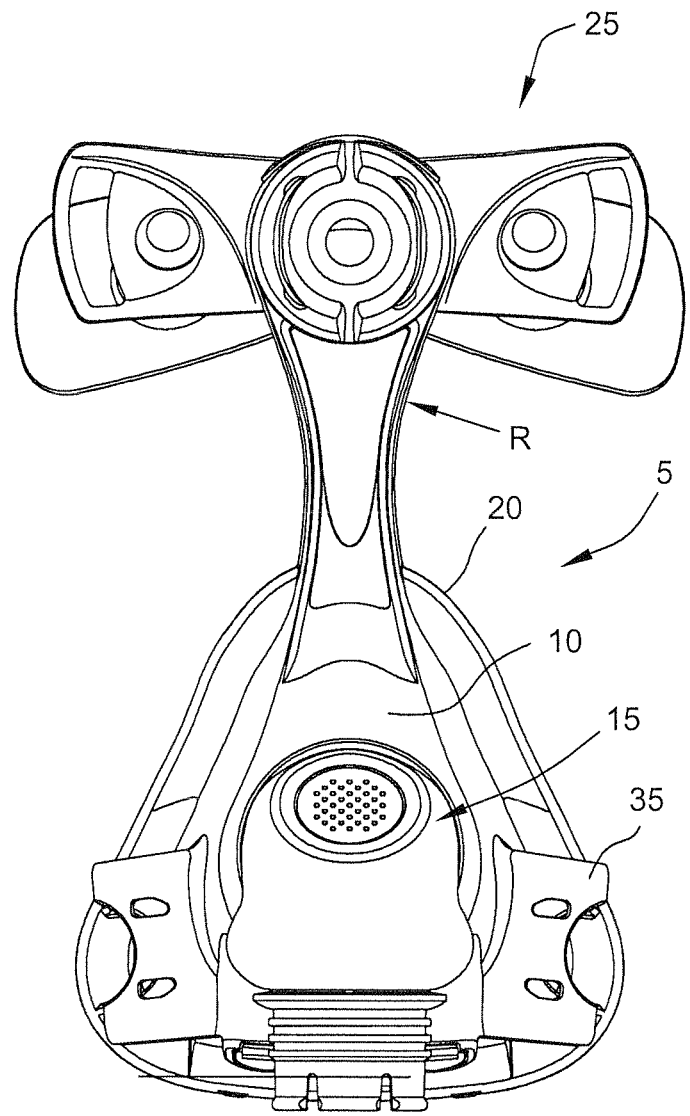
Figures 1, 2, 3, 4:
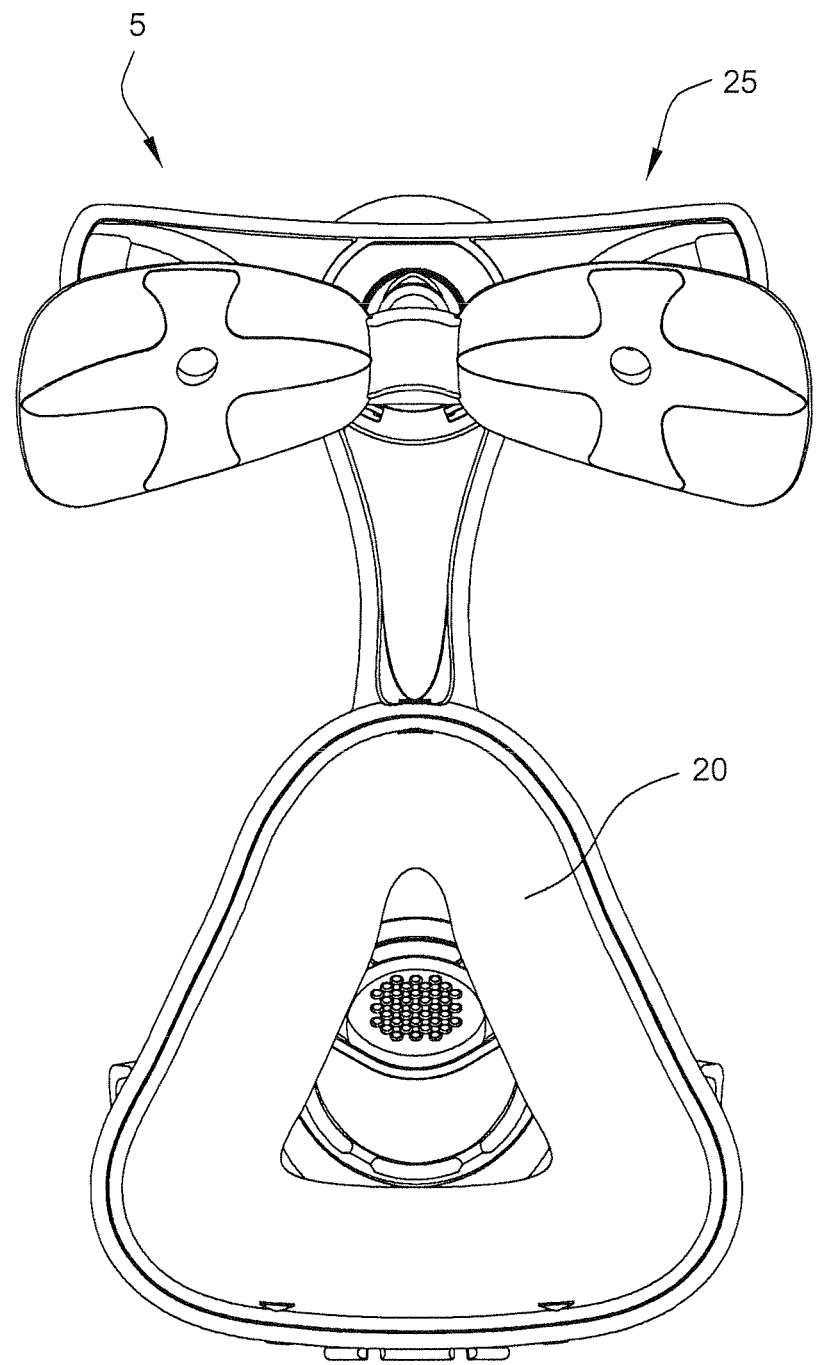

As shown in FIG. 2-3, frame includes a channel 240 to receive cushion. Channel 240 is formed by an outer wall 245 and an inner wall 250. As shown in FIGS. 2-2 and 2-3, the frame 10 may include a hole 267, for example in the bottom wall 275 of the channel 240. The hole 267 allows vacuum pressure to be applied to attach the cushion 20 to the frame 10 during manufacturing. The hole 267 also permits air to be expelled from the channel 240 during assembly of the cushion 20 to the frame 10 to ease insertion of the sidewall of the cushion 20 into the channel 240.

2.5.1 Channel Bead

Channel, e.g., inner wall 250 or outer wall 245, includes an inner surface (facing towards channel) having a bead 255 to engage with an outer surface of the edge of the cushion 20. The edge forms a "tongue" of a tongue and groove arrangement. In the example shown, bead is provided on inner wall 250. Bead 255 preferably only extends around a portion of the perimeter of the surface of the inner or outer wall facing the channel 240. For example, as shown in FIG. 2-3, bead 255 does not extend in one or more corners 260 of the channel 240 or inner wall in the illustrated example, but instead extends only along the relatively more straight or linear portions 265 of the channel or inner wall 250, or a portion of the linear portion of the channel 240. This feature has a manufacturing advantage whereby the tooling for the molding equipment can be more easily removed from the channel after molding. The reduced length bead also may help reduce the force to insert the cushion into and remove the cushion from the channel.

Cushion 20 and channel 240 form a basic tongue and groove coupling arrangement by which cushion 20 is maintained in sealed connection with frame without the need for an additional retention mechanism, such as an overclip as described in U.S. Pat. No. 6,412,487, incorporated herein by reference in its entirety. Although the tongue and groove arrangement forms both a seal and a retention mechanism, additional retention mechanisms could be employed as well, such as glue, and overclip, etc.

Channel walls 245, 250 may be parallel, or they may be angled (up to about 10°, or from 1°-5°, or 1°-2°) so as to facilitate insertion and to provide sufficient retention of the cushion 20 with the frame 10 once assembled.

It should be appreciated that the channel 240 can be formed in the cushion 20 and the tongue portion formed on the frame 10. Also, the bead 255 could be provided along the entire perimeter of the inner and/or outer walls, or the bead can be provided only along certain portions thereof, e.g., corners, linear portions. In a variant, the bead can be provided along a portion of the outer wall and another portion of the inner wall, in alternating fashion, or the bead can be provided to both walls. In another variant, the bead 255 may be split as shown in FIG. 10-2.

2.5.2 Channel Rib

As shown in FIG. 2-3, channel includes one or more ribs 270 along the bottom wall of channel 240 for reasons relating to "core out" during the manufacturing process. Side cores to produce the clip receptacle can result in thickening of the wall sections due to draft surfaces. The channel and ribs ensure uniform wall sections and provide a base for cushion assembly while avoiding sink marks on the top surface. Each rib 270 may extend between the inner and outer walls 245, 250 and is shown in this example along the side and base portions of a bottom wall 275 of the channel. Each rib 270 is raised compared to the surface of the bottom wall 275.

3.0 Forehead Support and Pad Assembly

FIG. 3-1 shows forehead support assembly 25 in an exploded condition relative to frame, while FIGS. 3-2 to 3-8 show a forehead support 300 and a pad 305 in isolation. FIGS. 4-1 to 4-6 show the forehead support 300 in isolation.

3.1 Adjustable

Forehead support 300 is linearly adjustable relative to ring support 310, which is supported by the neck 165. Specifically, the forehead support 300 includes a main body 315 with a split ring cantilevered member 320 that extends through ring support 310 and is engagable with an adjustment dial or knob 325 which includes a threaded portion 330 to engage with an internal threaded portion 335 of the cantilevered member. Knob 325 includes a flange 340 that engages one or more claws 345 in the inside surface of ring 310 to maintain knob 325 in a connected yet rotatable position relative to the support ring. Knob 325 is rotatable to thus control the position of the forehead support 300. During rotation, a biased follower 350 engages a ratcheted or undulating surface 355 to allow detented movement of the knob 325 relative to the support ring in a number of discrete positions, as described in WO 2007/143793 A1, incorporated herein by reference in its entirety. Support ring 310 includes a cut out notch 360 (see FIGS. 1-5 and 3-1) by which the patient can insert his or her finger to ensure separation between the forehead support 300 and the support ring 310.

The position of the adjustment mechanism is near or at the upper ends 180 of the neck 165 (FIG. 3-1), which thus positions the adjustment mechanism, e.g., knob, support ring, etc. over the patient's forehead and away from the eyes, thereby providing a clear line of sight for the patient.

3.2 Reduced Profile

A forehead pad 305 is provided to or otherwise connected to forehead support 300 using a pair of elastic support shafts 365 each including a head portion 370 resiliently squeezed into support holes 375 positioned on the main body 315 of the forehead support 300 (FIG. 3-8). FIGS. 1-1 to 1-7 and 3-1 to 3-8 show various views of the pad, which is also described in U.S. Patent Application Publication US 2004/0112387 A1, incorporated herein by reference in its entirety.

As shown in FIGS. 3-2 to 3-6, forehead support 300 has a (horizontal) length t that is less than the length of the pad 305. This is advantageous again from the perspective of reducing obtrusiveness to the patient since the overall size of the forehead assembly appears to be reduced. This feature additionally reduces potential for dislodging the mask when sleeping. At the same time the forces from the frame to the pad are still evenly distributed on the patient's forehead in use even though the forehead support is shorter.

3.3 Strap Slots

Each end of the forehead support 300 includes a slotted connector portion that provides a slot 380 to secure a headgear strap thereto (FIG. 4-1). Headgear strap may include a hook and loop fastener in which the leading hook end of the strap may be threaded through the slot, folded and fastened to the hook portion of the strap. In a variant, the ends of the forehead support 300 may be provided with receptacles to receive a clip like those shown in FIG. 1-1.

Each slot 380 is in the form of a closed loop, meaning that the slot 380 has no access from any side wall surrounding the slot 380. However, the slot 380 can be in the form of an open loop in which case it would not be necessary to disengage the hook from the loop to couple the strap to the forehead support 300.

Each slot 380 has a shape that is generally curved towards the shaft receiving hole 375 of the main body 315 of the forehead support 300. Each slot 380 is shaped so as to improve aesthetics. The curved slots assist in reducing the overall obtrusiveness of the design by directing the form inwards leading towards the frame. The slots incorporate curves and aesthetic features from other parts of the mask system to create a coherent aesthetic. In addition, the slots 380 are arranged so as to direct the strap vector in a direction which is comfortable and effective to maintain the mask in the correct orientation using headgear. Suitable headgear for mask is disclosed in U.S. Pat. No. 7,188,620, incorporated herein by reference in its entirety.

Furthermore, the main body 315 includes curved or arched walls 381 (FIG. 4-3) which facilitate manufacturing by helping material flow in the tool to make the part to specification. The arched walls 381 allow material to flow at a relative rate compared to the ends of the split shaft 320.

4.0 Elbow Assembly

Figures 1, 2, 3, 4, 5:
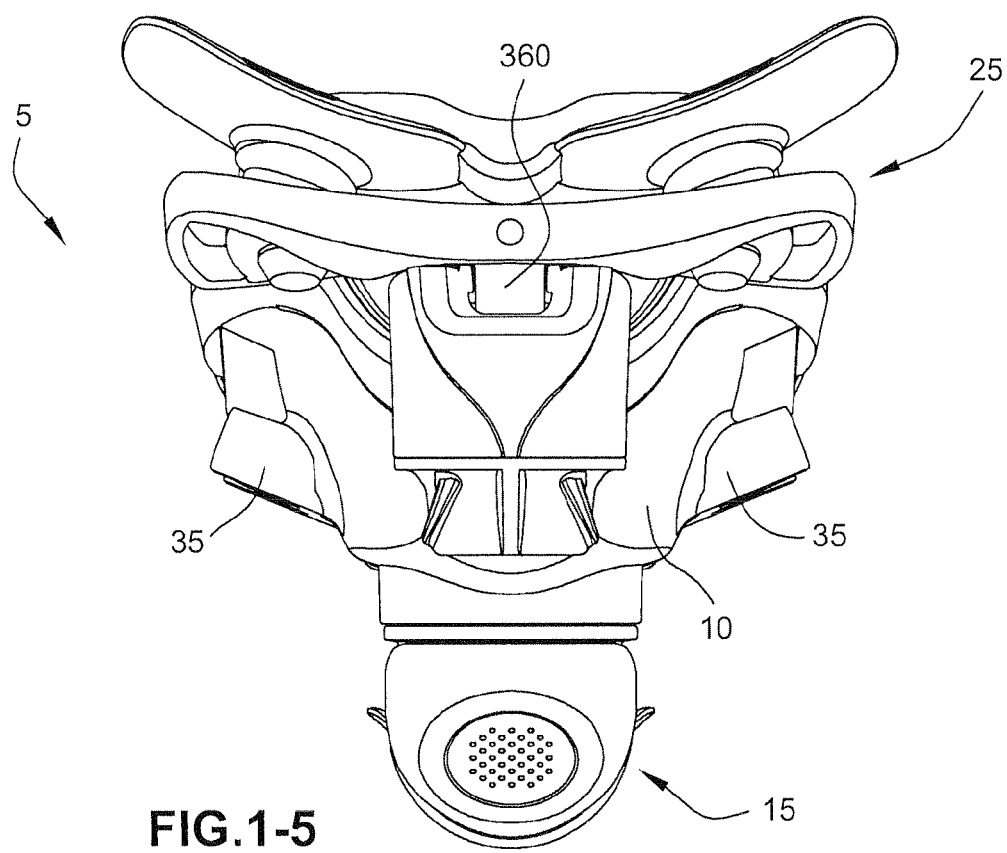

FIG. 5-1 shows elbow assembly 15 in a disconnected position relative to frame 10. Elbow assembly 15 includes an elbow 385 and a vented cover 390. A conventional swivel 395 may be attached to the elbow 385. FIG. 5-2 shows an exploded view of elbow 385, cover 390 and swivel 395.

4.1 Connection to Frame and Swivel

Elbow 385 includes a main body with a first end 400 for releasably engaging with an opening 11 in frame 10, and a second end 405 for releasably engaging with swivel 395. The first and second ends 400, 405 include a plurality of resilient, flexible arms 410 which are spaced apart from one another using slots. Upon insertion of the ends 400, 405 into either the swivel 395 or opening 11, arms 410 flex radially inwards until protrusions 415 at the end of each arm 410 overcome a feature (e.g., recess or end of wall) inside the aperture or swivel. In use, elbow 385 can rotate relative to both swivel 395 and frame 10. Elbow 385 can be detached from swivel 395 or frame 10 by squeezing one or more of the arms 410 so as to reduce the diameter to overcome the setting feature of the swivel 395 or frame 10, and then sliding the parts away from one another.

The first end 400 may thus be selectively engagable and disengagable with the frame 10 in a simple and convenient manner which does not require an additional attachment mechanism, such as a cerclip engaged around a groove at the first end 400 of the elbow 385, as in ResMed's Ultra Mirage II mask. However, a cerclip may be used as an additional or alternative securing device.

Referring to FIGS. 5-6 and 5-8, the protrusions 415 may have a leading angle 416 of from about 5°-60°, for example about 20°-35°. The angle 416 may be chosen so that the force required to assemble the elbow 385 to the frame 10 is reduced. For example, for older patients the angle 416 may be lower than the angle for younger patients. The angle 416 may also be chosen to provide adequate tactile feedback to the patient. A predetermined amount of initial, and continuing, resistance to insertion of the arms 410 of the elbow 385 into the frame 10 may be provided to enable to the patient to determine that the elbow 385 is configured for connection to the frame 10.

The protrusions 415 may also be configured to permit connection of the elbow 385 to only one frame type. For example, the protrusions 415 may have an "L" or "T" shape configuration to permit connection of the elbow 385 to the frame 10. The protrusions' shape would prevent the insertion of the elbow 385 into the frame of, for example, ResMed's Ultra Mirage II mask frame. The elbow 385 may thus be designed with, for example, a venting area that is specifically tuned for the mask frame 10, or for particular flow generator settings. Providing protrusions 415 that permit connection of the elbow 385 only to frames 10 configured for use with the venting area 420 of the cover 390 or for use only with flow generators tuned to the venting area assists in delivering the flow of pressurized breathable gas at the prescribed flow rate and/or pressure.

It should be appreciated that the protrusions configured to connect the elbow to the frame may have the same, or different, lead-in angle as the protrusions configured to connect the elbow to the swivel, or tube. It should also be appreciated that the protrusions configured to connect the elbow to the frame may have the same, or different, shape or configuration as the protrusions configured to connect the elbow to the swivel, or tube.

The elbow to frame connection can also be accomplished by other mechanisms, such as a ball and socket joint, a universal joint, a fixed non movable and or rotatable joint, etc.

4.2 Elbow and Cover Connection

Figures 1, 2, 3, 4, 5, 6:
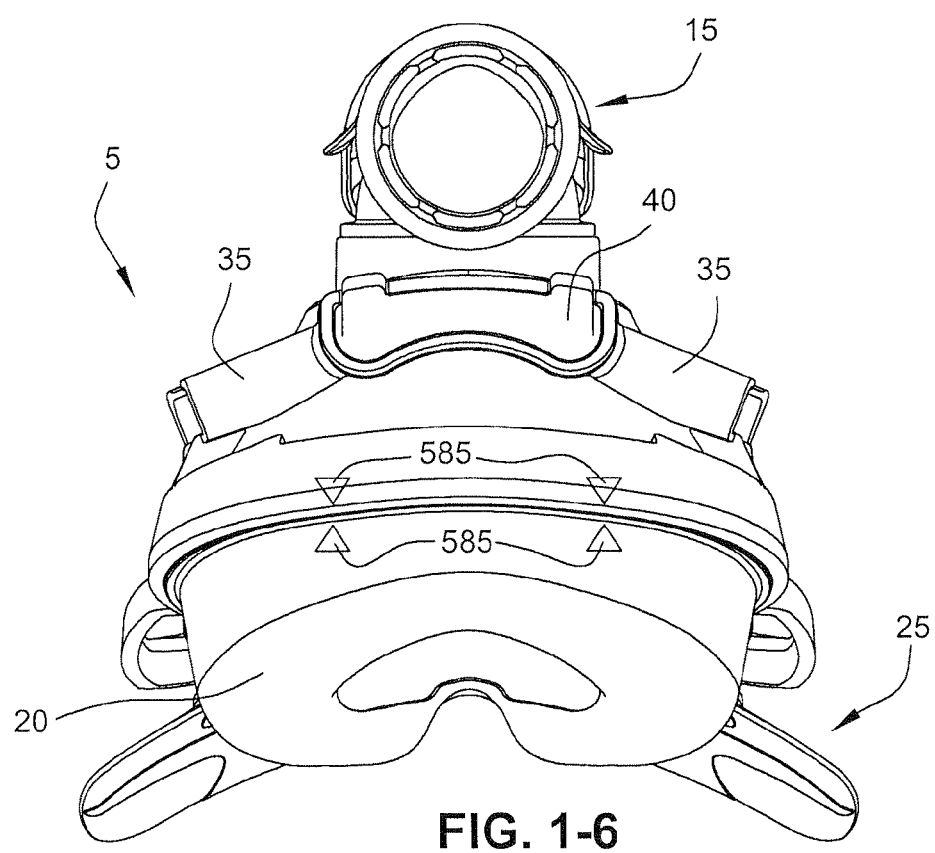

Elbow 385 is releasably attached to cover 390. Cover 390 includes venting area 420 which includes a plurality of vent holes 425 for washout of gases (carbon dioxide) exhaled from at least one of the patient's nasal passages. FIGS. 5-3 to 5-8 show the elbow 385 and cover 390 in an assembled position, FIGS. 6-1 to 6-6 show the elbow 385 in isolation, and FIGS. 7-1 to 7-9 show the cover 390 in isolation.

Elbow 385 has a main body 430 provided between ends 400, 405, as seen in FIGS. 5-2 and 6-1 to 6-6. Main body 430 includes a pair of lugs 435 on opposed sides of a vent opening 440 defined by a generally circular upstanding wall 445 terminating with a rim 450. Lugs 435 are adapted to engage with a pair of corresponding retaining members 455 provided on an inside surface of cover 390, as shown best in FIGS. 7-2 and 7-5.

Each retaining member 455 includes a ramped front surface 460 provided towards the front open end of cover 390 and a rear surface 465 that engages a rear surface of the lug 435 in the connected position. The lateral sides of the cover 390 flex outwardly upon engagement between the front surface 460 of the retaining members 455 and the front surface 462 of the lugs 435 and then the sides flex inwards when the retaining members 455 overcome the lugs 435 where the rear surface 465 of the retaining member 455 engages the rear surface 466 of the lug 435 in the engaged position.

Figures 1, 2, 3, 4, 5, 6, 7:
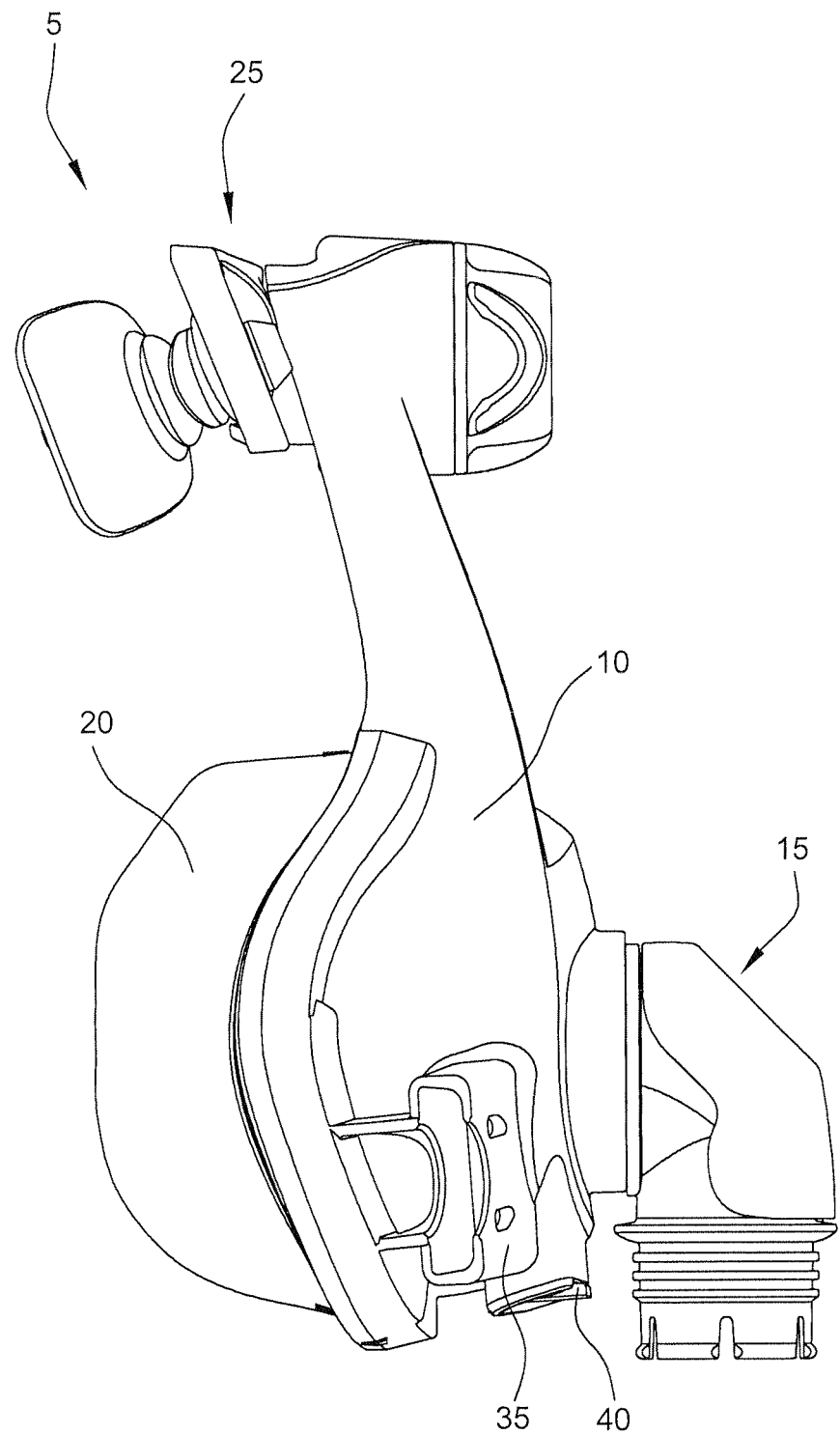
Figures 1, 2:
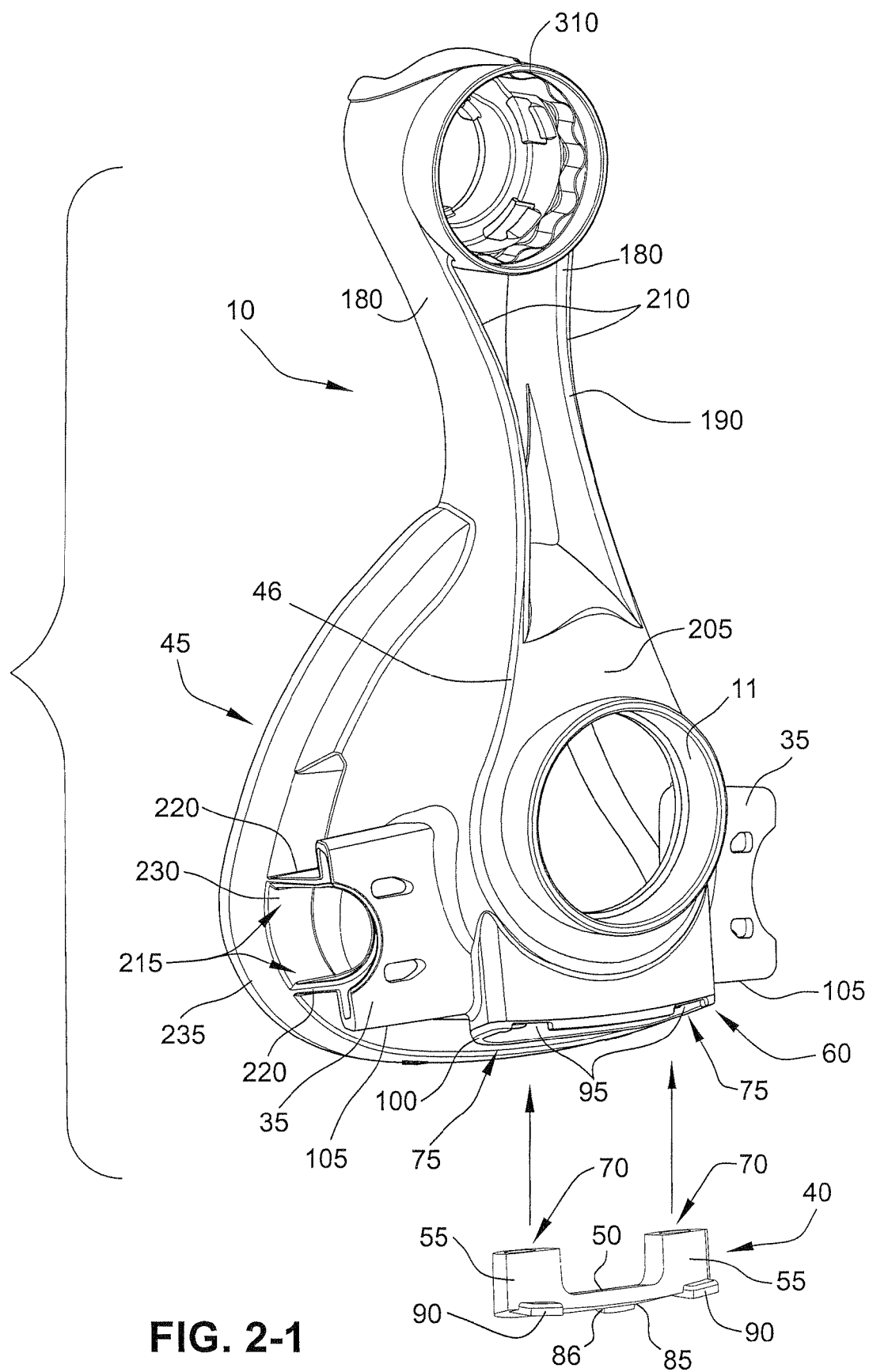
Figure 2:
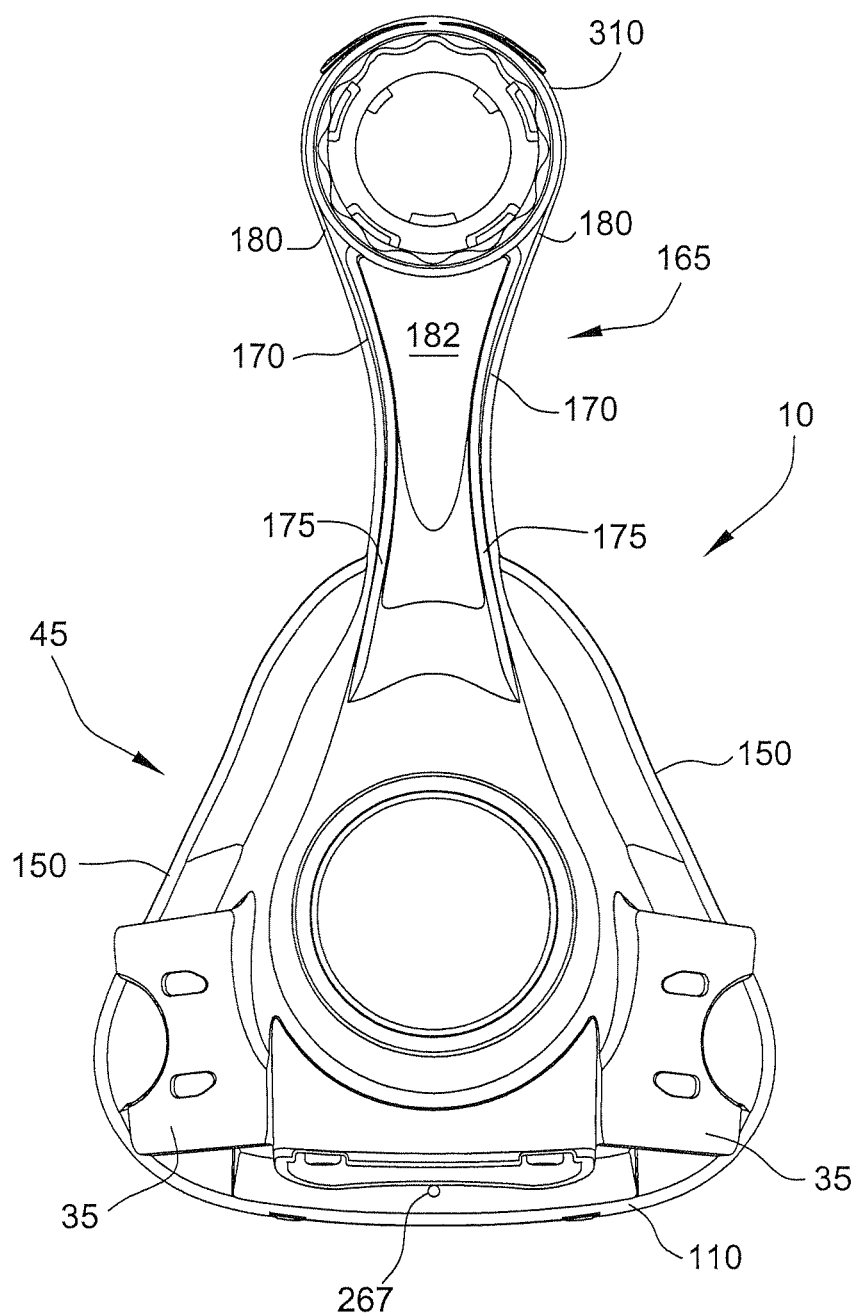
Figures 2, 3:
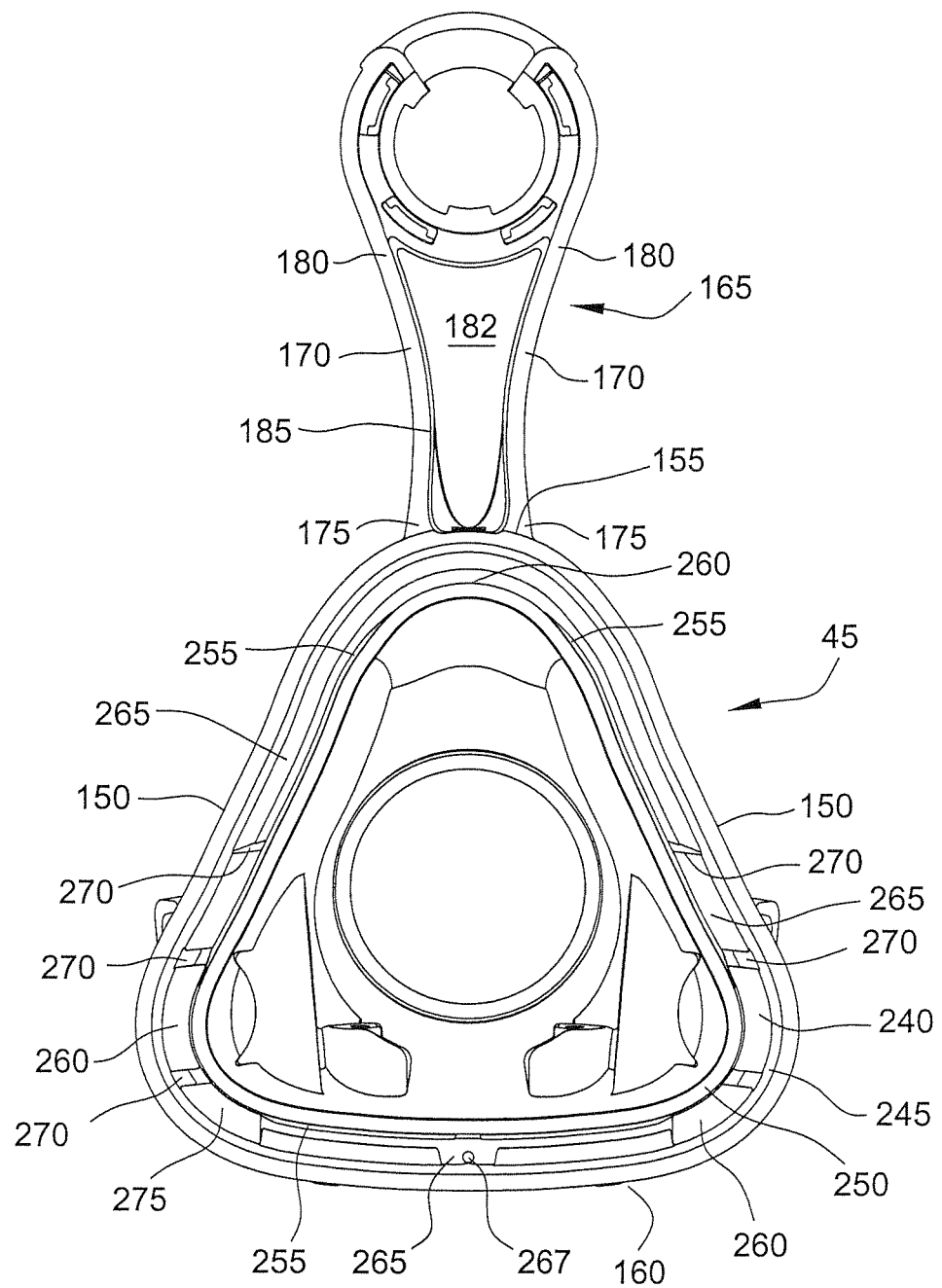
Figures 2, 3, 4:
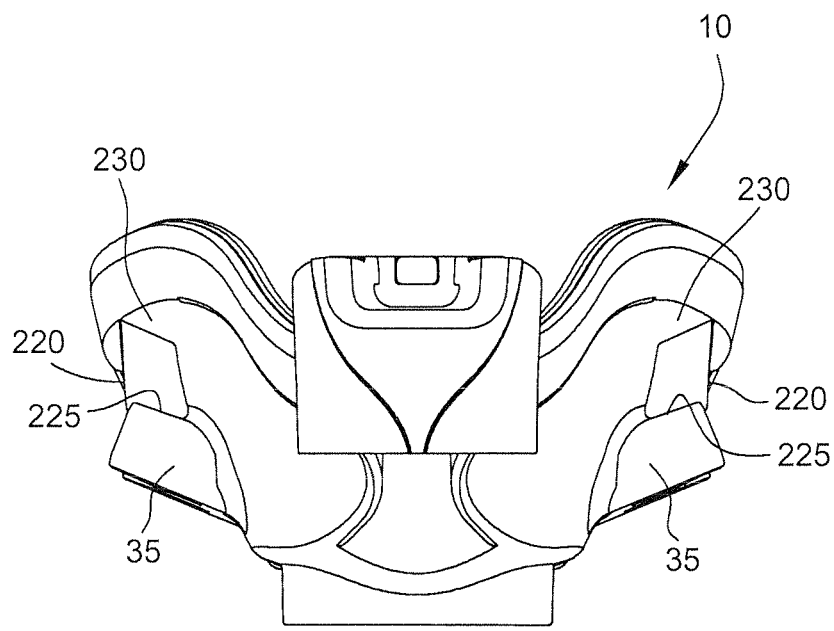
Figures 2, 3, 4, 5:
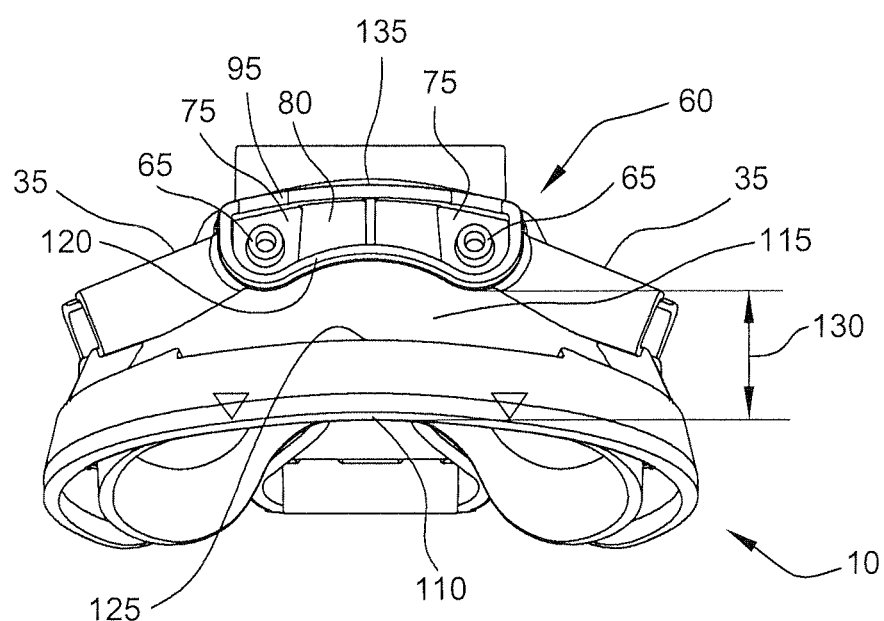
Figures 2, 3, 4, 5, 6:
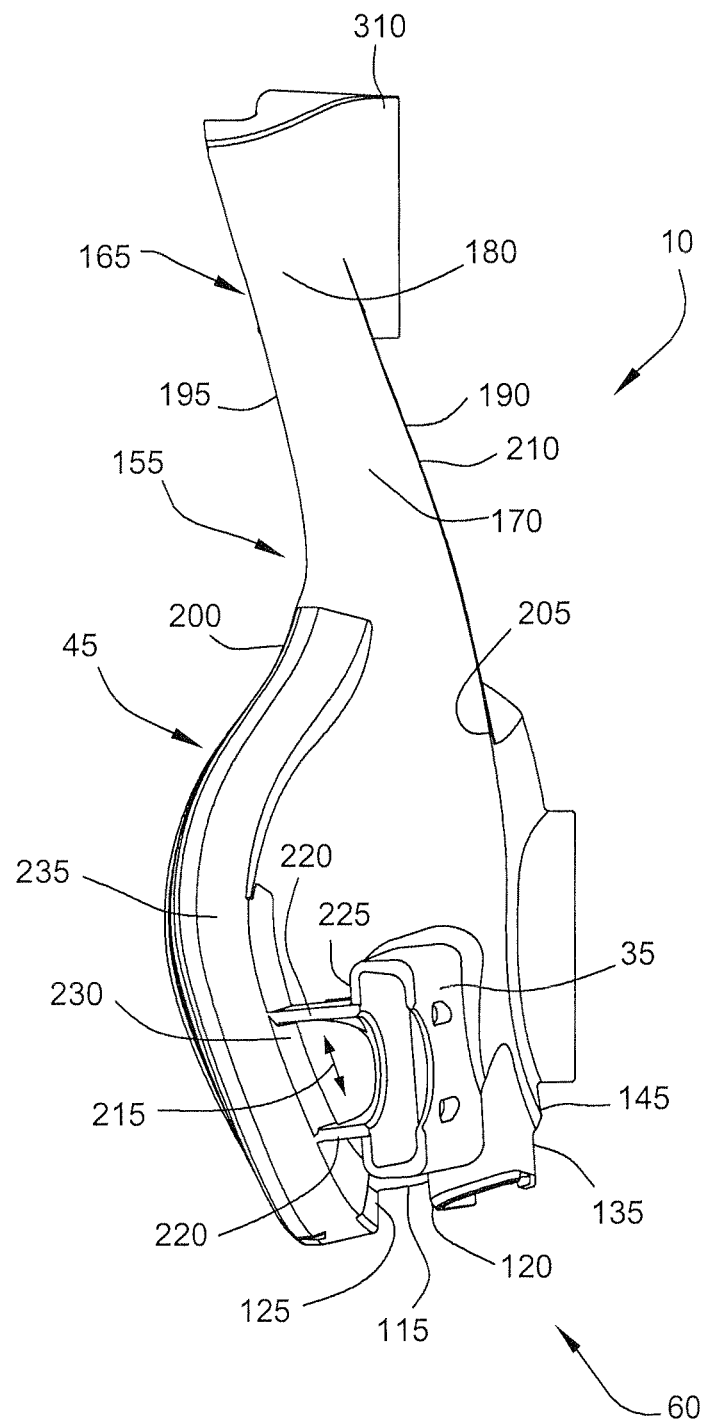

In an alternative embodiment shown in FIG. 6-7, the elbow 385 includes lugs 435 (only one shown), each lug 435 having a front surface 462 and a rear surface 466. The lug 435 includes lug extensions 463 on opposite sides of the lug 435.

The elbow shown in FIG. 6-7 is configured for use with a cover described in more detail below with respect to FIGS. 7-10 to 7-12 and FIG. 9-14.

In the connected position, venting area 420 of cover 390 is aligned with an in communication with vent opening 440 of elbow 385. In addition, cover 390 may include a bottom edge 470 that rests on or is oriented adjacent a flange 475 arranged towards second end of elbow 385, as seen in FIGS. 5-4 to 5-8.

Main body 430 may include one or more tabs 480 which serve to space the cover 390 away from the outer surface of the main body 430, as shown in FIGS. 6-1 and 6-3. The spacing tabs 480 could also be provided on the inside surface of cover 390.

FIGS. 5-10 and 5-11 are cross sections of the cover 390 and elbow 385 in the connected position. In FIG. 5-10, the circular upstanding wall 445 of the elbow 385 abuts an inner surface 485 of the cover 390 defining a perimeter of the venting area 420. Upstanding wall 445 is cut an angle such that the outer radius is higher than the inner radius (approximating a cone shape) so as to define an abutment surface 490 which is angled relative to horizontal in the range of about 10-25 degrees, but it could also be between 10-50 degrees or more, or even less than 10 degrees. The inner surface 485 of the venting area 420 of the cover 390 is angled in a complementary fashion.

By abutting the cover 390 and elbow 385 along angled surfaces, the target contact area is effectively increased which helps lower manufacturing tolerances by allowing variation in molding. The angled contact also helps to self locate and position the cover 390 relative to the elbow 385, which in turn helps to properly locate the lugs 435 of the elbow 385 relative to the retaining members 455 of the cover 390. This makes the assembly process easier and more intuitive.

In the engaged position, the rim 450 of the elbow 385 and the inner surface 485 of the cover 390 contact one another and effectively form a seal therebetween such that washout gas must escape through the venting area 420 rather than elsewhere. To enhance the seal, the contact surfaces of the cover 390 and rim 450 are made of a relatively rigid material, such as polycarbonate. In addition, the engagement between the lug 435 and retaining member 455 is such that the connection creates pretension to help maintain the seal between the rim 450 and inner surface 485 of the cover 390. FIG. 5-10 shows a slight gap G1 between the retaining member 455 and the main body 430 of the elbow 385, and a slight gap G2 between the lug 435 and the inside top/side surface of the cover 390, which helps prevent bottoming out with the result being to maintain pretension. Note also that the rim 450 is preferably spaced a small distance G3 from the top wall of the cover 390 again to prevent bottoming out and thereby ensuring a pretensioned connection.

In FIG. 5-11, the inner surface of the cover 390 is shown to similarly abut the rim 450 of the elbow 385 along an angle. Further, the upper edge 495 of the cover 390 abuts or is adjacent to an upper flange 500 adjacent the first end of elbow 385, much like the lower edge 470 of cover 390 abuts or is adjacent to lower flange 475.

FIG. 5-12 is an alternative embodiment which shows a cross section in which the cover 390 and elbow 385 are in a connected position. This variant is similar to that shown in FIGS. 5-10, but the engagement between the rim 450 of the elbow and the inner surface 485 of the cover is slightly modified. Specifically, the upstanding wall 445 of the elbow 385 is formed such that its height at the inner diameter is greater than the height of the wall at the outer diameter, i.e., the reverse cone shape compared to FIG. 5-10. The angle in FIG. 5-12 is between about 5-25 degrees.

4.3 Cover

The venting area 420 of cover 390 includes a plurality of holes 425, e.g., about 20 to 60 holes or more, depending on hole size. In the example shown, venting area 420 includes about 35 to 45 holes 425, or in one specific example, 37 holes.

Venting area 420 is positioned on the elbow 385 so as to exhaust gas away from the patient in a quiet manner. As shown in FIG. 5-9, venting area 420 may be slightly recessed (e.g., about 0.1 to 1 mm, or about 0.5 mm) compared to the surrounding area of the cover 390 to prevent damage to the vent holes 425 and/or to provide a tactile clue as to where to apply force when assembling the cover 390 to elbow 385. Alternatively, one or more protrusions or dots 391 can be provided to the surrounding area to encourage the patient to apply assembly force in that location rather than contact the holes 425 and risk fouling of the holes 425. Generally, the cover 390 may be frosted or textured which may help gripability for assembly purposes. A protective layer, or rib(s), 392 can be added to the outside of the cover 390 to protect the holes 425, and such layer can be flush with the surrounding portions of the cover 390, or it may even protrude slightly.

4.3.1 Hole Dimensions

Figures 1, 3:
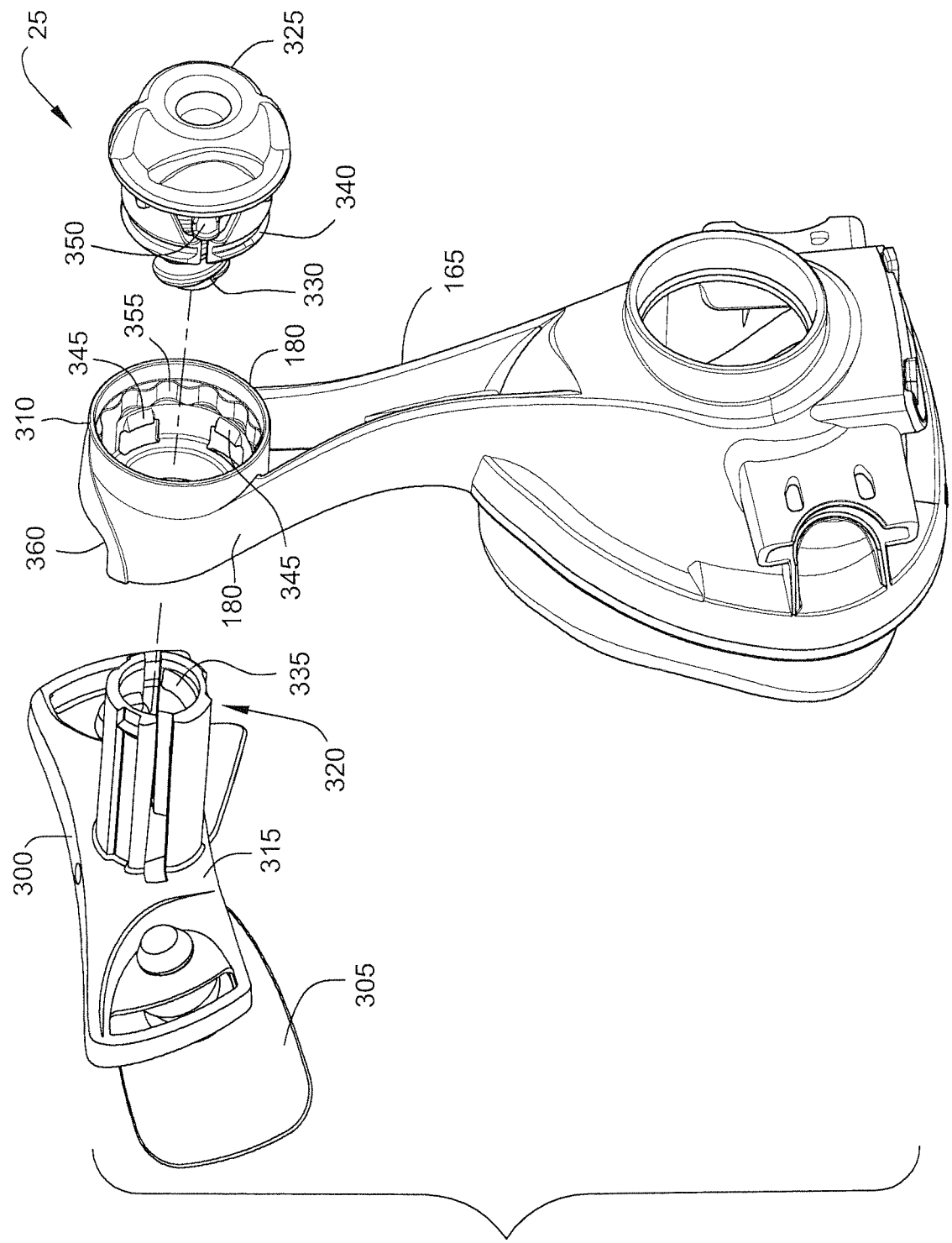
Figures 2, 3:
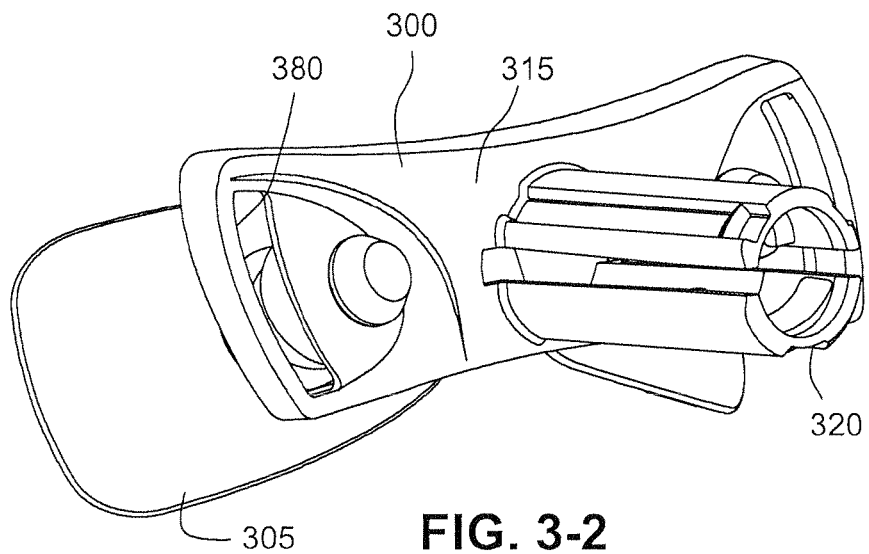
Figure 3:
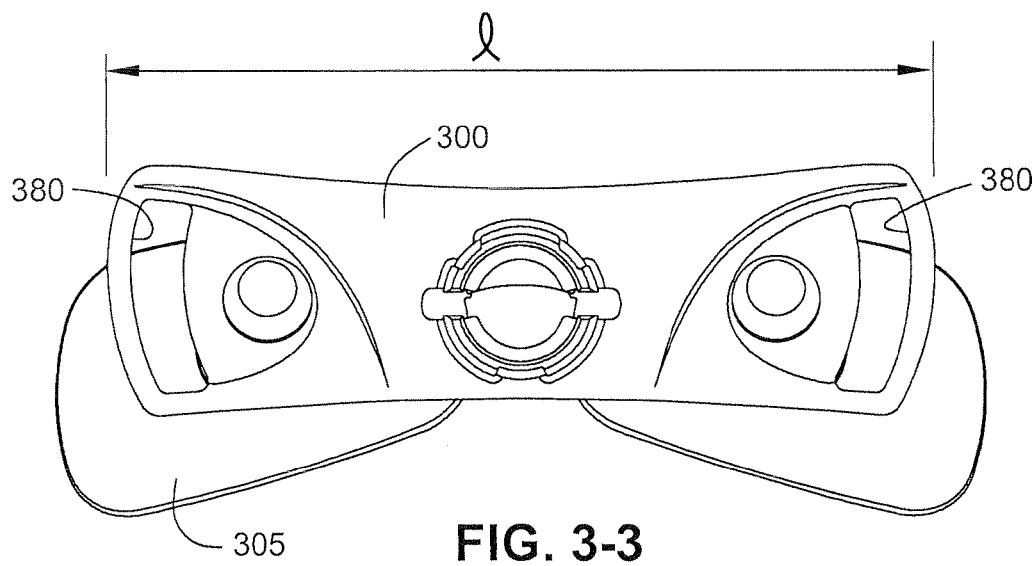
Figures 3, 4:
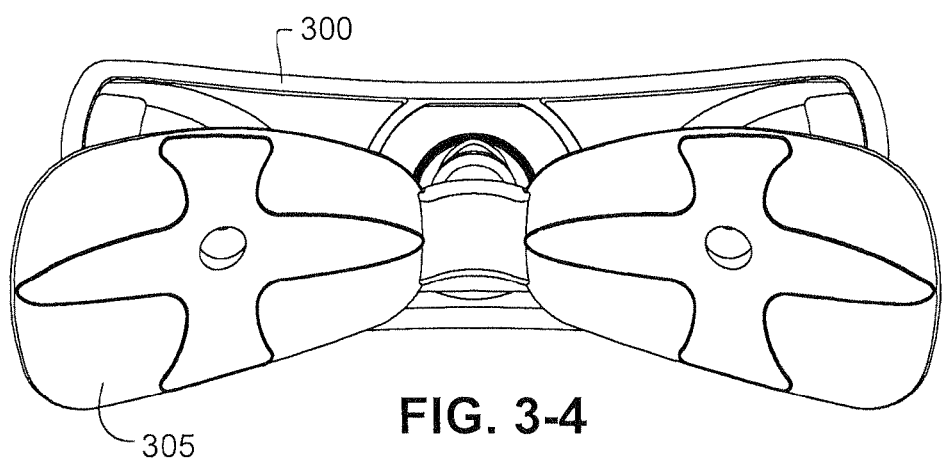
Figures 3, 4, 5:
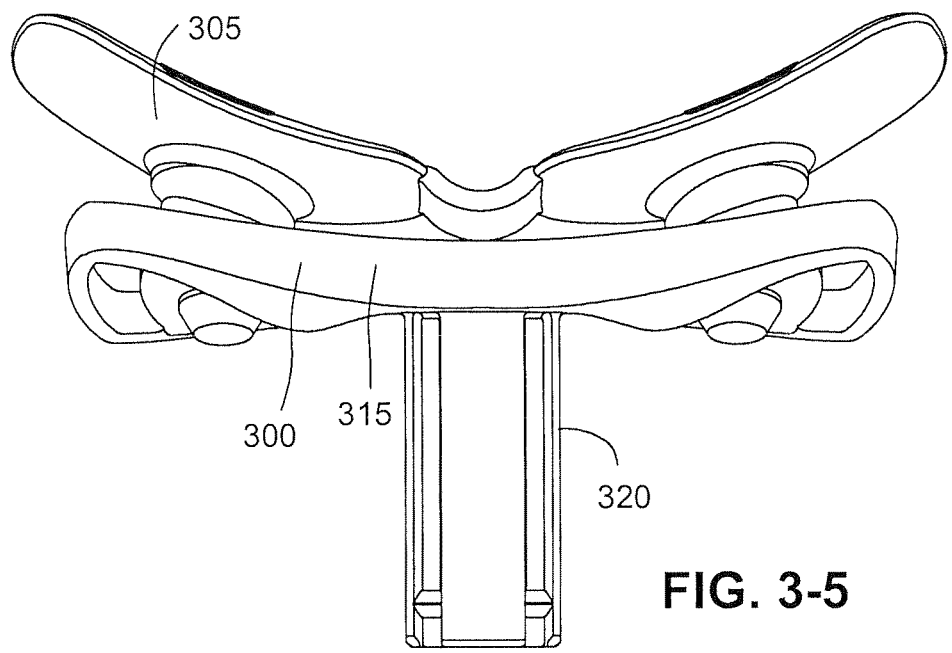
Figures 3, 4, 5, 6:
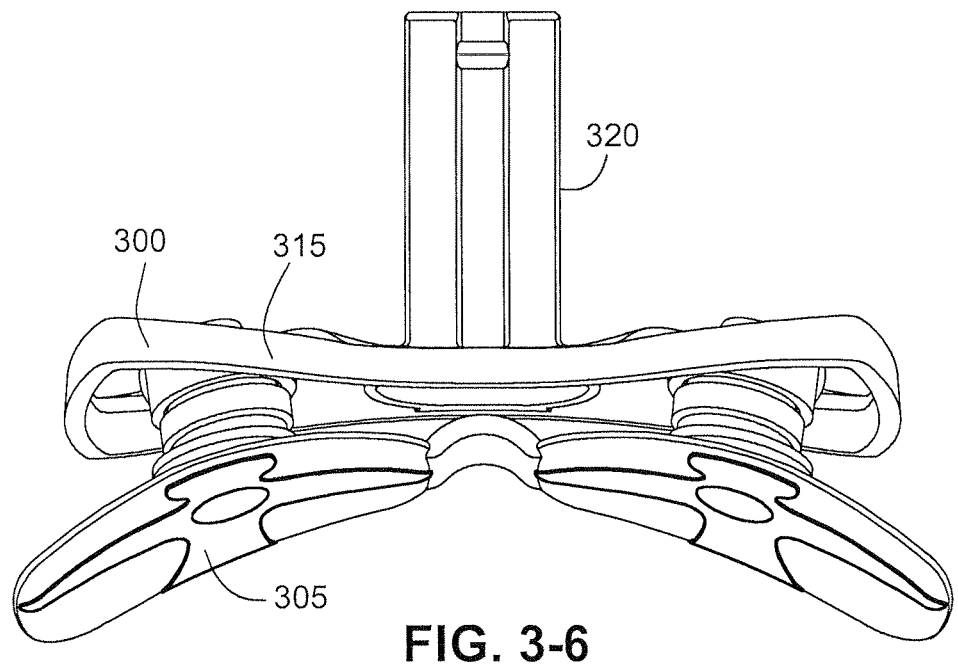
Figures 3, 4, 5, 6, 7:
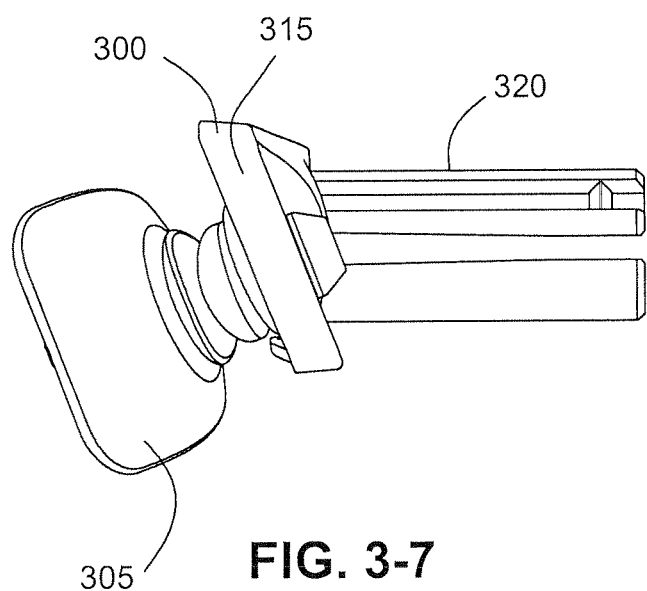
Figures 3, 4, 5, 6, 7, 8:
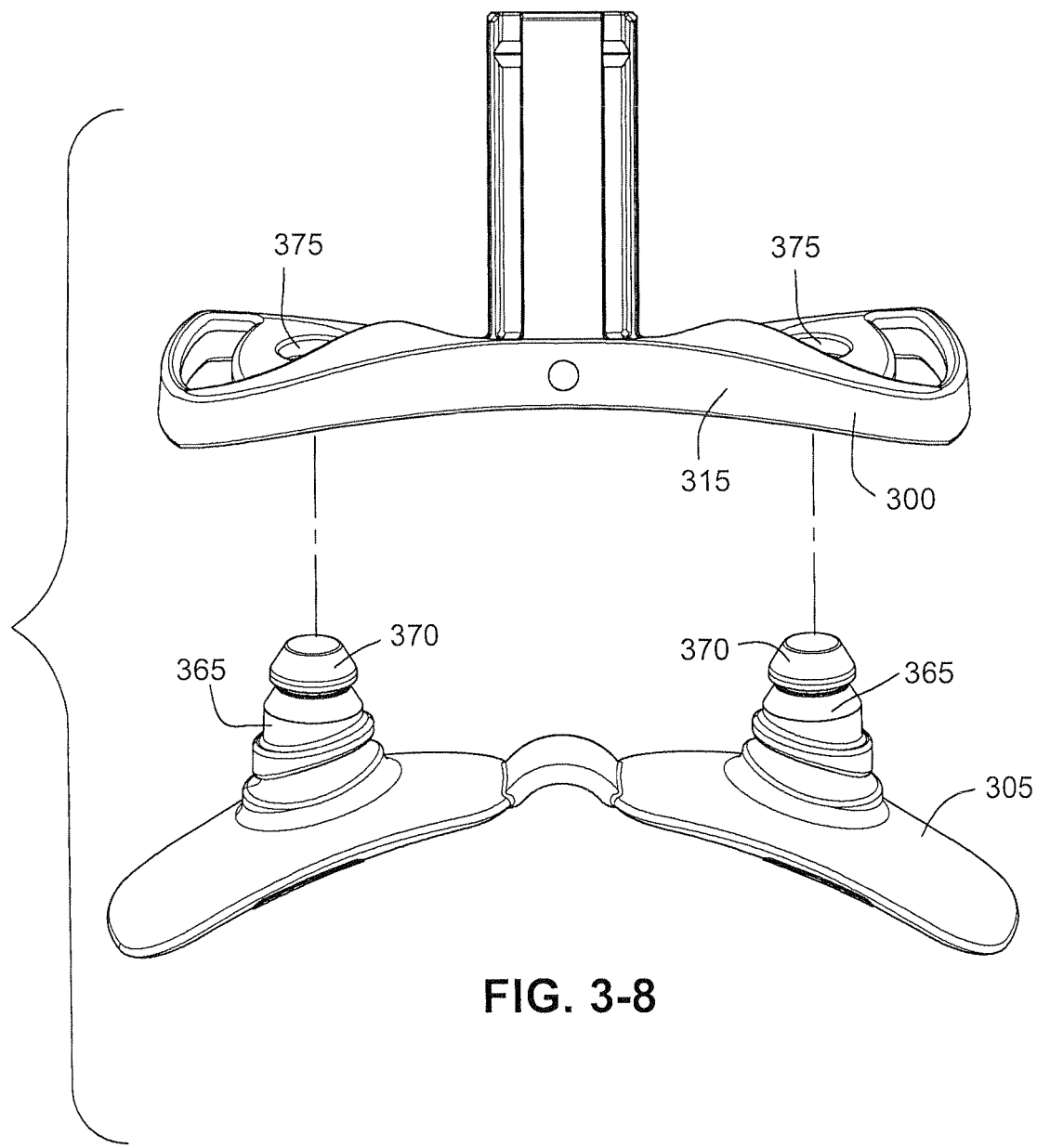
Figures 1, 4:
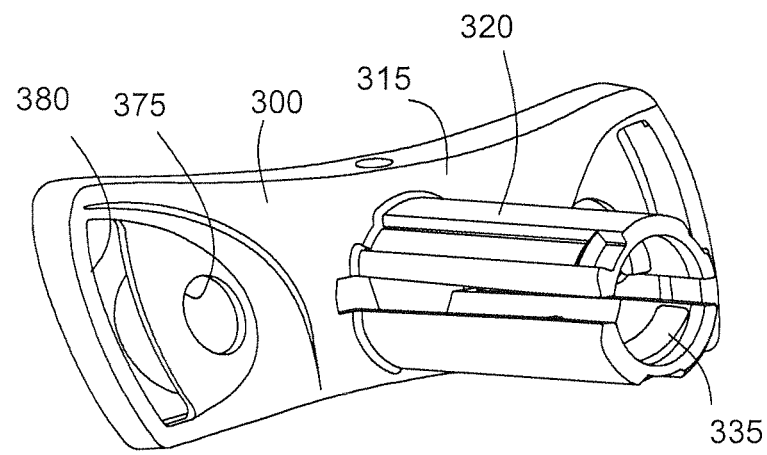
Figures 2, 4:
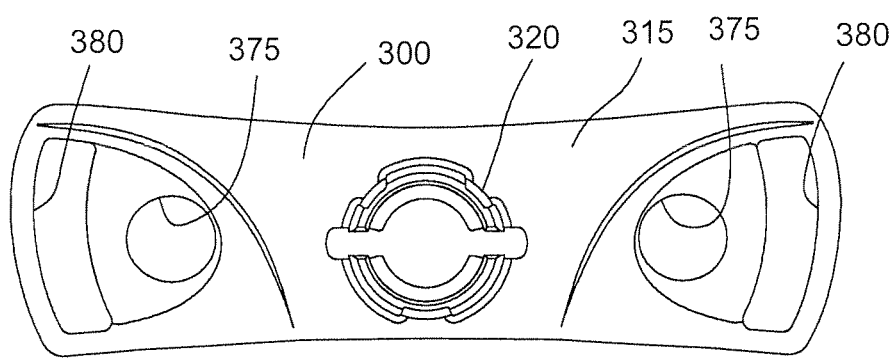
Figures 3, 4:
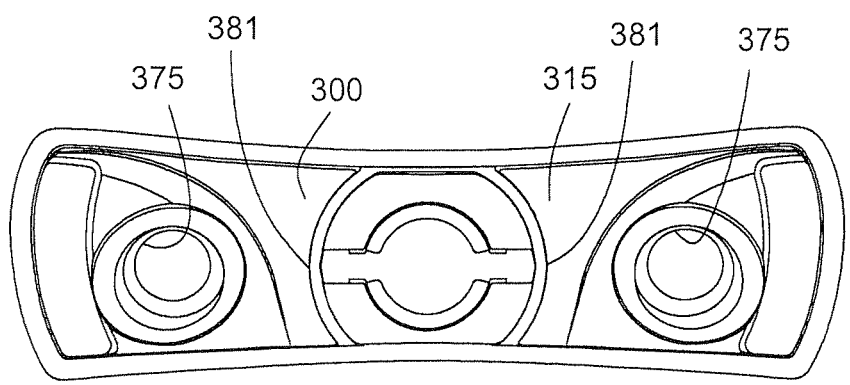
Figure 4:
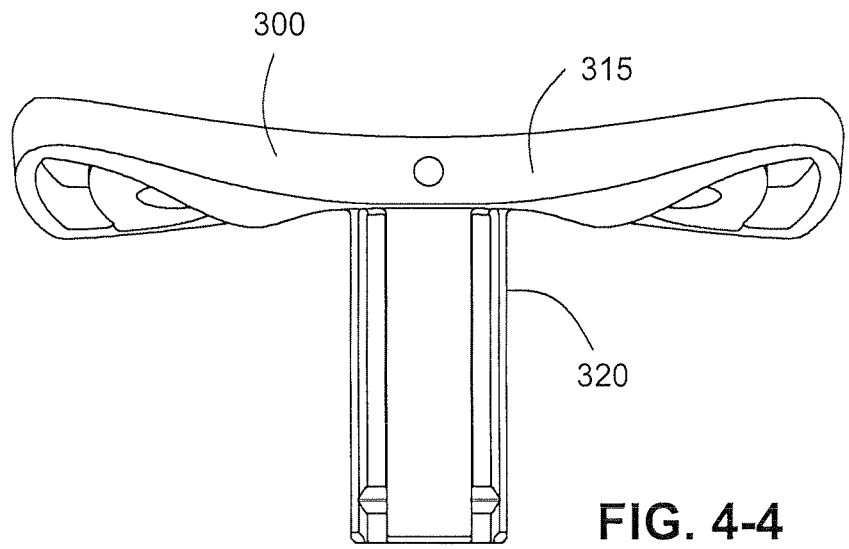
Figures 4, 5:
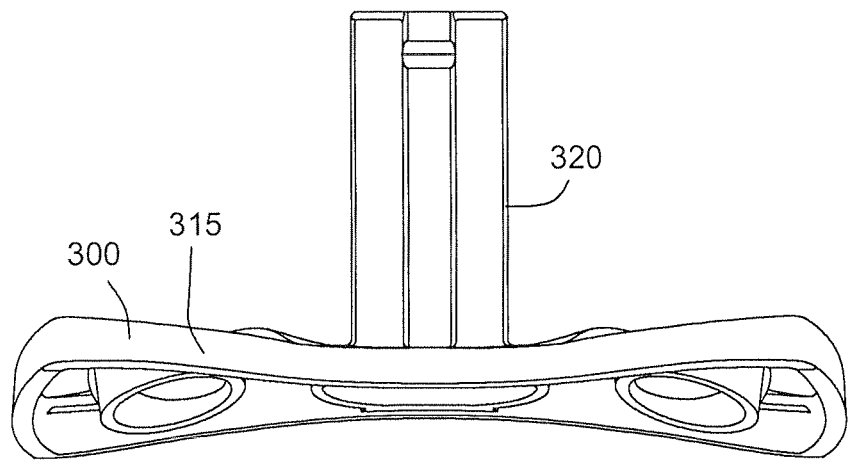
Figures 4, 5, 6:
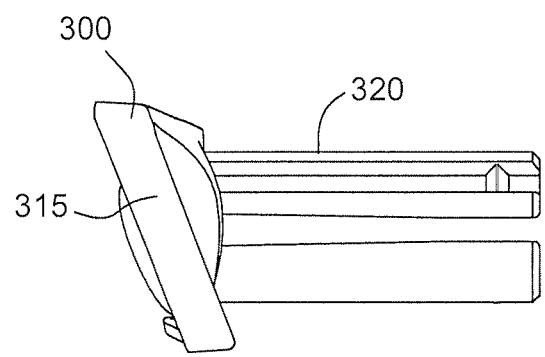
Figures 1, 5:
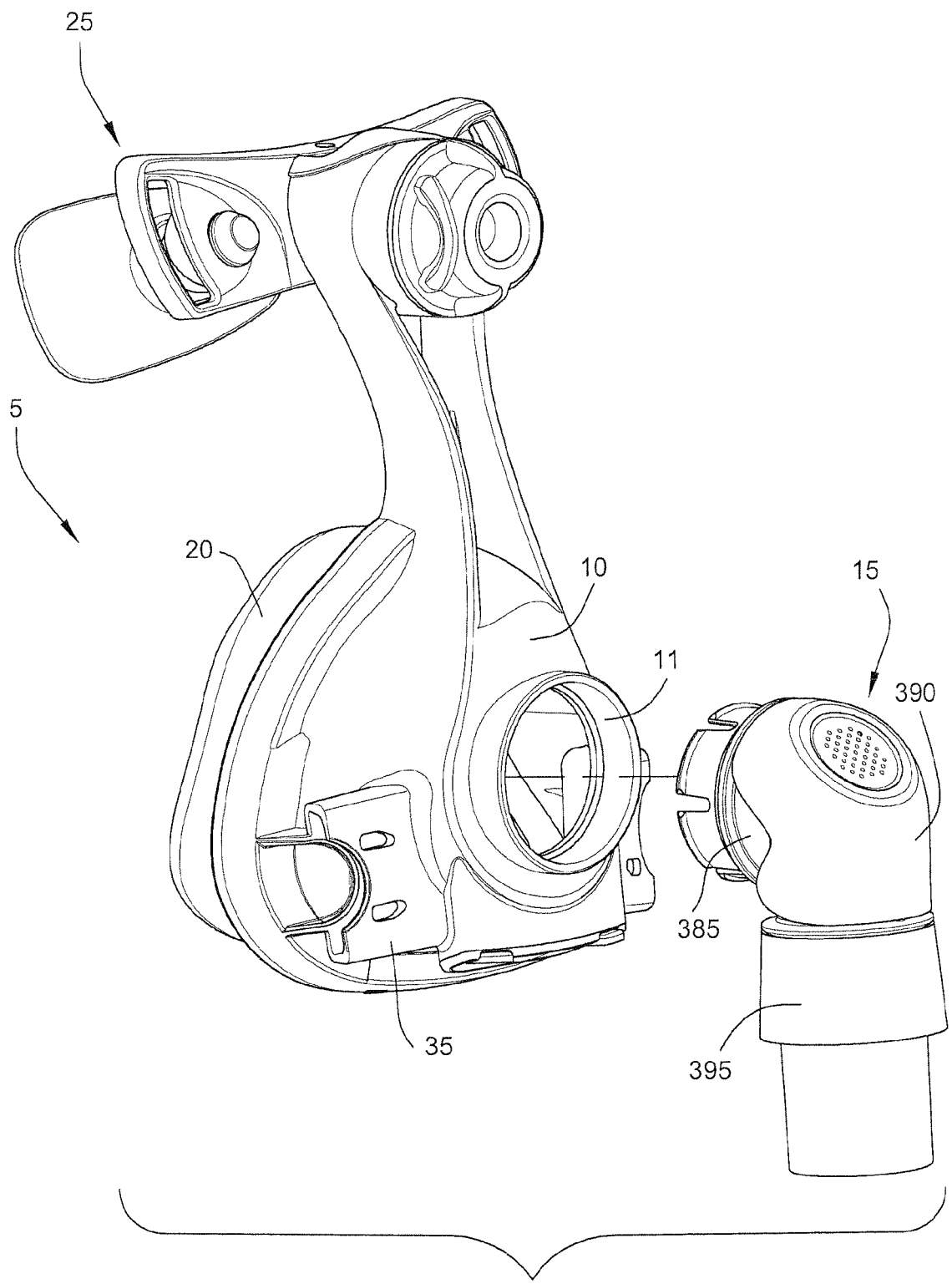
Figures 2, 5:
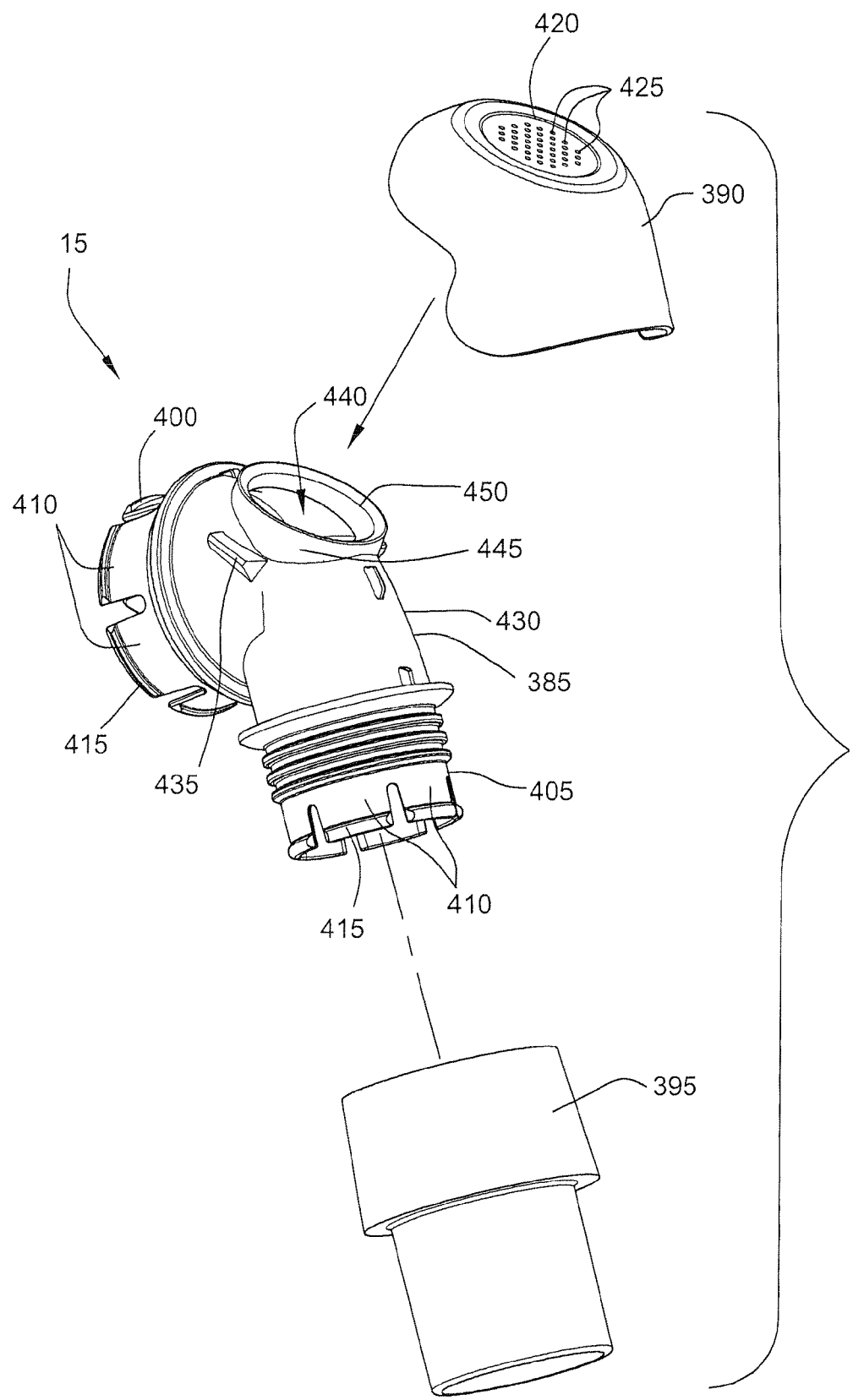
Figures 3, 5:
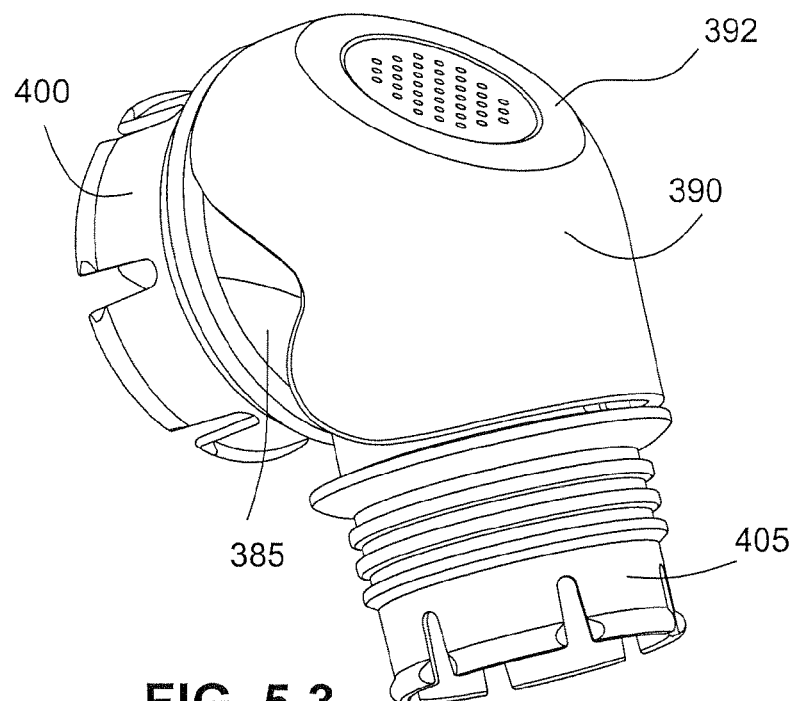
Figures 4, 5:
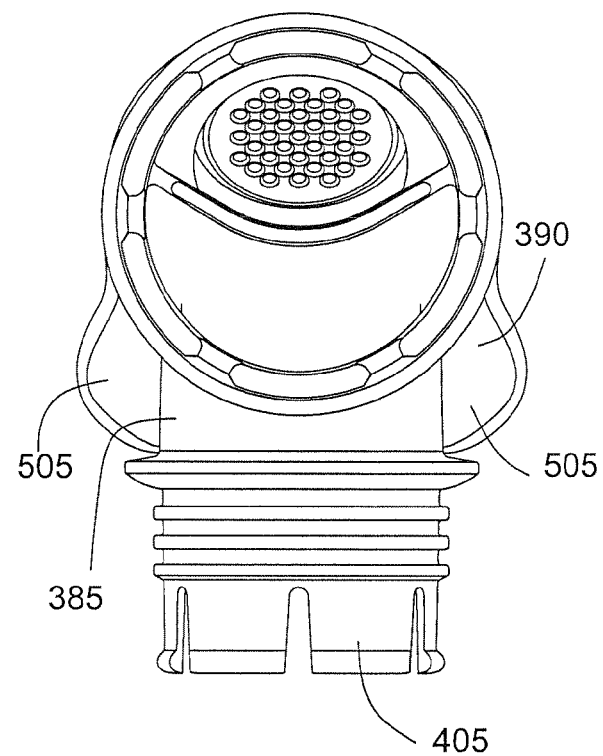
Figure 5:
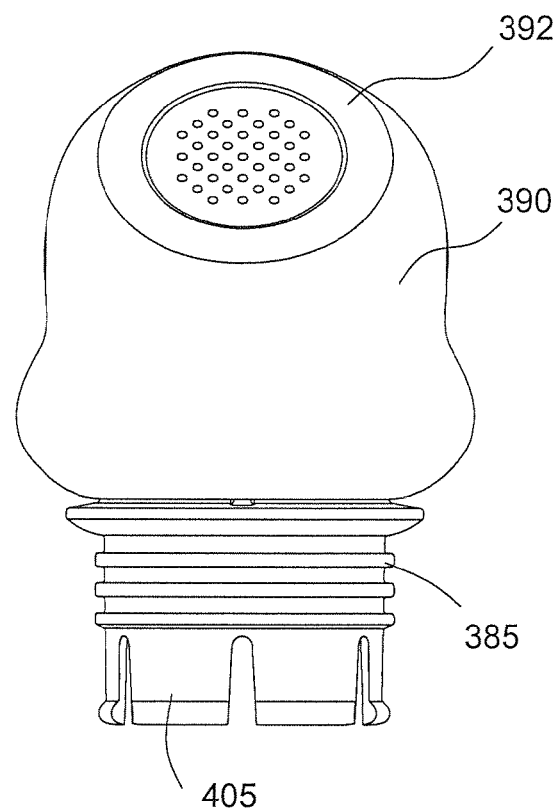
Figures 5, 6:
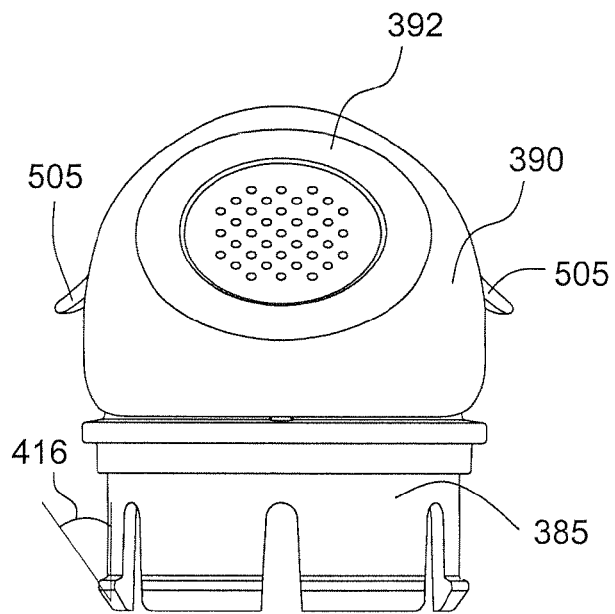
Figures 5, 6, 7:
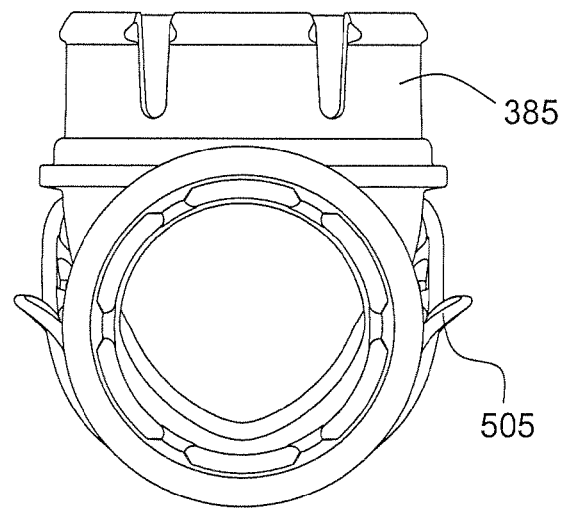
Figures 5, 6, 7, 8:
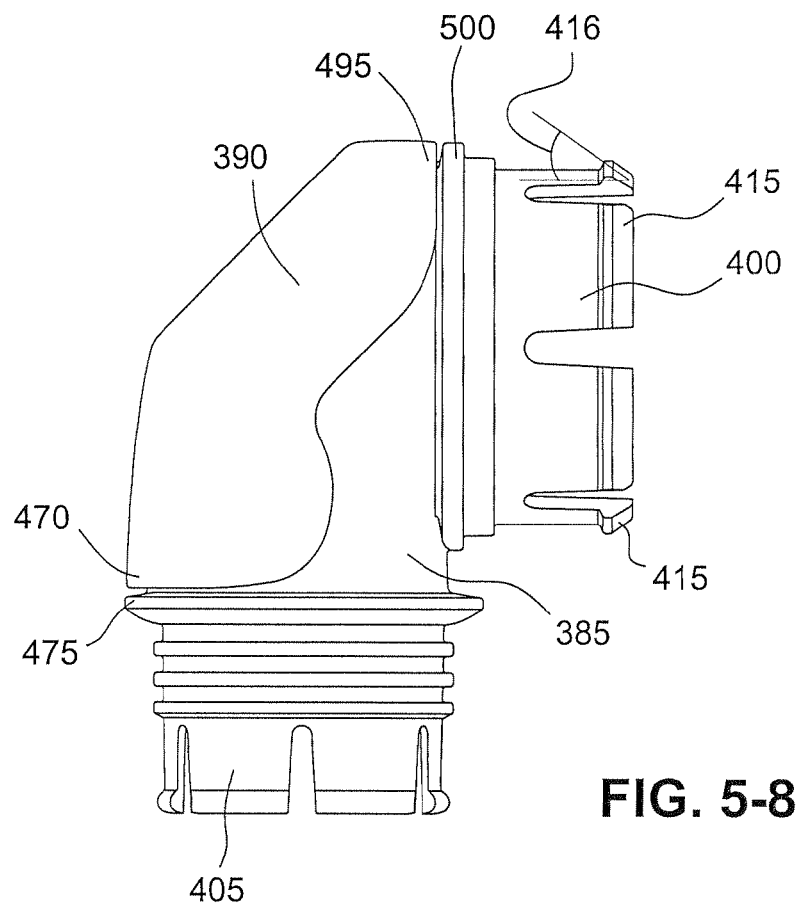
Figures 5, 6, 7, 8, 9:
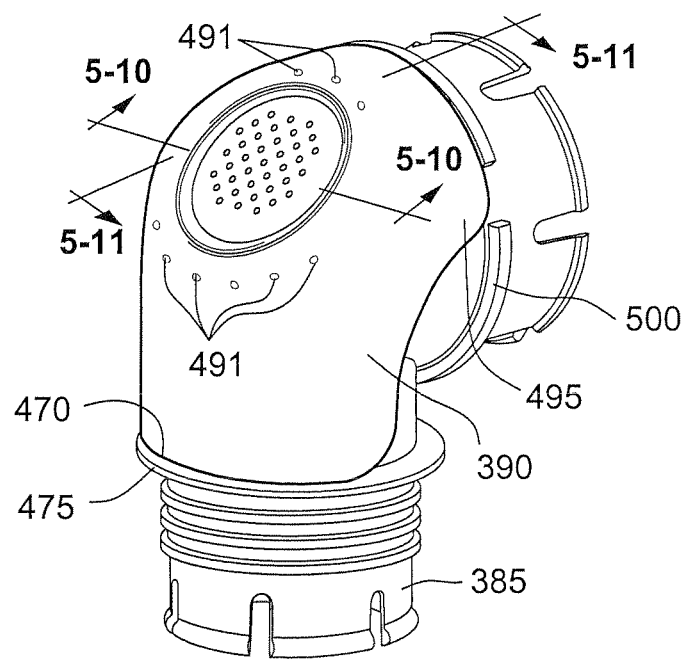
Figures 5, 6, 7, 8, 9, 10:
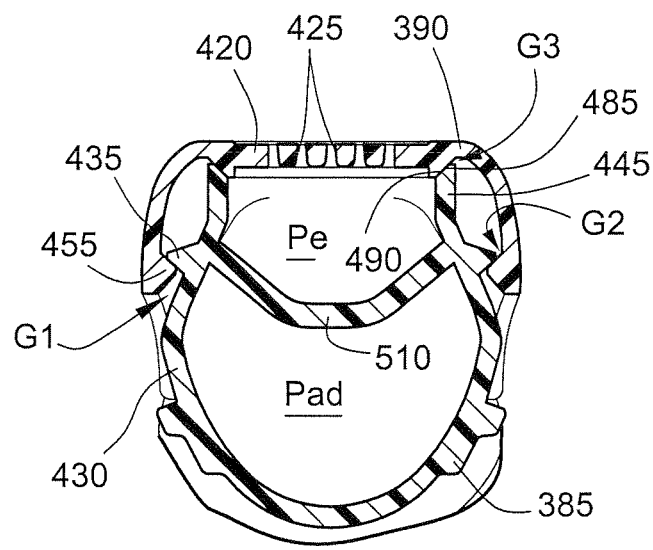

As shown in FIG. 7-9, each hole has converges from inside to outside such that the exit diameter $d_e$ is smaller than the inlet diameter $d_i$. The included angle between opposed surfaces of each hole is about 10 degrees; the draft angle of each side wall is about 5 degrees. The thickness of the venting portion, or in other words the length of each hole 425, is about 2.1 mm. Outer diameter $d_e$ is about 0.7 mm and the ratio of the length to outer diameter $d_e$ is preferably about 3. The inner diameter $d_i$ is radiused to promote quiet flow. It should be appreciated that these dimensions may vary up to 10-20%.

In an alternative, the holes 425 could be provided directly to the elbow 385 without the need for a cover. In another alternative, the cover 390 could be made of an elastic material which is fitted to the elbow 385.

4.3.2 Hole Pattern

Holes 425 are arranged in a pattern or array that promotes quiet flow and allows the most number of holes in the smallest available space without creating interfering jets that might cause undue or unnecessary noise. As shown in FIG. 7-7, hole pattern has a diamond like shape, or square. However, the pattern could also be a simple grid, a true diamond, triangle (FIG. 8-1), round/concentric ring (FIG. 8-2), etc. The venting area could also include elongated slots, or slots with holes.

4.3.3 Wings

Cover 390 includes a wing 505 along each side of the lower portion thereof, as shown in FIGS. 7-1 to 7-6. A wing or tab may also be provided to the top of the cover. Wings 505 facilitate attachment and detachment between the cover 390 and the elbow 385. They also provide a visual clue as to how to correctly attach the cover to elbow. As shown in FIGS. 5-4, 5-6 and 7-4, wings 505 have end portions that extend away from the main body 430 of elbow 385 so that the patient can easily lift the cover 390 away from the elbow 385.

4.3.4 Compound Shape

Cover 390 has a compound shape including compound curves for structural shape. For example, FIGS. 7-1 to 7-3 and 7-6 show various compound curves to allow the strength for the cover 390 to be repeatedly attached to and removed from the elbow 385. As shown in FIG. 7-8, the cover 390 has a thickness t in the areas surrounding the venting area 420 of between about 1.0 mm - 1.2 mm, for example about 1.1 mm. As also shown in FIG. 7-12, the cover 390 has radii 458, 459 next to the sealing surfaces of the inner surface 485 of the cover and the rim 450 of the elbow 385. The radii 458 may be between about 0.25 mm - 0.75 mm, for example about 0.5 mm.

4.3.5 Alternative Cover Embodiment

Referring to FIGS. 7-10 to 7-12, a cover 390 according to an alternative embodiment includes a retaining member 455 having a ramped front surface 460 and a ramped rear surface 465. The cover 390 further includes a wall 457 on each side that extends below each retaining member 455 to each wing 505. Thickened portions 456 are provided on opposite sides of the retaining member 455. The thickened portions 456 may have a thickness of between about 1 mm-2 mm.

The thickness t of the cover 390 in the areas surrounding the venting area 420 may be between about 0.9 mm-1.1 mm, for example about 1.0 mm. The radii 458, 459 next to the sealing surfaces of the inner surface 485 of the cover and the rim 450 of the elbow 385 may be between about 1.0 mm-2.0 mm, for example between about 1.25 mm-1.75 mm, for example about 1.5 mm.

The cover 390 of FIGS. 7-10 to 7-12 may be used with the elbow of FIG. 6-7. The lug extensions 463 of the lug 435 of the elbow 38 engage the thickened portions 456 provided on the opposite sides of the retaining member 455 during connection of the cover 390 to the elbow 385 to assist in deflection of the cover 390. The engagement of the lug 435 of the cover 390 of FIGS. 7-10 to 7-12 with the retaining member 455 creates a pretension to help maintain the seal between the rim of the elbow and the inner surface of the cover.

The provision of the wall 457, the increased radii 458, 459, the thickened portions 456, and/or the reduced thickness of the cover in the area surrounding the venting area reduce the maximum tensile stress the cover 390 is subjected to during connection to the elbow, and reduce the tensile stress on the cover 390 near the edges of the cover 390. The maximum tensile stress experienced by the cover shown in FIGS. 7-10 to 7-12 may be about 15%-25%, for example about 20%, lower than the maximum tensile stress experienced by the cover shown in FIGS. 7-1 to 7-9. The tensile stress near the edges of the cover of FIGS. 7-10 to 7-12 may be about 35%-50%, for example about 43%, less than the tensile stress near the edges of the cover of FIGS. 7-1 to 7-9.

4.4 Baffle

Elbow 385 includes a baffle 510 that is positioned in the elbow 385 and adjacent where the elbow 385 connects to frame 10. Gas is delivered to the second end of the elbow 385 via an air delivery hose and travels along the elbow 385 and into the breathing chamber of the mask via the opening 11 of the frame 10.

FIGS. 5-10 and 5-11 show that the baffle 510 divides the upper arm of the elbow 385 into two portions, an air delivery passage Pad and an exhaust passage Pe. Baffle 510 is placed so as to divide the elbow 385 to allow the minimum area to satisfy impedance requirements plus a safety factor of 10 percent.

As shown in FIGS. 5-10, 5-11 and 6-2, baffle 510 has a gradual U-shaped profile with the ends turned up towards the top of the elbow, e.g., like a "smiley" face, to improve the efficiency of $CO_2$ washout, which allows the flow rate to be reduced (up to 10-20%) and still maintain adequate washout, while also reducing noise due to the lower flow rate. Stated differently, the PAP device can follow a different flow curve. FIG. 5-10 shows a baffle made up of three linear sections (two sides and a bottom) joined by short curved walls, wherein FIG. 5-22 has a more gradual U-shape profile. U.S. Pat. Nos. 6,907,882 and 7,011,090 disclose elbows with various baffles that can be arranged according to the current teachings, each incorporated herein by reference in its entirety.

As shown in FIG. 5-11, the baffle 510 forms a sharp turn 426 with respect to the lower leg of the elbow, which may increase impedance. The baffle 510 also forms a sharp edge 427 where the lower part of the elbow joins the upper part. However, these sharp edges can be smoothed out in an alternative embodiment.

As seen in FIG. 6-2, the baffle 510 is cantilevered towards the first end of the elbow 385, meaning that the sides 515 of the baffle 510 are not supported by the interior side walls of the elbow 385 at least along a portion of the length of the baffle 510. This allows the arms 410 to more readily flex upon assembling and disassembling the elbow 385 to the frame 10. The baffle 510 extends to the end of flex arms 410 (e.g., see4 FIG. 5-11), which means that about half of the length of the baffle 510 is unsupported. However, baffle 510 may extend beyond the length of the arms 410, or the baffle 510 may be recessed into the elbow 385, i.e., shorter than or short of the arms.

5.0 Alternative Elbows

FIGS. 9-1 to 9-23 show alternative elbows according to embodiments of the present invention.

FIGS. 9-1 to 9-8 illustrate elbow assemblies in which the retaining member of the cover 390 takes the form of an opening or slot 520 through which the lug 435 of the elbow 385 may extend. The lugs 435 abut against a side wall of the slot 520 to maintain engagement between the cover 390 and elbow 385. The appearance of the lug 435 through the slot 520 in the connected position provides visual confirmation that a correct connection has been established. Also, the use of a slotted engagement member enables the cover to be made smaller. Engagement between the rim and the surface surrounding the venting area is similar to that discussed above.

FIGS. 9-1 to 9-6 include structure to allow various tooling operations. For example, FIGS. 9-1 to 9-2 have a 90 degree shutoff, FIGS. 9-3 to 9-4 have a 45 degree shutoff, and FIGS. 9-5 to 9-6 have a line of draw shutoff. Each of these results in slightly different engagement surfaces between the slot 520 of the cover 390 and the lug 435 of the elbow 385.

FIG. 9-9 shows an elbow 385 having a cover 390 which includes a scalloped or cut out section 525, which may aid in stability. This provides a manufacturing advantage in that a slider of molding equipment can be inserted and withdrawn in a direction 386 normal to the pull direction 387 when separating the cover 390 from the elbow 385.

Figures 5, 6, 7, 8, 9, 10, 11:
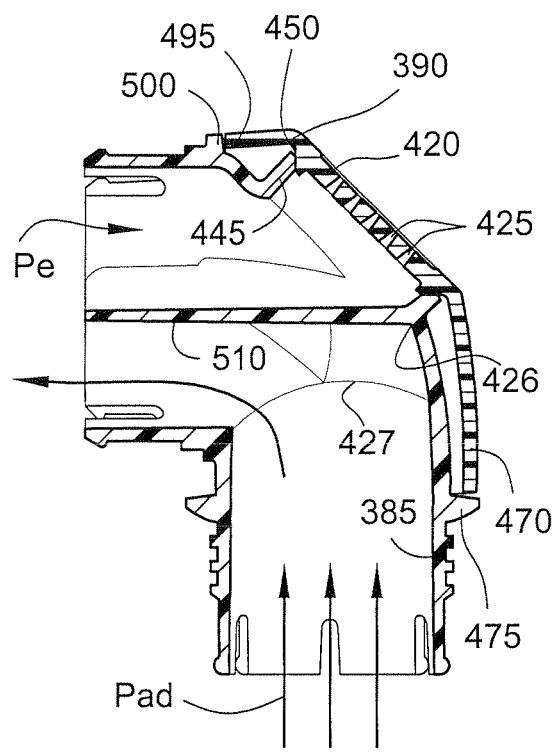
Figures 5, 6, 7, 8, 9, 10, 11, 12:
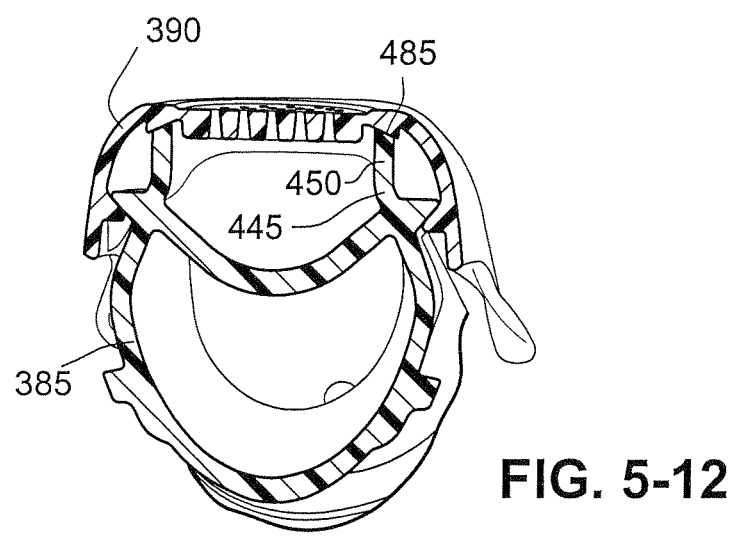
Figures 1, 6:
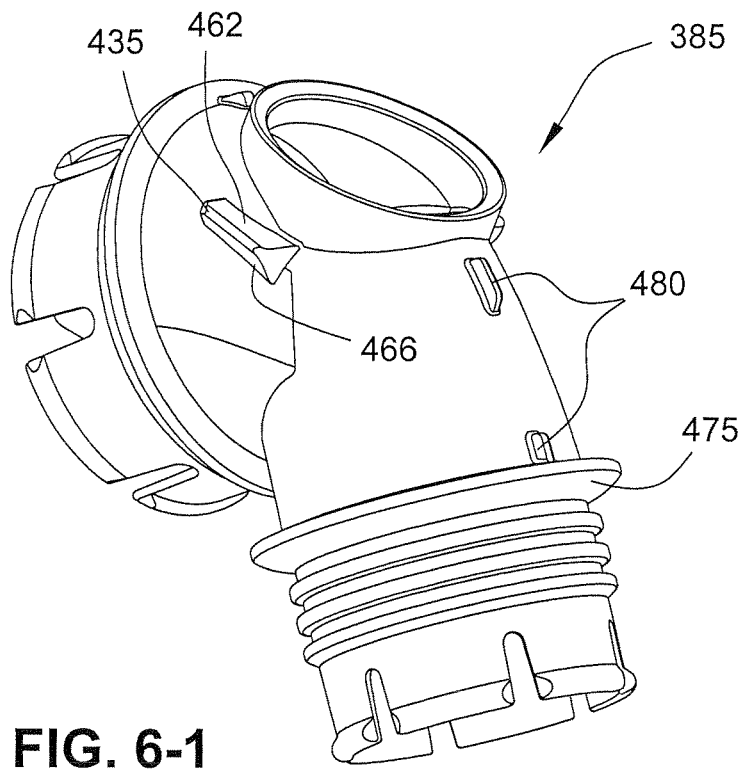
Figures 2, 6:
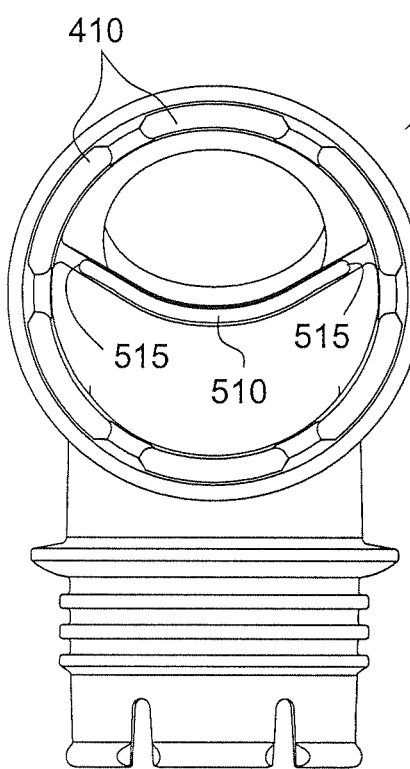
Figures 3, 6:
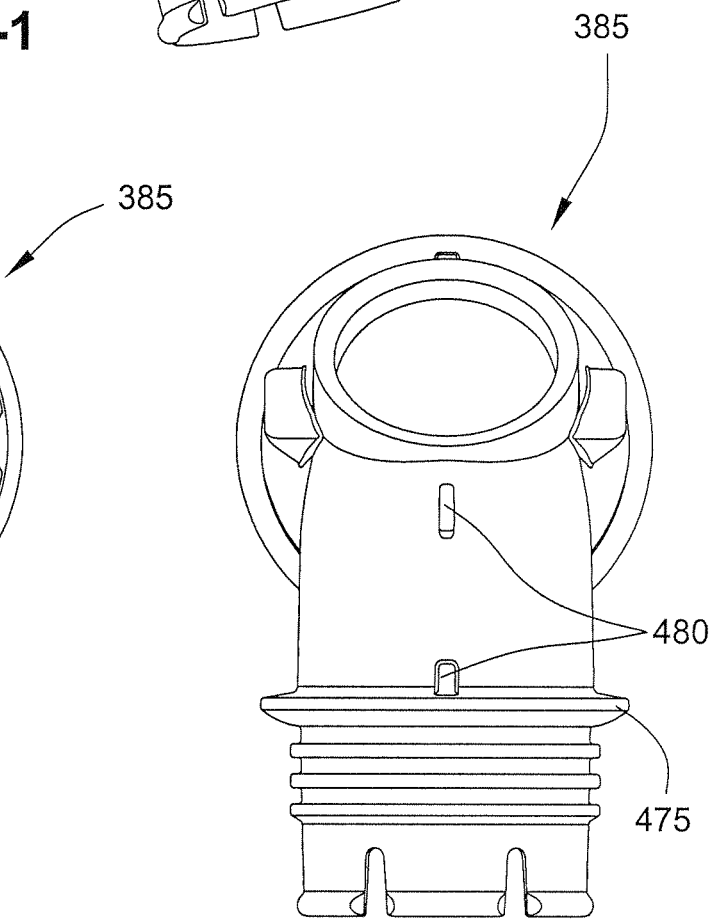
Figures 4, 6:
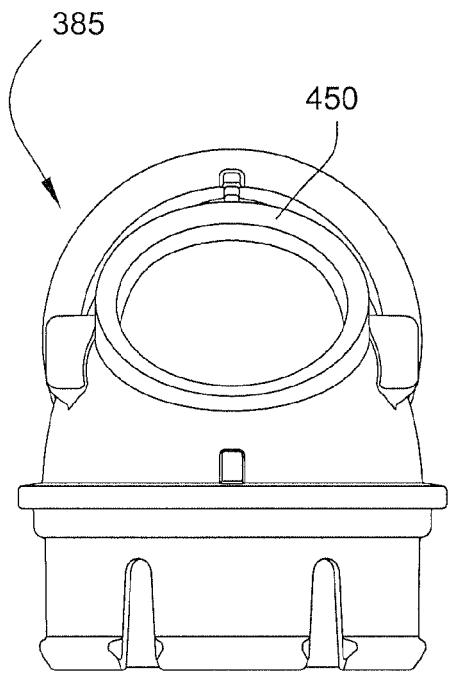
Figures 5, 6:
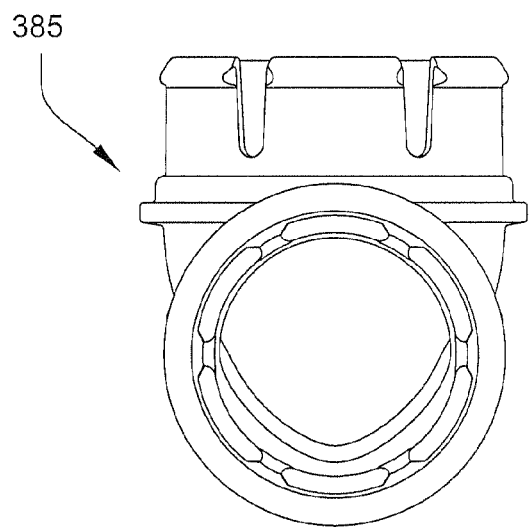
Figure 6:
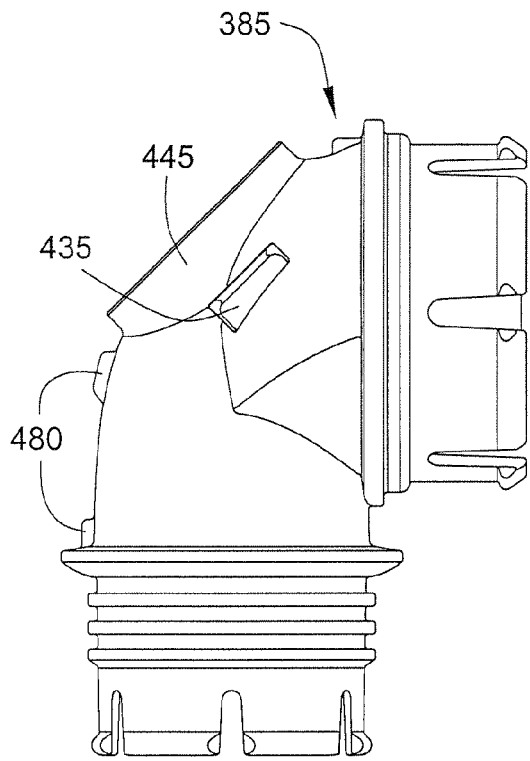
Figures 6, 7:
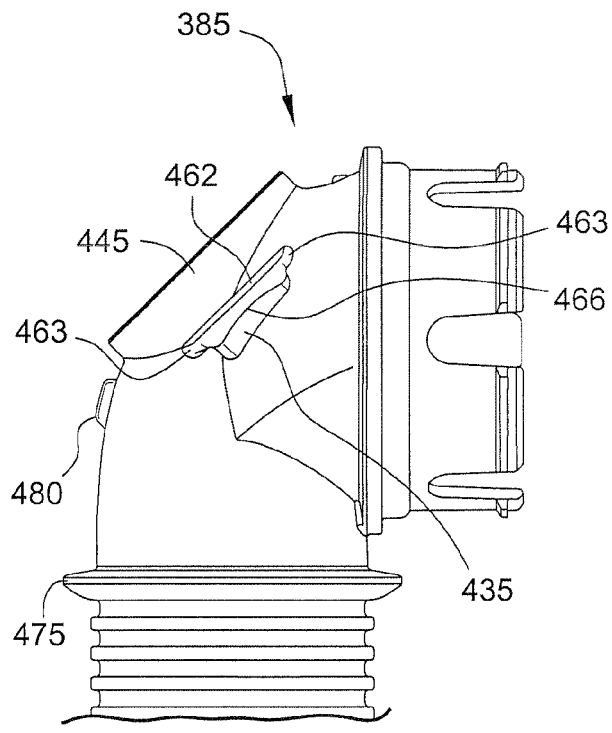
Figures 1, 7:
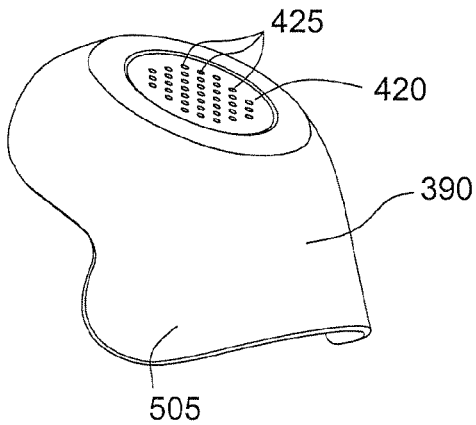
Figures 2, 7:
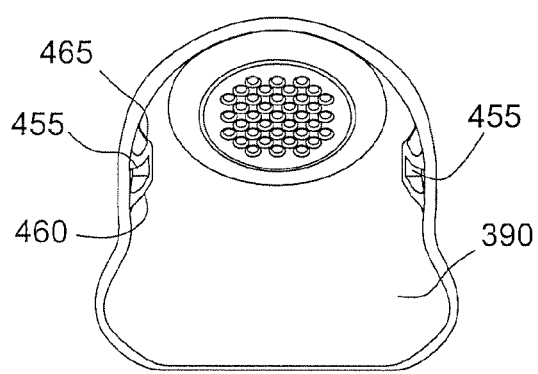
Figures 3, 7:
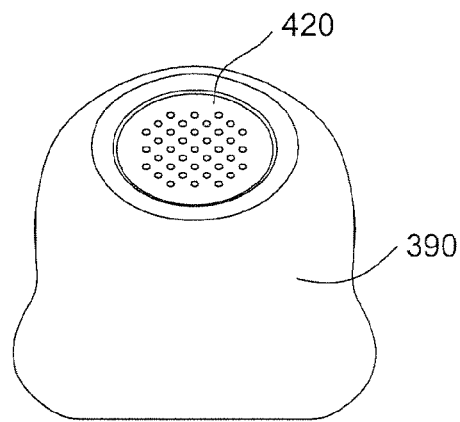
Figures 4, 7:
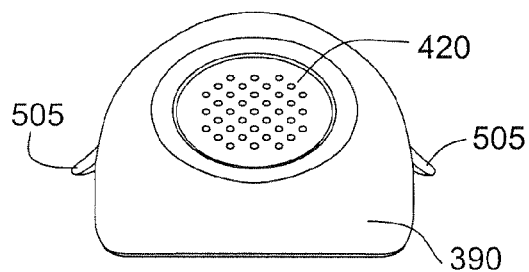
Figures 5, 7:
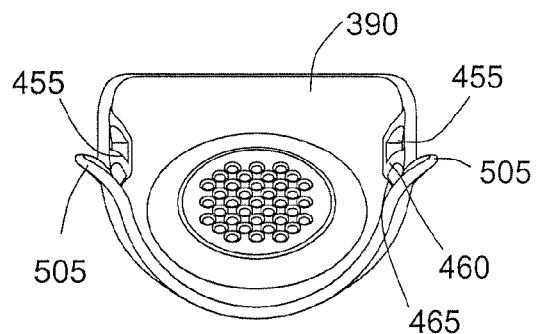
Figures 6, 7:
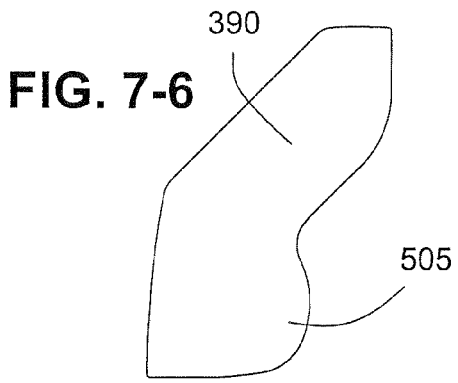
Figure 7:
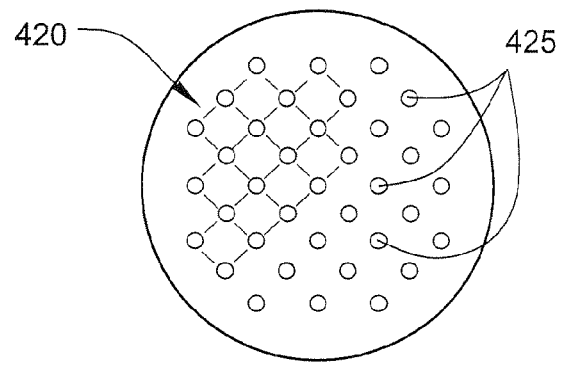
Figures 7, 8:
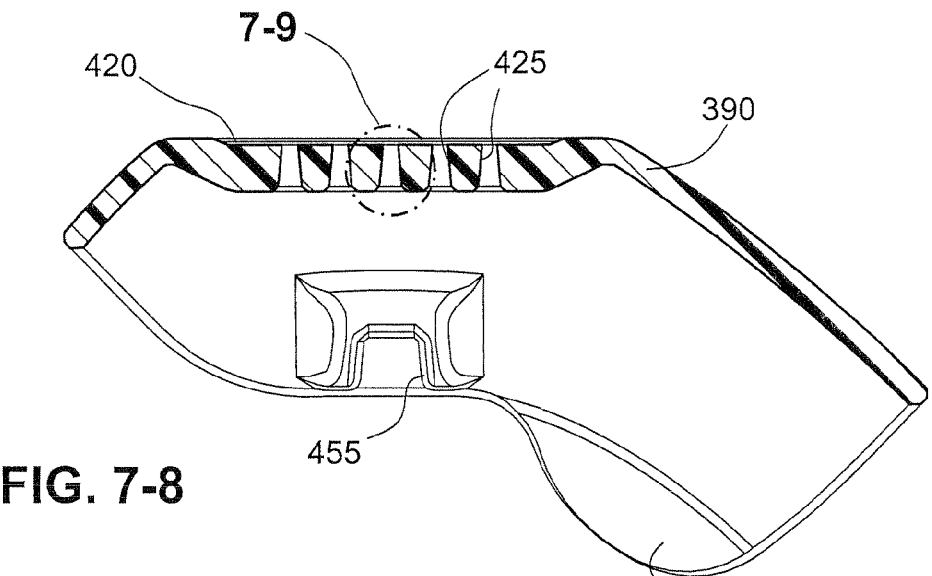
Figures 7, 8, 9:
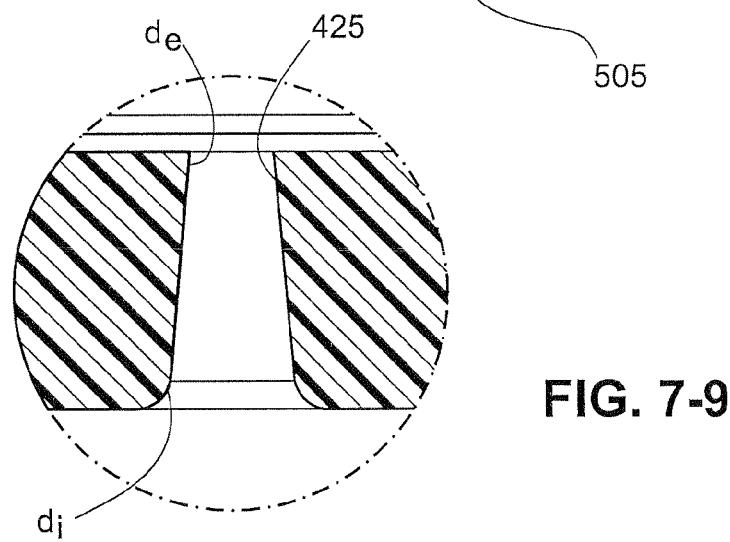
Figures 7, 8, 9, 10:
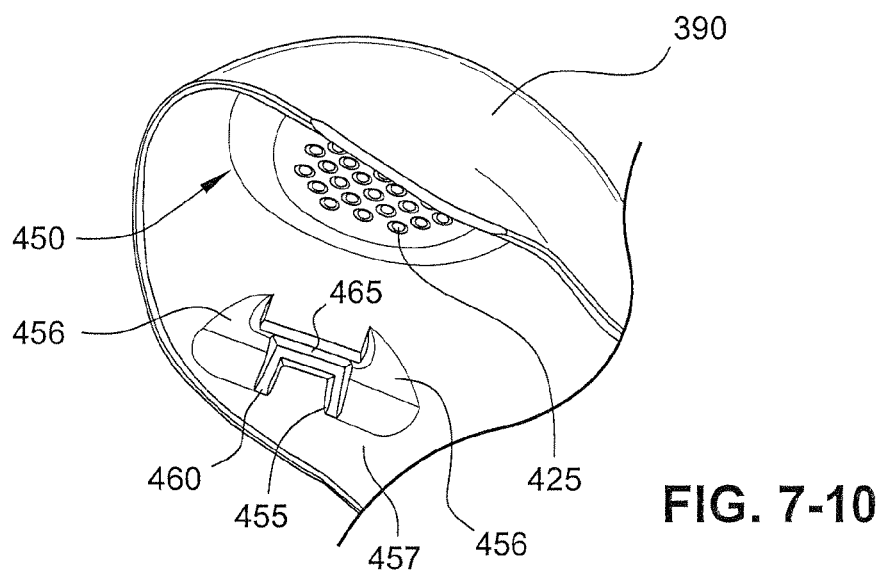
Figures 7, 8, 9, 10, 11:
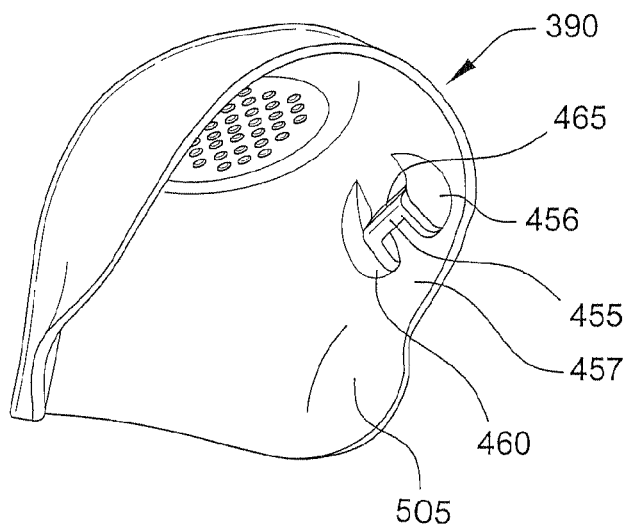
Figures 7, 8, 9, 10, 11, 12:
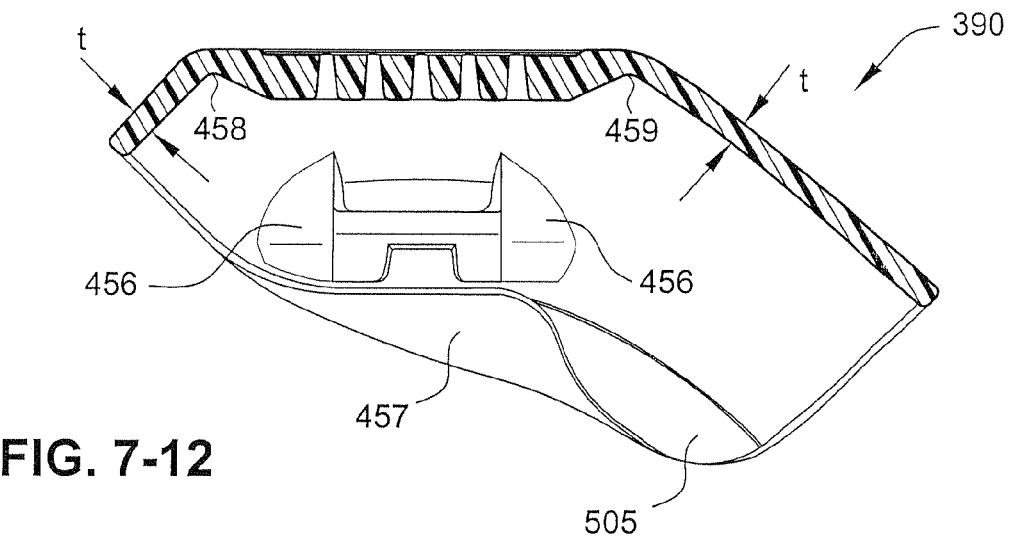
Figures 1, 8:
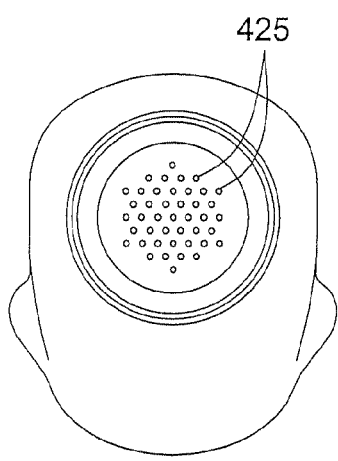
Figures 2, 8:
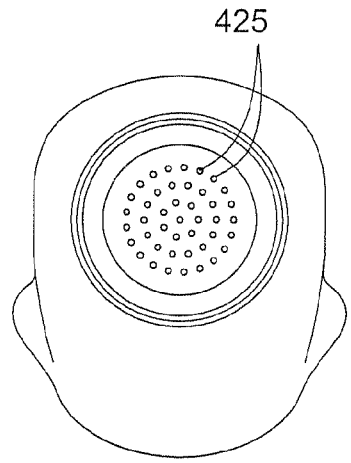

FIGS. 9-10 and 9-11 show an elbow 385 with a segmented flange 530, whereby the flange 530 includes cut out portions 535 which correspond to the position where the sides of the baffle are located in the inside of the elbow 385, to allow flexing. Cover 390 includes a leg 540 that may engage with the cut out 535. The leading edge of the leg 540 may be rounded to facilitate insertion within cut out 535.

FIGS. 9-12 and 9-13 illustrate variants of the wing 505, in which FIG. 9-12 shows lateral wings 505 which are elongated and extend in a direction further towards the first end of elbow 385. FIG. 9-13 shows a single wing 505 on the cover 390, which presents a large hood essentially aligned with but lower than the venting area.

FIG. 9-14 illustrates the elbow of FIG. 6-7 connected to the cover 390 of FIGS. 7-12.

FIGS. 9-15 to 9-24 illustrate embodiments whereby the venting area is formed directly on the elbow rather than a separate cover. Each elbow includes first and second ends that are selectively couplable to the frame and swivel, respectively.

FIG. 9-15 shows an elbow with a recessed venting portion having a triangular or pie shaped venting portion with a plurality of holes 425. FIG. 9-16 is similar, but the venting portion 420 is protruding rather than recessed.

FIGS. 9-17 and 9-20 show elbows where the venting portion 420 has a compound shape, including a part circular upper portion 421 and a cut out interior or lower portion 423 where the lower leg of the elbow is formed. FIG. 9-21 shows an elbowing two venting portions 420 separated by the lower leg of the elbow.

FIG. 9-18 is similar to FIG. 9-16, but the venting portion 420 is more radiused and has softer corners.

FIG. 9-21 shows an elbow with a generally cylindrical lower leg portion 424 which includes a circular top portion 428 including the venting area 420.

FIGS. 9-22 to 9-24 show an elbow 385 which includes a U-shaped baffle 510 that is unsupported along a least a portion of its length along the interior side walls of the elbow. The baffle 510 defines an intake passage and an exhaust passage that is in communication with a venting area 420 integrally formed with the elbow main body. Venting portion 420 is angled such that it is oriented to face towards the second end of the elbow 385.

6.0 Cushion

FIGS. 10-1 to 10-14 show cushion 20 which can be repeatedly attached to and detached from frame 10. FIGS. 10-1 and 10-2 are exploded views with the cushion 20 detached from the frame 10, while FIGS. 10-3 to 10-8 show various views of the cushion 20, and FIGS.-10-9 to 10-14 are cross sections of the cushion 20.

Cushion 20 includes a face engaging portion 550 and an opposed frame engaging portion 555. Face engaging portion 550 includes a multilayer construction, e.g., including an undercushion layer (UCL) 560 and a membrane 565 over the UCL 560. The UCL 560 is relatively thicker than the membrane 565 and serves as a support layer to the membrane 565.

Frame engaging portion 555 includes a relatively thickened, tongue like member 570 of a tongue and groove arrangement. Cushion 20 includes a shoulder 575 (see FIG. 10-8) which is flush with the top of the channel 240 upon full insertion, which can help provide a visual clue of correct assembly. The groove or channel 240 is formed in the frame 10 between inner and outer walls, 250, 245 shown in FIG. 10-2. Groove 240 includes a retaining bead as described above.

Frame engaging portion 555 includes a lip 580 (FIG. 10-9) which is intended to engage with the bead provided within the channel 240. In the case of the bead 255 being a split bead, opposing portions of the split bead engage the lip 580 to improve the retention of the cushion in the channel.

Cushion 20 includes an alignment structure or indicator 585 in the form of an arrowhead or carat or symbol which aligns with a complementary structure on frame 10. Apex of cushion 20 includes a single indicator 585, while the lower wall and the frame include two such pairs of indicators 585 visible in FIG. 1-6.

Cushion 20, in particular the frame engaging side 555, has a curved profile as best seen in FIG. 10-8. While the cushion could have a flat frame engaging side 555, the curvature helps to establish a firm and complete connection between the cushion 20 and frame 10 during assembly. The curved profile forms a sort of strengthening arch so the user may apply an assembly force to a laterally central region of the face engaging portion 550 of the cushion 20 (corresponding to the peak of the arch) to cause the frame engaging portion 550 to be inserted into frame 10. The applied force is sufficient to cause not only the peak of the arch opposite the central portion but the apex and bottom portion of the cushion 20 to establish a firm connection as well, such that the frame engaging portion 555 of the cushion 20 is secured around its entire perimeter. In this connection, the frame engaging portion 555 has a relatively thick gauge so that the cushion 20 maintains its shape during the assembling process. Further, the cushion side walls where the force is applied has a relatively thick gauge to help maintain shape. Cushion 20 is made of an elastomer such as silicone, in a one shot molding process.

FIGS. 10-9 to 10-14 are cross sections of the cushion and more clearly show various features of the cushion, including the UCL 560, membrane 565, shoulder 575, and lip 580, etc. For example, the cross sectional figures show the distance between the UCL and membrane in various portions around the perimeter of the cushion. FIGS. 11-1 to 11-6 and 12-1 to 12-6 show two additional embodiments of the cushion 20', 20" that are intended to better fit patients with various anthropometric features.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A mask assembly adapted for use with a positive airway pressure device, comprising:
    a mask frame including a neck and a support provided to a free, distal end of the neck;
    a cushion adapted to contact a patient's face;
    a forehead support assembly provided to the support of the frame, the forehead support assembly including a forehead pad; and
    an elbow assembly provided to the frame, the elbow assembly including an elbow and a vent attached thereto, the vent including a plurality of vent holes for gas washout,
    the neck comprising a first edge and a second edge, wherein
    the first edge and the second edge comprise a lower converging section wherein the first edge and the second edge converge towards one another in an upward direction and the first edge and second edge comprise an upper converging section wherein the first edge and the second edge converge towards one another in a downward direction, and
    the mask assembly is configured so that a relatively narrow portion of the neck overlies the bridge of the nose or is between the eyes of a user, the relatively narrow portion being a portion of the neck where a distance between the first edge and second edge is smallest, wherein the forehead support assembly and forehead pad thereof is linearly adjustable with respect to the support such that the forehead support assembly and forehead pad thereof may be adjusted in a number of discrete positions spaced from and relative to a forehead of a user, wherein the frame includes an elbow opening structured to engage with the elbow assembly, and the frame includes an open space above the elbow opening, wherein at least a lower portion of the first edge and the second edge extends below an apex of the cushion, and at least a front side of the open space is provided between the lower portion of the first edge and the second edge extending below the apex of the cushion, and wherein said lower converging section, said relatively narrow portion, and said upper converging section of the neck are positioned (a) above the apex of the cushion and (b) below the support of the frame.

2. The mask assembly according to claim 1, wherein the neck is integrally molded with the frame.

3. The mask assembly according to claim 1, wherein the neck is made of transparent material.

4. The mask assembly according to claim 1, wherein the first edge and second edge have a compound shape which is part parallel, part converging and part diverging.

5. The mask assembly according to claim 1, wherein the neck blends with and has a continuous form with other parts of the mask.

6. The mask assembly according to claim 1, wherein the first edge and the second edge join to an edge of the frame in a smooth, congruous manner without sharp edges.

7. The mask assembly according to claim 1, wherein the first edge and the second edge are joined to a portion of the forehead support assembly in a congruous, smooth manner.

8. The mask assembly according to claim 1, wherein the first edge and the second edge both include a radiussed curvature.

9. The mask assembly according to claim 1, wherein the cushion is one of a nasal cushion or full face cushion.

10. The mask assembly according to claim 1, wherein the neck comprises a wall comprising the first edge and the second edge.

11. The mask assembly according to claim 10, wherein the wall has a thickness of about 1 mm-5 mm.

12. The mask assembly according to claim 11, wherein the thickness is about 2.5 mm.

13. The mask assembly according to claim 10, wherein the profile thickness of the neck is substantially larger than a thickness of the wall.

14. The mask assembly according to claim 1, wherein a longitudinal length of the neck is substantially larger than a width of the neck as seen in front view.

15. The mask assembly according to claim 1, wherein lower ends of a front edge and a rear edge of the neck converge towards one another in an upward direction as seen in side view.

16. The mask assembly according to claim 15, wherein the front edge and the rear edge converge upwards from the apex of the cushion.

17. The mask assembly according to claim 15, wherein at least a portion of the front edge includes a radiussed curvature.

18. The mask assembly according to claim 1, wherein the vent includes 20-60 holes.

19. The mask assembly according to claim 1, wherein each vent hole converges from an inside of the vent to an outside of the vent such that an exit diameter of the hole is smaller than an inlet diameter of the hole.

20. The mask assembly according to claim 1, wherein at least a portion of the holes are arranged in a hole pattern having a diamond like shape.

21. The mask assembly according to claim 1, wherein the elbow is attached to the frame by a cerclip engaged around a groove at an end of the elbow.

22. A mask assembly adapted for use with a positive airway pressure device, comprising:

a mask frame including a neck and a support provided to a free, distal end of the neck;

a cushion proximate the frame;

a forehead support assembly provided to the support of the frame, the forehead support assembly including a forehead pad; and an elbow assembly provided to the frame, the elbow assembly including an elbow and a vent attached thereto, the vent including a plurality of vent holes for gas washout, the neck comprising a first edge and a second edge, wherein the first edge and the second edge comprise a lower converging section wherein the first edge and the second edge converge towards one another in an upward direction and the first edge and second edge comprise an upper converging section wherein the first edge and the second edge converge towards one another in a downward direction.

the neck has a generally hourglass shape and is configured so that a relatively narrow portion of the neck overlies the bridge of the nose or is between the eyes of a user, the relatively narrow portion being a portion of the neck where a distance between the first edge and second edge is smallest, wherein the forehead support assembly and forehead pad thereof is linearly adjustable with respect to the support such that the forehead support assembly and forehead pad thereof may be adjusted in a number of discrete positions spaced from and relative to a forehead of a user, and wherein said lower converging section, said relatively narrow portion, and said upper converging section of the neck are positioned (a) above an apex portion of the cushion immediately adjacent the frame and (b) below the support of the frame.

23. The mask assembly according to claim 22, wherein the neck is integrally molded with the frame.

24. The mask assembly according to claim 23, wherein the neck comprises a wall comprising the first edge and the second edge.

25. The mask assembly according to claim 24, wherein the wall has a thickness of about 1 mm-5 mm.

26. The mask assembly according to claim 25, wherein the neck is made of transparent material.

27. The mask assembly according to claim 26, wherein the profile thickness of the neck is substantially larger than a thickness of the wall.

28. The mask assembly according to claim 27, wherein the first edge and second edge of the wall have a compound shape which is part parallel, part converging and part diverging.

29. The mask assembly according to claim 28, wherein the neck blends with and has a continuous form with other parts of the mask.

30. The mask assembly according to claim 29, wherein the first edge and the second edge of the wall join to an edge of the frame in a smooth, congruous manner without sharp edges.

31. The mask assembly according to claim 30, wherein the first edge and the second edge of the wall both include a radiussed curvature.

32. The mask assembly according to claim 31, wherein the cushion is one of a nasal cushion or a full face cushion.

33. The mask assembly according to claim 22, wherein the neck is made of transparent material.

34. The mask assembly according to claim 22, wherein the first edge and second edge have a compound shape which is part parallel, part converging and part diverging.

35. The mask assembly according to claim 22, wherein the neck blends with and has a continuous form with other parts of the mask.

36. The mask assembly according to claim 22, wherein the first edge and the second edge join to an edge of the frame in a smooth, congruous manner without sharp edges.

37. The mask assembly according to claim 22, wherein the first edge and the second edge both include a radiussed curvature.

38. The mask assembly according to claim 22, wherein the cushion is one of a nasal cushion or a full face cushion.

39. The mask assembly according to claim 22, wherein the neck comprises a wall comprising the first edge and the second edge.

40. The mask assembly according to claim 39, wherein the wall has a thickness of about 1 mm-5 mm.

41. The mask assembly according to claim 40, wherein the thickness is about 2.5 mm.

42. The mask assembly according to claim 39, wherein the profile thickness of the neck is substantially larger than a thickness of the wall.

43. A mask assembly adapted for use with a positive airway pressure device, comprising:
- a mask frame including a neck and a support provided to a free, distal end of the neck;
- a cushion adapted to contact a patient's face;
- a forehead support assembly provided to the support of the frame, the forehead support assembly including forehead padding; and
- an elbow assembly provided to the frame, the elbow assembly including an elbow and a vent attached thereto, the vent including a plurality of vent holes for gas washout,
- the neck comprising a first edge and a second edge, wherein
- the first edge and the second edge of a lower converging section converge towards one another in an upward direction and the first edge and second edge of an upper converging section converge towards one another in a downward direction, and
- the mask assembly is configured so that a relatively narrow portion of the neck overlies the bridge of the nose or is between the eyes of a user, the relatively narrow portion being a portion of the neck where a distance between the first edge and second edge is smallest,
- wherein the neck is integrally molded with the frame and provides a continuous form from lower ends to upper ends of the first edge and the second edge,
- wherein the forehead support assembly and forehead pad thereof is linearly adjustable with respect to the support such that the forehead support assembly and forehead pad thereof may be adjusted in a number of discrete positions spaced from and relative to a forehead of a user, and
- wherein said lower converging section, said relatively narrow portion, and said upper converging section are positioned (a) above an apex of the cushion and (b) below the support of the frame.

44. The mask assembly according to claim 43, wherein the neck comprises a wall comprising the first edge and the second edge.

45. The mask assembly according to claim 44, wherein the wall has a thickness of about 1 mm- 5 mm.

46. The mask assembly according to claim 45, wherein the thickness is about 2.5 mm.

47. The mask assembly according to claim 44, wherein the profile thickness of the neck is substantially larger than a thickness of the wall.

48. The mask assembly according to claim 43, wherein the neck is made of transparent material.

49. The mask assembly according to claim 43, wherein the first edge and second edge have a compound shape which is part parallel, part converging and part diverging.

50. The mask assembly according to claim 43, wherein the first edge and the second edge join to an edge of the frame in a smooth, congruous manner without sharp edges.

51. The mask assembly according to claim 43, wherein the first edge and the second edge are joined to a portion of the forehead support assembly in a congruous, smooth manner.

52. The mask assembly according to claim 43, wherein the first edge and the second edge both include a radiussed curvature.

53. The mask assembly according to claim 43, wherein the cushion is one of a nasal cushion or full face cushion.

54. The mask assembly according to claim 43, wherein the forehead padding includes a pair of support shafts each including a head portion to connect the forehead padding to the forehead support assembly.

* * * * *

UNITED STATES PATENT AND TRADEMARK OFFICE
CERTIFICATE OF CORRECTION

| | |
|---|---|
| PATENT NO. | : 8,875,709 B2 |
| APPLICATION NO. | : 12/117084 |
| DATED | : November 4, 2014 |
| INVENTOR(S) | : Davidson et al. |

It is certified that error appears in the above-identified patent and that said Letters Patent is hereby corrected as shown below:

In the claims:

In claim 22 at column 18, lines 29-30, "second edge converge towards one another in a downward direction." should read ---second edge converge towards one another in a downward direction,---.

Signed and Sealed this
Nineteenth Day of May, 2015

Michelle K. Lee
*Director of the United States Patent and Trademark Office*